United States Patent
Nguyen et al.

(10) Patent No.: US 10,273,268 B2
(45) Date of Patent: Apr. 30, 2019

(54) HIV VACCINE FORMULATION

(71) Applicant: Janssen Vaccines & Prevention B.V., Leiden (NL)

(72) Inventors: Thierry-Thien Nguyen, Wilmington, DE (US); Mark Bruner, Norristown, PA (US)

(73) Assignee: Janssen Vaccines & Prevention B.V., Leiden (NL)

( * ) Notice: Subject to any disclaimer, the term of this patent is extended or adjusted under 35 U.S.C. 154(b) by 0 days.

(21) Appl. No.: 15/623,684

(22) Filed: Jun. 15, 2017

(65) Prior Publication Data
US 2017/0362280 A1 Dec. 21, 2017

Related U.S. Application Data

(60) Provisional application No. 62/350,919, filed on Jun. 16, 2016.

(51) Int. Cl.
*C07K 14/005* (2006.01)
*A61K 39/12* (2006.01)
(Continued)

(52) U.S. Cl.
CPC .......... *C07K 14/005* (2013.01); *A61K 31/047* (2013.01); *A61K 31/198* (2013.01);
(Continued)

(58) Field of Classification Search
None
See application file for complete search history.

(56) References Cited

U.S. PATENT DOCUMENTS 4,603,112 A 7/1986 Paoletti et al.
5,185,146 A 2/1993 Altenburger
(Continued)

FOREIGN PATENT DOCUMENTS

CN 102282175 A 12/2011
WO 0119958 3/2001
(Continued)

OTHER PUBLICATIONS

Lodi et al., "Immunovirologic Control 24 Months After Interruption of Antiretroviral Therapy Initiated Close to HIV Seroconversion", Archives of Internal Medicine, vol. 172, No. 16, pp. 1252-1255 (2012).
(Continued)

*Primary Examiner* — Janet L Andres
*Assistant Examiner* — Stuart W Snyder
(74) *Attorney, Agent, or Firm* — Panitch Schwarze Belisario & Nadel LLP

(57) ABSTRACT

Immunogenic compositions containing a human immunodeficiency virus (HIV) gp140 protein, sorbitol, polysorbate 20, and histidine buffer are described. The described immunogenic compositions are advantageous in that they are stable at refrigerated temperature for extended periods of time, and are compatible with an adjuvant. Also described are methods of using the immunogenic compositions to induce an immune response against an HIV in a subject. The immunogenic compositions can be administered alone, or in combination with one or more additional HIV antigens, or one or more adenovirus vectors encoding the one or more additional HIV antigens.

24 Claims, 4 Drawing Sheets
Specification includes a Sequence Listing.

(51) Int. Cl.

| | | |
|---|---|---|
| *A61K 39/21* | (2006.01) | |
| *A61K 39/38* | (2006.01) | |
| *C07K 14/16* | (2006.01) | |
| *C12N 15/09* | (2006.01) | |
| *A61K 31/047* | (2006.01) | |
| *A61K 31/198* | (2006.01) | |
| *A61K 39/00* | (2006.01) | |

(52) U.S. Cl.
CPC .............. *A61K 39/12* (2013.01); *A61K 39/21* (2013.01); *A61K 39/38* (2013.01); *C07K 14/16* (2013.01); *C12N 15/09* (2013.01); *A61K 39/00* (2013.01); *A61K 2039/525* (2013.01); *A61K 2039/55505* (2013.01); *C12N 2740/16122* (2013.01); *C12N 2740/16134* (2013.01)

(56) References Cited

U.S. PATENT DOCUMENTS

| | | | |
|---|---|---|---|
| 5,639,649 A | 6/1997 | Almond et al. | |
| 5,643,576 A | 7/1997 | Johnston et al. | |
| 6,761,893 B2 | 7/2004 | Chaplin et al. | |
| 6,911,205 B2 | 6/2005 | Sodroski et al. | |
| 7,592,014 B2 | 9/2009 | Binley et al. | |
| 7,901,690 B2 | 3/2011 | Lu et al. | |
| 7,939,083 B2 * | 5/2011 | Dey ..................... | A61K 39/21 424/188.1 |
| 8,034,378 B2 * | 10/2011 | O'Hagan ............. | A61K 9/0019 424/184.1 |
| 8,197,825 B2 | 6/2012 | Sutter et al. | |
| 9,017,691 B2 | 4/2015 | Barouch et al. | |
| 2003/0206926 A1 | 11/2003 | Chaplin et al. | |
| 2003/0207287 A1 | 11/2003 | Short | |
| 2006/0159699 A1 | 7/2006 | Howley et al. | |
| 2007/0166784 A1 | 7/2007 | Barnett et al. | |
| 2007/0298051 A1 | 12/2007 | Barouch et al. | |
| 2008/0199939 A1 | 8/2008 | Havenga et al. | |
| 2008/0279879 A1 | 11/2008 | Zolla-Pazner | |
| 2011/0159036 A1 | 6/2011 | Moss et al. | |
| 2011/0250220 A1 | 10/2011 | Dey et al. | |
| 2012/0045472 A1 | 2/2012 | Harrison et al. | |
| 2012/0076812 A1 | 3/2012 | Barouch et al. | |
| 2013/0189754 A1 | 7/2013 | Parks et al. | |
| 2014/0302080 A1 | 10/2014 | Barouch et al. | |
| 2014/0348791 A1 | 11/2014 | Barouch et al. | |
| 2015/0291935 A1 | 10/2015 | Barouch et al. | |
| 2016/0024156 A1 | 1/2016 | Barouch et al. | |
| 2016/0122392 A1 | 5/2016 | Baker et al. | |
| 2017/0165355 A1 | 6/2017 | Langedijk | |
| 2017/0362280 A1 | 12/2017 | Nguyen et al. | |
| 2018/0064803 A1 | 3/2018 | Tomaka | |
| 2018/0072777 A1 | 3/2018 | Rutten et al. | |

FOREIGN PATENT DOCUMENTS

| | | |
|---|---|---|
| WO | 200242480 A2 | 5/2002 |
| WO | 2003048184 A2 | 6/2003 |
| WO | 2003/104467 A1 | 12/2003 |
| WO | 2004/0044155 | 5/2004 |
| WO | 2006002079 | 1/2006 |
| WO | 2006020071 | 2/2006 |
| WO | 2006/040330 | 4/2006 |
| WO | 2007005934 | 1/2007 |
| WO | 2007/024941 | 3/2007 |
| WO | 2007/104792 A2 | 9/2007 |
| WO | 2007/149491 | 12/2007 |
| WO | 2008063331 | 5/2008 |
| WO | 2008107370 A1 | 9/2008 |
| WO | 2010/042942 A2 | 4/2010 |
| WO | 2010/059732 A1 | 5/2010 |
| WO | 2010096561 A1 | 8/2010 |
| WO | 2011/082087 A2 | 7/2011 |
| WO | 2011/092029 A1 | 8/2011 |
| WO | 2012/030904 | 3/2012 |
| WO | 2013055908 | 4/2013 |
| WO | 2014/047261 | 3/2014 |
| WO | 2014107744 A1 | 7/2014 |
| WO | 2014/124301 A1 | 8/2014 |
| WO | 2015/048770 | 4/2015 |
| WO | 2016037154 A1 | 3/2016 |
| WO | 2016049287 A1 | 3/2016 |
| WO | 2017102929 A1 | 6/2017 |

OTHER PUBLICATIONS

Lopez-Sagaseta et al, "Self-Assembling Protein Nanoparticles In The Design Of Vaccines," Computational and Structural Biotechnology Journal, vol. 14, pp. 58-68 (2016).

Lore et al., "Myeloid and Plasmacytoid Dendritic Cells are Susceptible to Recombinant Adenovirus Vectors and Stimulate Polyfunctional Memory T Cell Responses", J. Immunol, vol. 179, No. 3, pp. 1721-1729 (2007).

Lynch et al, "The Development of CD4 Binding Site Antibodies During HIV-1 Infection," Journal of Virology, vol. 86, No. 14, pp. 7588-7595 (Jul. 2012).

Malherbe et al, "Sequential Immunization with a Subtype B HIV-1 Envelope Quasispecies Partially Mimics the In Vivo Development of Neutralizing Antibodies," Journal of Virology, vol. 85, No. 11, pp. 5262-5274 (Jun. 2011).

Mangeat et al, "Lentiviral Vectors and Antiretroviral Intrinsic Immunity," Human Gene Therapy, vol. 16, No. 8, pp. 913-920 (Aug. 2005).

Mascola et al, "Protection of Macaques Against Pathogenic Simian/Human Immunodeficiency Virus 89.6PD by Passive Transfer of Neutralizing Antibodies," Journal of Virology, vol. 73, No. 5, pp. 4009-4018 (May 1999).

Mascola et al, "Protection of Macaques Against Vaginal Transmission of a Pathogenic HIV-1/SIV Chimeric Virus by Passive Infusion of Neutralizing Antibodies," Nature Medicine, vol. 6, No. 2, pp. 207-210 (Feb. 2000).

Masopust et al., "Hidden Memories: Frontline Memory T Cells and Early Pathogen Interception", J. Immunol., vol. 188, No. 12, pp. 5811-5817 (2012).

Mast et al., "International Epidemiology of Human Pre-Existing Adenovirus (Ad) Type-5, Type-6, Type-26 and Type-36 Neutralizing Antibodies: Correlates of High Ad5 Titers and Implications for Potential HIV Vaccine Trials", Vaccine, vol. 28: pp. 950-957 (2010).

Mayr et al., "The Small Pox Vaccination Strain MVA: Marker, Genetic Structure, Experience Gained with the Parenteral Vaccination and Behavior in Organisms with a Debilitated Defence Mechanism," Zentralbl Bacteriol. vol. 167, pp. 375-390 (1978) (Abstract Only).

McBurney et al, "Evaluation of Heterologous Vaginal SHIV SF162p4 Infection Following Vaccination with a Polyvalent Clade B Virus-Like Particle Vaccine," AIDS Research and Humam Retroviruses, vol. 28, No. 9, pp. 863-872 (2012).

McBurney et al, "Human Immunodeficiency Virus-Like Particles with Consensus Envelopes Elicited Broader Cell-Mediated Peripheral and Mucosal Immune Responses than Polyvalent and Monovalent Env Vaccines," Vaccine, vol. 27, No. 32, pp. 4337-4349 (2009).

McCoy et al, "Potent and Broad Neutralization of HIV-1 by a Llama Antibody Elicited by Immunization," The Journal of Experimental Medicine, vol. 209, No. 6, pp. 1091-1103 (2012).

McElrath et al, "Induction of Immunity to Human Immunodeficiency Virus Type-1 by Vaccination," Immunity, vol. 33, pp. 542-554 (Oct. 29, 2010).

McElrath et al., "HIV-1 Vaccine-Induced Immunity in the Test-of-Concept Step Study: A Case-Cohort Analysis", Lancet, vol. 372, No. 9653, pp. 1894-1905 (2008).

McGuire et al., "Engineering HIV Envelope Protein to Activate Germline B Cell Receptors of Broadly Neutralizing Anti-CD4 Binding Site Antibodies," The Journal of Experimental Medicine, vol. 210, No. 4, pp. 655-663 (2013).

McLellan et al, "Structure of HIV-1 gp120 V1N2 Domain with Broadly Neutralizing Antibody PG9," Nature, vol. 480, No. 7377, pp. 336-343 (2011).

(56) References Cited

OTHER PUBLICATIONS

Montefiori et al, "Antibody-Based HIV-1 Vaccines: Recent Developments and Future Directions," PLOS Medicine, vol. 4, No. 12, pp. e348 (2007).
Montefiori, "Evaluating Neutralizing Antibodies Against HIV, SIV, and SHIV in Luciferase Reporter Gene Assays,", Current Protocols in Immunology, vol. 12, No. 11, pp. 1-17 (2004).
Montefiori, "Measuring HIV Neutralization in a Luciferase Reporter Gene Assay," HIV Protocols Second 25 Edition, vol. 485, pp. 395-405 (2009).
Morner et al, "Human Immunodeficiency Virus Type 1 ENV Trimer Immunization of Macaques and Impact of D Priming with Viral Vector or Stabilized Core Protein," Journal of Virology, vol. 83, No. 2, pp. 540-551 (Jan. 2009).
Mouquet et al, "Complex-Type N-Glycan Recognition by Potent Broadly Neutralizing HIV Antibodies," Proceedings of the National Academy of Sciences of the United States of America, vol. 109, No. 47, pp. E3268-E3277 (2012).
Nara et al, "Purified Envelope Glycoproteins from Human Immunodeficiency Virus Type 1 Variants Induce Individual, Type-Specific Neutralizing Antibodies," Journal of Virology, vol. 62, No. 8, pp. 2622-2628 (Aug. 1988).
NCBI Blast for GenBank AAY23526.1, Jul. 2016, "Envelope glycoprotein Human immunodeficiency virus 1", downloaded from web page: http://www.ncbi.nlm.nih.gov/protein/62956393, Download date: Feb. 8, 2018 (2 pages).
Nkolola et al, "Stability and Neutralization Capacity of a Novel Mosaic HIV-1 gp140 trimer in a Guinea Pig Model" AIDS Vaccine Poster, Ragon Institute, 1 pg. (2012).
Nkolola et al, "Stability and Neutralization Capacity of a Novel Mosaic HIV-1 gp140 Trimer in a Guinea Pig Model," Retrovirology, vol. 9, Supp. 2, pp. 299 (2012).
Ofek et al, "Structure and Mechanistic Analysis of the Anti-Human Immunodeficiency Virus Type 1 Antibody 2F5 in Complex with Its gp41 Epitope," Journal of Virology, vol. 78, No. 19, pp. 10724-10737 (Oct. 2004).
Page et al, "Studies on the Immunogenicity of Chinese Hamster Ovary Cell-Derived Recombinant gp120 (HIV-1111B)," Vaccine, vol. 9, pp. 47-52 (Jan. 1991).
Pancera et al, "Crystal Structure of PG16 and Chimeric Dissection with Somatically Related PG9: Structure-Function Analysis of Two Quaternary-Specific Antibodies That Effectively Neutralize HIV-1," Journal of Virology, vol. 84, No. 16, pp. 8098-8110 (Aug. 2010).
Pancera et al, "Structure of HIV-1 gp120 with gp41-Interactive Region Reveals Layered Envelope Architecture and Basis of Conformational Mobility," Procedures of the National Academy of Sciences of the United States of America, vol. 107, No. 3, pp. 1166-1171 (2010).
Pantophlet et al, "GP120: Target for Neutralizing HIV-1 Antibodies," Annu. Rev. Immunol., vol. 24, pp. 739-769 (2006).
Patterson et al. "Protection Against Mucosal Simian Immunodeficiency Virus SIVmac251 Challenge by Using Replicating Adenovirus-SIV Multigene Vaccine Priming and Subunit Boosting," Journal of Virology, vol. 78, No. 5, pp. 2212-2221 (Mar. 2004).
Pejchal et al, "A Potent and Broad Neutralizing Antibody Recognizes and Penetrates the HIV Glycan Shield," Science, vol. 334, No. 6059, pp. 1097-1103 (2011).
Pejchal et al, "Structure and Function of Broadly Reactive Antibody PG16 Reveal an H3 Subdomain that Mediates Potent Neutralization of HIV-1," Proceedings of the National Academy of Sciences of the United States of America, vol. 107, No. 25, pp. 11483-11488 (2010).
Peng et al. "Replicating Rather than Nonreplicating Adenovirus-Human Immunodeficiency Virus Recombinant Vaccines Are Better at Eliciting Potent Cellular Immunity and Priming High-Titer Antibodies," Journal of Virology, vol. 79, No. 16, pp. 10200-10209 (Aug. 2005).
Pinter, "Roles of HIV-1 Env Variable Regions in Viral Neutralization and Vaccine Development", Current HIV Research, vol. 5, No. 6, pp. 542-553 (2007).
Pitisuttihum et al., "Randomized, Double-Blind, Placebo-Controlled Efficacy Trial of a Bivalent Recombinant Glycoprotein 120 HIV-1 Vaccine Among Injection Drug Users in Bangkok, Thailand", J. Infect. Dis., vol. 194, No. 12, pp. 1661-1671 (2006).
Plotkin et al, "Postscript Relating to New Allegations Made by Edward Hooper at the Royal Society Discussion Meeting on Sep. 11, 2000," Philosophical Transactions of The Royal Society of London B: Biological Sciences, vol. 356, No. 1410, pp. 825-829 (2001).
Plotkin, "Correlates of Protection Induced by Vaccination," Clinical and Vaccine Immunology, vol. 17, No. 7, pp. 1055-1065 (Jul. 2010).
Plotkin, "Immunologic Correlates of Protection Induced by Vaccination," Pediatric Infectious Disease Journal, vol. 20, No. 1, pp. 63-75 (2001).
Plotkin, "The RV144 Thai HIV Vaccine Trial," Human Vaccines, vol. 6, No. 2, p. 159 (Feb. 2010).
Polonis et al, "Recent Advances in the Characterization of HIV-1 Neutralization Assays for Standardized Evaluation of the Antibody Response to Infection and Vaccination," Virology, vol. 375, pp. 315-320 (2008).
Pugach et al, "A Native-Like SOSIP.664 Trimer Based On An HIV-! Subtype B Env Gene," Journal of Virology, vol. 89, No. 6, pp. 3380-3395 (2015).
Rerks-Ngarm et al., Vaccination with ALVAC and AIDSVAX to Prevent HIV-1 Infection in Thailand, N. Engl J Med., vol. 361, No. 23, pp. 2209-2220 (2009).
Rodenburg et al, "Near Full-Length Clones and Reference Sequences for Subtype C Isolates of HIV Type 1 from Three Different Continents," AIDS Research and Human Retroviruses, vol. 17, No. 2, pp. 161-168 (2001).
Saez-Cirion et al., "Post-Treatment HIV-1 Controllers with a Long-Term Virological Remission after the Interruption of Early Initiated Antiretroviral Therapy ANRS VISCONTi Study", PLOS Pathogens, vol. 9, No. 3, 12 pgs (Mar. 2013).
Salminen et al, "Full-length Sequence of an Ethiopian Human Immunodeficiency Virus Type 1 (HIV-1) Isolate of Genetic Subtype C," AIDS Res. Human Retroviruses, vol. 12, No. 14, pp. 1329-1339 (1996).
Sanders et al, "HIV-1 Neutralizing Antibodies Induced By Native-Like Envelope Trimers," Science, vol. 349, Issue 6244, pp. 1-17 (2015).
Santra et al., "Mosaic Vaccines Elicit CD8+ T Lymphocyte Responses That Confer Enhanced Immune Coverage of Diverse HIV Strains in Monkeys", Nat Med., vol. 16, No. 3, pp. 324-328 (2010).
International Search Report and Written Opinion dated Sep. 13, 2017 in Int'l Application No. PCT/EP2017/064665.
Clapp et al. "Vaccines with Aluminum-Containing Adjuvants: Optimizing Vaccine Efficacy and Thermal Stability," J. Pharm. Sci. vol. 100, No. 2: pp. 388-401 (2011).
Wiggan et al. "Novel formulations enhance the thermal stability of live-attenuated flavivirus vaccines," Vaccine, vol. 29, pp. 7456-7462 (2011).
Saphire et al, "Crystal Structure of a Neutralizing Human IgG Against HIV-1: A Template for Vaccine Design," Science, vol. 293, No. 5532, pp. 1155-1159 (2001).
Sarzotti-Kelsoe et al, "Optimization and Validation of the TZM-bl Assay for Standardized Assessments of Neutralizing Antibodies Against HIV-1," Journal of Immunological Methods, vol. 409, pp. 131-146 (2014).
Sattentau, "Envelope Glycoprotein Trimers as HIV-1 Vaccine Immunogens", Vaccines, vol. 1, pp. 497-512 (2013).
Scheid et al, "Broad Diversity of Neutralizing Antibodies Isolated From Memory B Cells in HIV-Infected Individuals," D Nature, vol. 458, pp. 636-640 (Apr. 2, 2009).
Scheid et al, "Sequence and Structural Convergence of Broad and Potent HIV Antibodies That Mimic CD4 Binding," Science, vol. 333, pp. 1633-1637 (2011).
Schnierle et al, "Pseudotyping of Murine Leukemia Virus with the Envelope Glycoproteins of HIV Generates a Retroviral Vector with Specificity of infection for CD4-Expressing Cells," Proceedings of the National Academy of Sciences of the United States of America, vol. 94, pp. 8640-8645 (Aug. 1997).

(56) References Cited

OTHER PUBLICATIONS

Seaman et al, "Multiclade Human Immunodeficiency Virus Type 1 Envelope Immunogens Elicit Broad Cellular and Humoral Immunity in Rhesus Monkeys," Journal of Virology, vol. 79, No. 5, pp. 2956-2963 (2005).
Seaman et al, "Standardized Assessment of NAb Responses Elicited in Rhesus Monkeys Immunized with Single- or Multi-Glade HIV-1 Envelope Immunogens," Virology, vol. 367, pp. 175-186 (2007).
Muthumani et al., "HIV-1 Env DNA Vaccine plus Protein Boost Delivered by EP Expands B- and T-Cell Responses and Neutralizing Phenotype In Vivo", PLOS One, vol. 8, No. 12, 12 pgs (Dec. 2013).
Sharma et al, "Cleavage-Independent HIV-1 Env Trimers Engineered As Soluble Native Spike Mimetics For Vaccines Design," Cell Reports, vol. 11, pp. 1-12 (2015).
Simek et al, "Human Immunodeficiency Virus Type 1 Elite Neutralizers: Individuals With Broad and Potent Neutralizing Activity Identified by Using a High-Throughput Neutralization Assay Together With an Analytical Selection Algorithm," Journal of Virology, vol. 83, No. 14, pp. 7337-7748 (2009).
Sok et al, "Promiscuous Glycan Site Recognition by Antibodies to the High-Mannose Patch of gp120 Broadens Neutralization of HIV," Science Translational Medicine, vol. 6, No. 236, pp. 236ra63 (May 14, 2014).
Spranger et al., "Quantifying Adenovirus-Neutralizing Antibodies by Luciferase Transgene Detection: Addressing Preexisting Immunity to Vaccine and Gene Therapy Vectors", J. Clin. Microbiol, vol. 41, No. 11, pp. 5046-5052 (2003).
Stamatos et al, "Neutralizing Antibodies Generated During Natural HIV-1 Infection: Good News for an HIV-1 Vaccine?," Nature Medicine, vol. 15, No. 8, pp. 866-870 (2009).
Stickl, "Smallpox Vaccination and it's Consequences: First Experiences with the Highly Attenuated Smallpox Vaccine MVA", Preventive Medicine, vol. 3, pp. 97-101 (1974).
Tatsis et al., "A CD46-binding Chimpanzee Adenovirus Vector as a Vaccine Carrier", Molecular Therapy, vol. 15, No. 3, pp. 608-617 (2007).
Thompson et al., "DNA/MVA Vaccination of HIV-1 Infected Participants with Viral Suppression on Antiretroviral Therapy, Followed by Treatment Interruption: Elicitation of Immune Responses without Control of Re-Emergent Virus", PLOS One, vol. 11, No. 10, pp. 25 (Oct. 2016).
Thorner et al., "Age Dependence of Adenovirus-Specific Neutralizing Antibody Titer in Individuals From Sub-Saharan Africa", J. Clin. Microbiol, vol. 44, No. 10, pp. 3781-3783 (2006).
Thurmond et al., "Web-Based Design and Evaluation of T-cell Vaccine Candidates," Bioinformatics, vol. 24, No. 14, pp. 1639-1640 (2008).
UNAIDS, "Report on the Global AIDS Epidemic", 198 pgs (2013).
Vaine et al, "Antibody Responses Elicited through Homologous or Heterologous Prime-Boost DNA and Protein Vaccinations Differ in Functional Activity and Avidity," Vaccine, vol. 28, No. 17, pp. 2999-3007 (2010).
Vaine et al, "Improved Induction of Antibodies Against Key Neutralizing Epitopes by Human Immunodeficiency Virus Type 1 gp120 DNA Prime-Protein Boost Vaccination Compared to gp120 Protein-Only Vaccination," Journal of Virology, vol. 82, No. 15, pp. 7369-7378 (Aug. 2008).
Vaine et al, "Profiles of Human Serum Antibody Responses Elicited by Three Leading HIV Vaccines Focusing on the Induction of Env-Specific Antibodies," PLoS One, vol. 5, No. 11, pp. e13916 (Nov. 2010).
Vogel et al, "The Majority of Neutralizing Abs in HIV-1-Infected Patients Recognize Linear V3 Loop Sequences," The Journal of Immunology, vol. 153, pp. 1895-1904 (1994).
Vogels et al., "Replication-Deficient Human Adenovirus Type 35 Vecotrs for Gene Transfer and Vaccination: Efficient Human Cell Infection and Bypass of Preexisting Adenovirus Immunity", J. Virol, vol. 77, No. 15, pp. 8263-8271 (2003).

Walker et al, "Broad and Potent Neutralizing Antibodies from an African Donor Reveal a New HIV-1 Vaccine Target," Science, vol. 326, No. 5950, pp. 285-289 (Oct. 9, 2009).
Walker et al, "Broad Neutralization Coverage of HIV by Multiple Highly Potent Antibodies," Nature, vol. 477, No. 7365, pp. 466-470 (Sep. 22, 2011).
Walker et al, "Toward an AIDS Vaccine," Science, vol. 320, pp. 760-764 (May 9, 2008).
Wang et al, "Cross-Subtype Antibody and Cellular Immune Responses Induced by a Polyvalent DNA Prime-Protein Boost HIV-1 Vaccine in Healthy Human Volunteers," Vaccine, vol. 26, No. 31, pp. 3947-3957 (Jul. 23, 2008).
Wang et al, "Enhanced Immunogenicity of gp120 Protein when Combined with Recombinant DNA Priming to Generate Antibodies that Neutralize the JR-FL Primary Isolate of Human Immunodeficiency Virus Type 1," Journal of Virology, vol. 79, No. 12, pp. 7933-7937 (Jun. 2005).
Wang et al, "Polyvalent HIV-1 Env Vaccine Formulations Delivered by the DNA Priming Plus Protein Boosting Approach are Effective in Generating Neutralizing Antibodies Against Primary Human Immunodeficiency Virus Type 1 Isolates from Subtypes A, B, C, D and E," Virology, vol. 350, No. 1, pp. 34-47 (2006).
Watkins et al, "Immune Escape by Human Immunodeficiency Virus Type 1 from Neutralizing Antibodies: Evidence for Multiple Pathways," Journal of Virology, vol. 67, No. 12, pp. 7493-7500 (Dec. 1993).
Wattanapitayakul et al, "Recent Developments in Gene Therapy for Cardiac Disease," Biomed & Pharmacother, vol. 54, No. 1, pp. 487-504 (2000).
Williams et al., "HIV-1 DNA Predicts Disease Progression and Post-Treatment Virological Control", eLIfe, vol. 3, 16 pgs (2014).
Wiznerowicz et al, "Harnessing HIV for Therapy, Basic Research and Biotechnology," TRENDS in Biotechnology, vol. 23, No. 1, pp. 42-47 (Jan. 2005).
Written Opinion dated Mar. 21, 2014 in Int'l Application No. PCT/US2014/010543.
Shu et al., "Efficient Boosting After Plasmid DNA or Recombinant Adenovirus Immunization with HIV-1 Vaccine Constructs", Vaccine, vol. 25, No. 8, pp. 1398-1408 (2.
Wu et al, "Rational Design of Envelope Identifies Broadly Neutralizing Human Monoclonal Antibodies to HIV-1," Science, vol. 329, No. 5993, pp. 856-861 (Aug. 13, 2010).
Wyatt et al, "The Antigenic Structure of the HIV gp120 Envelope Glycoprotein," Nature, vol. 393, pp. 705-711 (Jun. 18, 1998).
Yang et al, "Improved Elicitation of Neutralizing Antibodies Against Primary Human Immunodeficiency Viruses by Soluble Stabilized Envelope Glycoprotein Trimers," Journal of Virology, vol. 75, No. 3, pp. 1165-1171 (Feb. 2001).
Yang et al, "Modifications That Stabilize Human Immunodeficiency Virus Envelope Glycoprotein Trimers in Solution," Journal of Virology, vol. 74, No. 10, pp. 4746-4754 (2000).
Yang et al., "Highly Stable Trimers Formed by Human Immunodeficiency Virus Type 1 Envelope Glycoproteins Fused with the Trimeric Motif of T4 Bacteriophage Fibritin", J. Virol., vol. 76, No. 9, pp. 4634-4642 (2002).
Yasmeen et al, "Differential Binding of Neutralizing and Non-Neutralizing Antibodies to Native-Like Soluble HIV-1 Env Trimers, Uncleaved Env Proteins, and Monomeric Subunits," Retrovirology, vol. 11, No. 41 (2014).
Zhang et al, "Extensively Cross-Reactive Anti-HIV-1 Neutralizing Antibodies Induced by gp140 Immunization," PNAS, vol. 104, No. 24, pp. 10193-10198 (2007).
Zhao et al, "Nanoparticle Vaccines," Vaccines, vol. 32, pp. 327-337 (2014).
Zhou et al, "Structural Basis for Broad and Potent Neutralization of HIV-1 by Antibody VRC01," Science, vol. 329, No. 5993, pp. 811-817 (Aug. 13, 2010).
Zolla-Pazner et al, "Focusing the Immune Response on the V3 Loop, a Neutralizing Epitope of the HIV-1 gp210 Envelope," Virology, vol. 372, pp. 233-246 (2008).
Barouch et al., "Accelerating HIV-1 Vaccine Efficacy Trials", Cell, vol. 159, No. 5, pp. 969-792 (Nov. 2014).

(56) References Cited

OTHER PUBLICATIONS

Derby et al, "Isolation and Characterization of Monoclonal Antibodies Elicited by Trimeric HIV-1 ENV gp140 Protein 14 Immunogens," Virology, vol. 366, pp. 433-445 (2007).
Desrosiers, "Prospects for an AIDS Vaccine", Nature Medicine, vol. 10, No. 3, pp. 221-223 (2004).
Dey et al, "Characterization of Human Immunodeficiency Virus Type 1 Monomeric and Trimeric gp120 Glycoproteins Stabilized in the CD4-Bound State: Antigenicity, Biophysics, and Immunogenicity," Journal of Virology, vol. 81, No. 11, pp. 5579-5593 (Jun. 2007).
Doores et al, "Antibody 2G12 Recognizes Di-Mannose Equivalently in Domain- and Nondomain-Exchanged Forms but Only Binds the HIV-1 Glycan Shield if Domain Exchanged," Journal of Virology, vol. 84, No. 20, pp. 10690-10699 (2010).
Doria-Rose et al, "Frequency and Phenotype of Human Immunodeficiency Virus Envelope-Specific B Cells from Patients with Broadly Cross-Neutralizing Antibodies," Journal of Virology, vol. 83, No. 1, pp. 188-199 (Jan. 2009).
Eglen et al, "The Use Of AlphaScreen Technology In HTS: Current Status," Current Chemical Genomics, vol. 1, pp. 2-10 (2008).
Engelhardt et al, "Ablation of E2A in Recombinant Adenoviruses Improves Transgene Persistence and Decreases Inflammatory Response in Mouse Liver," Proceedings of the National Academy of Sciences of the United States of America, vol. 91, No. 13, pp. 6196-6200 (Jun. 1994).
Falkowska et al, "PGV04, an HIV-1 gp120 CD4 Binding Site Antibody, is Broad and Potent in Neutralization but Does Not Induce Conformational Changes Characteristic of CD4," Journal of Virology, vol. 86, No. 8, pp. 4394-4403 (2012).
Farina et al., "Replication-defective Vector Based on a Chimpanzee Adenovirus", J. Virol, vol. 75, No. 23, pp. 11603-11613 (2001).
Fiebig et al, "Neutralizing Antibodies Against Conserved Domains of p15E of Porcine Endogenous Retroviruses: Basis for a Vaccine for Xenotransplantation?" Virology, vol. 307, No. 2, pp. 406-413 (2003).
Fischer et al, "Identification of a Peptide Mimicking the Binding Pattern of an Antiphospholipid Antibody," Immunobiology, vol. 211, No. 9, pp. 695-699 (2006).
Fischer et al., "Coping with Viral Diversity in HIV vaccine Design: A Response to Nickle et al.," PLoS Comput Bioi., vol. 4, No. 1, pp. 175-179 (2008).
Fischer et al., "Polyvalent Vaccines for Optimal Coverage of Potential T-Cell Epitopes in Global HIV-1 Variants", Nat. Med., vol. 13, No. 1, pp. 100-106 (Jan. 2007).
Flynn et al., "Placebo-controlled phase 3 trial of a recombinant glycoprotein 120 vaccine to prevent HIV-1 infection",. J. Infect Dis, vol. 191, No. 5, pp. 654-665 (2005).
Freeman et al, "Crystal Structure of HIV-1 Primary Receptor CD4 in Complex with a Potent Antiviral Antibody," Structure, vol. 18, No. 12, pp. 1632-1641 (Dec. 8, 2010).
Frey et al, "A Fusion-Intermediate State of HIV-1 gp41 Targeted by Broadly Neutralizing Antibodies," Proceedings of the National Academy of Sciences of the United States of America, vol. 105, No. 10, pp. 3739-3744 (Mar. 11, 2008).
Fynan et al, "DNA Vaccines: Protective Immunizations by Parenteral, Mucosal, and Gene-Gun Inoculations," Proceedings of the National Academy of Sciences of the United States of America, vol. 90, No. 24, pp. 11478-11482 (Dec. 1993).
Gach et al., "HIV-1-Specific Antibody Response and Function after DNA Prime and Recombinant Adenovirus 5 Boost HIV Vaccine in HIV-Infected Subjects", PLOS One, vol. 11, No. 8, pp. 17 (Aug. 2016).
Gallo et al, "The HIV Env-mediated Fusion Reaction," Biochemics et Biophysica Acta, pp. 36-50 (2003).
Gallo, "The End or the Beginning of the Drive to an HIV-Preventive Vaccine: A View from over 20 Years", The Lancet, vol. 366, No. 9500, pp. 1894-1898 (Nov. 2005).

Gao et al, "A Comprehensive Panel of Near-Full-Length Clones and Reference Sequences for Non-Subtype B Isolates of Human Immunodeficiency Virus Type 1, "Journal of Virology, vol. 72, No. 7, pp. 5680-5698 (1998).
Gao et al, "Antigenicity and Immunogenicity of a Synthetic Human Immunodeficiency Virus Type 1 Group M Consensus Envelope Glycoprotein," Journal of Virology, vol. 79, No. 2, pp. 1154-1163 (Jan. 2005).
Gao et al, "Centralized HIV-1 Envelope Immunogens and Neutralizing Antibodies," Current HIV Research, vol. 5, No. 6, pp. 572-577 (2007).
Gao et al, "Molecular Cloning and Analysis of Functional Envelope Genes from Human Immunodeficiency Virus Type 1 Sequence Subtypes a through G" Journal of Virology, vol. 70, No. 3, pp. 1651-1667 (Mar. 1996).
Gaschen et al, "Diversity Consideration in HIV-1 Vaccine Selection," Science, vol. 296, No. 5577, pp. 2354-2360 (Jun. 28, 2002).
Genbank Accession No. AF286227.1, "HIV-1 strain 97Za012 from South Africa, complete genome." Accessed Jan. 6, 2016.
GenBank Accession No. KC769514. Retrieved on Dec. 30, 2014 (2 pages).
Georgiev et al, "Delineating Antibody Recognition in Polyclonal Sera from Patterns of HIV-1 Isolate Neutralization," Science, vol. 340, No. 6133, pp. 751-756 (2013).
Georgiev et al, "Single-Chain Soluble BG505.SOSIP gp140 Trimers As Structural And Antigenic Mimics Of Mature Closed HIV-1 Env," Journal of Virology, vol. 89, pp. 5318-5329 (2015).
Gianella et al., "Effect of Early Antiretroviral Therapy During Primary HIV-1 Infection on Cell-Associated HIV-1 DNA and Plasma HIV-1 RNA", Antiviral Therapy, vol. 16, No. 4, pp. 535-545 (2011).
Girard et al., A Review of Vaccine Research and Development: The Human Immunodeficiency Virus (HIV), Vaccine, vol. 24, pp. 4062-4081 (2006).
Gomez-Roman et al., "An Adenovirus-Based HIV Subtype B Prime/Boost Vaccine Regimen Elicits Antibodies Mediating Broad Antibody-Dependent Cellular Cytotoxicity Against Non-Subtype B HIV Strains", J. Acquir. Immune Defic. Syndr., vol. 43, No. 3, pp. 270-277 (Nov. 2006).
Gotch et al., "Candidate Vaccines for Immunotherapy in HIV", HIV Medicine, vol. 2, pp. 260-265 (2001).
Goujard et al., "HIV-1 Control After Transient Antiretroviral Treatment Initiated in Primary Infection: Role of Patient characteristics and Effect of Therapy", Antiviral Therapy, vol. 17, No. 6, pp 1001-1009 (2012).
Graham et al, "Phase 1 Safety and Immunogenicity Evaluation of a Multiclade HIV-1 DNA Candidate Vaccine," The Journal of Infectious Diseases, vol. 194, No. 12, pp. 1650-1660 (Dec. 15, 2006).
Gray et al, "Isolation of a Monoclonal Antibody That Targets the Alpha-2 Helix of gp120 and Represents the Initial Autologous Neutralizing-Antibody Response in an HIV-1 Subtype C-Infected Individual," Journal of Virology, vol. 85, No. 15, pp. 7719-7729 (Aug. 2011).
Gray et al., "Safety and Efficacy of the HVTN 503/Phambili Study of a Clade-B-based HIV-1 Vaccine in South Africa: A Double-Blind, Randomised, Placebo-Controlled Test-of-Concept Phase 2b Study", Lancet Infect Dis, vol. 11, No. 7, pp. 507-515 (2011).
Grundner et al, "Analysis of the Neutralizing Antibody Response Elicited in Rabbits by Repeated Inoculation with Trimeric HIV-1 Envelope Glycoproteins," Virology, vol. 331, No. 1, pp. 33-46 (2005).
Guenaga et al, "Glycine Substitution At Helix-To-Coil Transitions Facilitates The Structural Determination Of A Stabilized Subtype C HIV Envelope Glycoprotein," Immunity, vol. 46, pp. 792-803 (2017).
Gurwith et al, "Safety and Immunogenicity of an Oral, Replicating Adenovirus Serotype 4 Vector Vaccine for H5N1 Influenza: A Randomised, Double-Blind, Placebo-Controlled, Phase 1 Study", Lancet Infect Dis, vol. 13, No. 3, pp. 238-250 (2013).
Hamlyn et al., "Plasma HIV Viral Rebound Following Protocol-Indicated Cessation of ART Commenced in Primary and Chronic HIV Infection", PLOS One, vol. 7, No. 8, 8 pgs (Aug. 2012).

(56) References Cited

OTHER PUBLICATIONS

Hammer et al, "Efficacy Trial of a DNA/rAd5 HIV-1 Preventive Vaccine," The New England Journal of Medicine, vol. 369, No. 22, pp. 2083-2092 (Nov. 28, 2013).
Haslett et al., "Strong Human Immunodeficiency Virus (HIV)-Specific CD4+ T Cell Responses in a Cohort of Chronically Infected Patients are Associated with Interruptions in Anti-HIV Chemotherapy," J. Infect. Dis, vol. 81, No. 1, pp. 1264-1272 (2000).
Havenga et al., "Novel Replication-Incompetent Adenoviral B-Group Vectors: High Vector Stability and Yield in PER. C6 Cells", Journ. of Gen Viro., vol. 87, pp. 2135-2143 (2006).
Haynes et al, "Immune-Correlates Analysis of an HIV-1 Vaccine Efficacy Trial," The New England Journal of Medicine, vol. 366, No. 14, pp. 1275-1286 (2012).
He et al, "Presenting Native-Like Trimeric HIV-1 Antigens With Self-Assembling Nanoparticles," Nature Communications, vol. 7, No. 1, pp. 1-15 (2016).
Hierholzer et al., "Adenoviruses from Patients with AIDS: A Plethora of Serotypes and a Description of Five New Serotypes of Subgenus D (types 43-47).", J. Infect. Dis., vol. 158, No. 4 pp. 804-813 (1988).
Huang et al, "Broad and Potent Neutralization of HIV-1 by a gp41-Specific Human Antibody," Nature, vol. 491, No. 7424, pp. 406-412 (2012).
Int'l Preliminary Report on Patentability and Written Opinion dated May 24, 2011 in Int'l Application No. PCT/US2009/064999.
Int'l Preliminary Report on Patentability dated Jan. 26, 2017 in Int'l Application No. PCT/US2015/51891.
"Endogenous Retrovirus Group K Member 25 Env Polyprotein", Database UNIPROT, Accession No. Q5GI17, 2 pages (Mar. 1, 2005).
"GCN4 Fusion Linker Peptide, SEQ ID No. 3," Database Geneseq, Accession No. AEN61500, 1 page (Mar. 8, 2007).
"Recombinant Protein gp41 Heterologous Transmembrane Region, SEQ ID1," Database Geneseq, Accession No. AUR74751, 1 page, (Mar. 19, 2009).
"Transmembrane Domain Peptide, SEQ ID 14," Database Geneseq, Accession No. AEF06609, 1 page (Mar. 23, 2006).
Abrahams et al, "Quantitating the Multiplicity of Infection with Human Immunodeficiency Virus Type 1 Subtype C Reveals a Non-Poisson Distribution of Transmitted Variants," Journal of Virology, vol. 83, No. 8, pp. 3556-3567 (Apr. 2009).
Abrahamyan et al, "The Cytoplasmic Tail Slows the Folding of Human Immunodeficiency Virus Type 1 Env from a late Prebundle Configuration into the Six-Helix Bundle", Journal of Virology, vol. 79, No. 1, pp. 106-115 (2005).
Achenbach et al., "Effect of Therapeutic Intensification Followed by HIV DNA Prime AND rAd5 Boost Vaccination on HIV-specific Immunity and HIV Reservoir (EraMune 02): a Multicentre Randomised Clinical Trial", The Lancet, vol. 2, No. 3, pp. e82-e91 (Mar. 2015).
Altschul et al, "Gapped BLAST and PSI-BLAST: A New Generation Of Protein Database Search Programs," Nucleic Acids Research, vol. 25, No. 17, pp. 3389-3402 (1997).
Amanna et al, "Contributions of Humoral and Cellular Immunity to Vaccine-Induced Protection in Humans," Virology, vol. 411, No. 2, pp. 206-215 (2011).
Ambrosini et al., "Gene Transfer in Astrocytes: Comparison Between Different Delivering Methods and Expression of the HIV-1 Protein Net", J. Neurosci. Res., vol. 55, p. 569 (1999).
Baba et al, "Human Neutralizing Monoclonal Antibodies of the IgG1 Subtype Protect Against Mucosal Simian-Human Immunodeficiency Virus Infection," Nature Medicine, vol. 6, No. 2, pp. 200-206 (2000).
Baden et al., "First-in-human Evaluation of the Safety and Immunogenicity of a Recombinant Adenovirus Serotype 26 HIV-1 Env Vaccine (IPCAVD 001)", J. Infect. Dis., vol. 207, No. 2, pp. 240-247 (2013).
Bale et al, "Covalent Linkage Of HIV-1 Trimers To Synthetic Liposomes Elicits Improved B Cell And Antibody Responses," Journal of Virology, vol. 91, No. 16, pp. e00443-e004417 (2017).

Bangari et al., "Development of Nonhuman Adenoviruses as Vaccine Vectors", Vaccine, vol. 24, No. 7, pp. 849-26 (2006).
Barnett et al, "Development of V2-deleted trimeric envelope vaccine candidates from human immunodeficiency virus type 1 (HIV-1) subtypes Band C," Microbes Infect, vol. 7, vol. 14, pp. 1386-1391 (2005).
Barouch et al., "Characterization of Humoral and Cellular Immune Responses Elicited by a Recombinant Adenovirus Serotype 26 HIV-1 Env Vaccine in Healthy Adults (IPCAVD 001)", J. Infect. Dis, vol. 207, No. 2, pp. 248-256 (2013).
Barouch et al., "International Seroepidemiology of Adenovirus Serotypes 5, 36, 35 and 48 in Pediatric and Adult Populations", Vaccine, vol. 29: pp. 5203-5209 (2011).
Barouch, "Challenges in the Development of an HIV-1 Vaccine", Nature, vol. 455, No. 2, pp. 613-619 (2008).
Beddows et al, "A Comparative Immunogenicity Study in Rabbits of Disulfide-Stablized, Proteolytically Cleaved, Soluble Trimeric Human Immunodeficiency Virus Type 1 gp140, Trimeric Cleavage-Defective gp140 and Monomeric jp120," Virology, vol. 360, pp. 329-340 (2007).
Berger et al, "Chemokine Receptors as HIV-1 Coreceptors: Roles in Viral Entry, Tropism and Disease," Annu. Rev. Immunol., vol. 17, pp. 657-700 (1999).
Berman et al, "Comparison of the Immune Response to Recombinant gp120 in Humans and Chimpanzees," AIDS, vol. 8, pp. 591-601 (1994).
Binley et al "A Recombinant Human Immunodeficiency Virus Type 1 Envelope Glycoprotein Complex Stabilized by 6 an Intermolecular Disulfide Bond Between the gp120 and gp41 Subunits is an Antigenic Mimic of the Trimeric Virion-Associated Structure," Journal of Virology, vol. 74, No. 2, pp. 627-643 (Jan. 2000).
Blanchard et al., "Modified Vaccinia Virus Ankara Undergoes Limited Replication in Human Cells and Lacks Several Immunomodulatory Proteins: Implications for Use as a Human Vaccine", Journ. of Gen. Viro., vol. 79, pp. 1159-1167 (1998).
Blondelle et al., "Immunogenically Optimized Peptides Derived from Natural Mutants of HIV CTL Epitopes and Peptide Combinational Libraries", Biopolymers, vol. 90(5), pp. 683-694 (2008).
Bower et al, "Elicitation of Neutralizing Antibodies with DNA Vaccines Expressing Soluble Stabilized Human Immunodefiency Virus Type 1 Envelope Glycoprotein Trimers Conjugated to C3d", Journ. of Viro., vol. 78, No. 9, pp. 4710-4719 (May 2004).
Bower et al, "HIV-1 ENV gp 140 Trimers Elicit Neutralizing Antibodies Without Efficient Induction of Conformational Antibodies," Vaccine, vol. 24, pp. 5442-5451 (2006).
Buchbinder et al., Efficacy Assessment of a Cell-Mediated Immunity HIV-1 Vaccine (The Step Study): A Double-Blind, Randomised, Placebo-Controlled, Test-of-Concept Trial, Lancet, vol. 372 No. 9653, pp. 1881-1893 (2008).
Burke et al. "Neutralizing Antibody Responses to Subtype B and C Adjuvanted HIV Envelope Protein Vaccination in Rabbits," Virology, vol. 387, No. 1, pp. 147-156 (Apr. 2009).
Burton et al, "HIV Vaccine Design and the Neutralizing Antibody Problem," Nature Immunology, vol. 5, No. 3, pp. 233-236 (Mar. 2004).
Calarese et al, "Antibody Domain Exchange is an Immunological Solution to Carbohydrate Cluster Recognition," Science, vol. 300, No. 5628, pp. 2065-2071 (2003).
Carcelain et al., "Immune Interventions in HIV Infection", Immunol Rev., vol. 254, No. 1, pp. 355-371 (2013).
Cardoso et al, "Broadly Neutralizing Anti-HIV Antibody 4E10 Recognizes a Helical Conformation of a Highly Conserved Fusion-Associated Motif in gp41," Immunity, vol. 22, No. 2, pp. 163-173 (Feb. 2005).
Cardoso et al, "Structural Basis of Enhanced Binding of Extended and Helically Constrained Peptide Epitopes of the Broadly Neutralizing HIV-1 Antibody 4E1 0," Journal of Molecular Biology, vol. 365, No. 5, pp. 1533-1544 (2007).
Carroll et al., "Host Range and Cytopathogenicity of the Highly Attenuated MVA Strain of Vaccinia Virus: Propagation and Generation of Recombinant Viruses in a Nonhuman Mammalian Cell Line", Virology, vol. 238, pp. 198-211 (1997).

(56) References Cited

OTHER PUBLICATIONS

Carrow et al, "High Prevalance of Antibodies to the gp120 V3 Regional Principal Neutralizing Determinant of HIV-1 MN in Sera from Africa and the Americas," Aids Research and Human Retroviruses, vol. 7, No. 10, pp. 831-838 (1991).
Catanzaro et al, "Phase I Clinical Evaluation of a Six-Plasmid Multiclade HIV-1 DNA Candidate Vaccine," Vaccine, vol. 25, No. 20, pp. 4085-4092 (2007).
Centlivre et al., "In HIV-1 Pathogenesis the Die is Cast During Primary Infections", AIDS, vol. 21, No. 1, pp. 1-11 (2007).
Checkley et al, "HIV-1 Envelope Glycoprotein Biosynthesis, Trafficking, and Incorporation," Journal of Molecular Biology, vol. 410, No. 4, pp. 582-608 (2011).
Chen et al, "Expression, Purification, and Characterization of gp160e, the Soluble, Trimeric Ectodomain of the Simian Immunodeficiency Virus Envelope Glycoprotein, gp160," The Journal of Biological Chemistry, vol. 275, No. 45, pp. 34946-34953 (Nov. 10, 2000).
Chen et al., A Chimeric Protein of Simian Immunodeficiency Virus Envelope Glycoprotein gp140 and *Escherichia coli* Asparatate Transcarbamoylase, J. Virol, vol. 78, No. 9, pp. 4508-4516 (2004).
Chen et al., "Adenovirus-Based Vaccines: Comparison of Vectors from Three Species of Adenoviridae", J. Virol, vol. 34, No. 20, pp. 10522-10532 (2010).
Chen et al., "Protection of Rhesus Macaques Against Disease Progression from Pathogenic SHIV-89.6PD by Vaccination with Phage-Displayed HIV-1 Epitopes", Nat. Med., vol. 7, No. 11, pp. 1225-1231 (2001).
Cho et al, "Polyvalent Envelope Glycoprotein Vaccine Elicits a Broader Neutralizing Antibody Response But is Unable to Provide Sterilizing Protection Against Heterologous Simian/Human Immunodeficiency Virus Infection in Pigtailed Macaques," Journal of Virology, vol. 75, No. 5, pp. 2224-2234 (Mar. 2001).
Cohen et al, "Chimpanzee Adenovirus CV-68 Adapted as a Gene Delivery Vector Interacts with the Coxsackievirus and Adenovirus Receptor", J. Gen. Virol., vol. 83, pp. 151-155 (2002).
Cohen, "Did Merck's Failed HIV Vaccine Cause Harm?" Science, vol. 318, pp. 1048-1049 (2007).
Cohen, "Naked DNA Points Way to Vaccines," Science, vol. 259, pp. 1691-1692 (Mar. 1993).
Crooks et al, "A Comparative Immunogenicity Study of HIV-1 Virus-Like Particles Bearing Various Forms of Envelope Proteins, Particles Bearing No Envelope and Soluble Monomeric gp120," ScienceDirect, Virology vol. 366, pp. 245-262 (2007).
Davenport et al, "Binding Interactions Between Soluble HIV Envelope Glycoproteins and Quaternary-Structure-Specific Monoclonal Antibodies PG9 and PG16," Journal of Virology, vol. 85, No. 14, pp. 7095-7107 (Jul. 2011).
De Gruijl et al., Intradermal Delivery of Adenoviral Type-35 Vectors Leads to High Efficiency Transduction of Mature, CD8-+ T Cell-Stimulating Skin-Emigrated Dendritic Cells, J. Immunol, vol. 177, No. 4, pp. 2208-2215 (2006).
De Taeye et al, "Immunogenicity of Stabilized HIV-1 Envelope Trimers With Reduced Exposure of Non-Neutralizing Epitopes," Cell, vol. 163, pp. 1702-1715 (2015).
Abbink et al., "Comparative Seroprevalence and Immunogenicity of Six Rare Serotype Recombinant Adenovirus Vaccine Vectors from Subgroups B and D", Journ. of Virology, vol. 81, No. 9, pp. 4654-4663 (May 2007).
Baicu et al., "Acid-base Buffering in Organ Preservation Solutions as a Function of Temperature: New Parameters for Comparing Buffer Capacity and Effciency", Cryobiology, vol. 45, pp. 33-48 (2002).
Barouch et al., "Mosaic HIV-1 Vaccines Expand the Breadth and Depth of Cellular Immune Responses in Rhesus Monkeys", Nat. Med., vol. 16, No. 3, pp. 319-323 (2010).
Barouch et al., "Protective Efficacy of Adenovirus/Protein Vaccines Against SIV Challenges in Rhesus Monkeys", Science, vol. 349, No. 6245, pp. 320-324 (Jul. 2015).

Barouch et al., "Protective Efficacy of a Global HIV-1 Mosaic Vaccine against Heterologous SHIV Challenges in Rhesus Monkeys", Cell, vol. 155, pp. 531-539 (Oct. 2013).
Harris et al., "Trimeric HIV-1 Glycoprotein gp140 Immunogens and Native HIV-1 Envelope Glycoproteins Display the Same Closed and Open Quaternary Molecular Architectures", Proc. Natl Acad Sci., vol. 108, No. 28. pp. 11440-11445 (Jul. 2011).
Hoganson et al., "Development of a Stable Adenoviral Vector Formulation", BioProcessing Journ., pp. 43-48 (Mar. 2002).
Kamerzell et al., "Protein-Excipient Interactions: Mechanisms and Biophysical Characterization Applied to Protein Formulation Development", Advanced Drug Delivery Reviews, vol. 63, pp. 1118-1159 (2011).
Kovacs et al., "HIV-1 Envelope Trimer Elicits more Potent Neutralizing Antibody Responses than Monomeric gp120", Proc. Natl. Acac. Sci., vol. 109, No. 30, pp. 12111-12116 (2012).
Lepe-Zuniga et al., "Toxicity of Light-Exposed Hepes Media", Journ. of Immun Methods, vol. 103, pp. 145 (1987).
Sanders et al., "Stabilization of the Soluble, Cleaved, Trimeric Form of the Envelope Glycoprotein Complex of Human Immunodeficiency Virus Type 1", Journ. of Viro., vol. 76, No. 17, pp. 8875-8889 (Sep. 2002).
Sanders et al., "Brunenders: A Partially Attenuated Historic Poliovirus Type 1 Vaccine Strain", Journ. of General Viro., vol. 96, pp. 2614-2622 (2015).
Zhang et al., "Expression, Purification, and Characterization of Recombinant HIV gp140", Journ of Bio Chem., vol. 276, No. 43, pp. 39577-39585 (2001).
Nikolola et al., "Breadth of Neutralizing Antibodies Elicited by Stable, Homogeneous Clade A and Clade C HIV-1 gp140 Envelope Trimers in Guinea Pigs", Journ. of Viro., vol. 84. No. 7, pp. 3270-3279 (Apr. 2010).
Nikolola et al., "Characterization and Immunogenicity of a Novel Mosaic M HIV-1 gp140 Trimer", Journ. of Virology, vol. 88, No. 17, pp. 9538-9552 (Sep. 2014).
Uchiyama, "Liquid Formulation for Antibody Drugs", Biochimica Biophysica Acta, vol. 1844, pp. 2041-2052 (2014).
Zigler et al., "Analysis of the Cytotoxic Effects of Light-Exposed Hepes-Containing Culture Medium", In Vitro Cell Dev. Biol., vol. 21, No. 5, pp. 282-287 (1985).
Int'l Preliminary Report on Patentability dated Apr. 5, 2016 in Int'l Application No. PCT/US2014/059093.
Int'l Preliminary Report on Patentability dated Jul. 7, 2015 in Int'l Application No. PCT/US2014/010543.
Int'l Preliminary Search Report on Patentability dated Apr. 12, 2011 in Int'l Application No. PCT/US2009/060494.
Int'l Search Report and Written Opinion dated Jan. 22, 2015 in Int'l Patent Application No. PCT/US2014/059093.
Int'l Search Report and Written Opinion dated Feb. 5, 2016 in Int'l Application No. PCT/US2015/051891.
Int'l Search Report and Written Opinion dated Apr. 23, 2010 in Int'l Application No. PCT/US2009/060494.
Int'l Search Report and Written Opinion dated Nov. 6, 2017 in Int'l Application No. PCT/US2017/049817.
Int'l Search Report dated Mar. 5, 2010 in Int'l Application No. PCT/US2009/064999.
Int'l Search Report dated Mar. 21, 2014 in Int'l Application No. PCT/US2014/010543.
Janes et al., "MRKAd5 HIV-1 Gag/Pol/Nef Vaccine-Induced T-cell Responses Inadequately Predict Distance of Breakthrough HIV-1 Sequences to the Vaccine or Viral Load", PLoS One, vol. 7, No. 8, pp. e43396 (2012).
Jeffs et al, "Expression and Characterization of Recombinant Oligomeric Envelope Glycoproteins Derived From Primary Isolates of HIV-1," Vaccine, vol. 22, No. 8, pp. 1032-1046 (2004).
Jin et al., "Stabilizing Formulations for Inhalable Powders of an Adenovirus 35-Vectored Tuberculosis (TB) Vaccine (AERAS-402)", Vaccine, vol. 28, No. 27, pp. 4369-4375 (2010).
Julien et al, "Asymmetric Recognition of the HIV-1 Trimer by Broadly Neutralizing Antibody PG9," Proceedings of the National Academy of Sciences of the United States of America, vol. 110, No. 11, pp. 4351-4356 (Mar. 12, 2013).

(56) References Cited

OTHER PUBLICATIONS

Julien et al, "Broadly Neutralizing Antibody PGT121 Allosterically Modulates CD4 Binding via Recognition of the HIV-1 gp120 V3 Base and Multiple Surrounding Glycans," PLOS Pathogens, vol. 9, No. 5, pp. e1003342 (May 2013).

Julien et al, "Design And Structure Of Two HIV-1 Clade C SOSIP. 664 Trimers That Increase The Arsenal Of Native-Like15 Env Immunogens," PNAS, vol. 112, No. 38, pp. 11947-11952 (2015).

Kang et al, "Structural and Immunogenicity Studies of a Cleaved, Stabilized Envelope Trimer Derived from Subtype A HIV-1," Vaccine, vol. 27, pp. 5120-5132 (2009).

Katlama et al., "Barriers to a Cure for HIV: New Ways to Target and Eradicate HIV-1 Reservoirs", The Lancet, vol. 381, No. 988., pp. 2109-2117 (Jun. 2013).

Kesavardhana et al, "Stabilizing The Native Trimer Of HIV-1 Env By Destabilizing The Heterodimeric Interface Of The gp41 Postfusion Six-Helix Bundle," Journal of Virology, vol. 88, No. 17, pp. 9590-9604 (2014).

Khoo et al., "Adenovirus Infections in Human Immunodeficiency Virus-Positive Patients: Clinical Features and Molecular Epidemiology", J. Infect. Dis, vol. 172, No. 3, pp. 629-637 (1995).

Kim et al, "Comparison of HIV Type 1 ADA gp120 Monomers Versus gp140 Trimers as Immunogens for the Induction of Neutralizing Antibodies," AIDS Research and Human Retroviruses, vol. 21, No. 1, pp. 58-67 (2005).

Kobinger et al, "Chimpanzee Adenovirus Vaccine Protects Against Zaire Ebola Virus", Virology, vol. 346, pp. 394-401 (2006).

Kochanek et al, "A New Adenoviral Vector: Replacement of All Viral Coding Sequences with 28 kb of DNA Independently Expressing Both Full-Length Dystrophin and Beta-Galactosidase," Proceedings of the National Academy of Sciences of the United States of America, vol. 93, No. 12, pp. 5731-5736 (Jun. 1996).

Kong et al, "Uncleaved Prefusion-Optimized gp140 Trimers Derived From Analysis Of HIV-1 Envelope Metastability," Nature Communications, vol. 7, No. 1, pp. 1-15 (2016).

Kong et al., "Expanded Breadth of the T-Cell Response to Mosaic Human Immunodeficiency Virus Type 1 Envelope DNA Vaccination," J. Viral., vol. 83, No. 5, pp. 2201-2215 (2009).

Korber et al., "T-Cell Vaccine Strategies for Human Immunodeficiency Virus, The Virus with a Thousand Faces," J. Viral., vol. 83, No. 17, pp. 8300-8314 (2009).

Kothe et al, "Ancestral and Consensus Envelope Immunogens for HIV-1 Subtype C," Virology, vol. 352, No. 2, pp. 438-449 (2006).

Kothe et al, "Antigenicity and Immunogenicity of HIV-1 Consensus Subtype B Envelope Glycoproteins," Virology, vol. 360, No. 1, pp. 218-234 (Mar. 30, 2007).

Kuschner et al., "A Phase 3, Randomized, Double-Blind, Placebo-Controlled Study of the Safety and Efficacy of the Live, Oral Adenovirus Type 4 and Type 7 Vaccine, in U.S. Military Recruits", Vaccine, vol. 31(28), pp. 2963-2971 (2013).

Kushnir et al, "Virus-Like Particles As A Highly Efficient Vaccine Platform: Diversity Of Targets And Production Systems And Advances In Clinical Development," Vaccine, vol. 31, pp. 58-83 (2012).

Kwon et al, "Crystal Structure, Conformational Fixation and Entry-Related Interactions Of Mature Ligand-Free HIV-1 ENV," Nature Structural & Molecular Biology, vol. 22, No. 7, pp. 522-531 (2015).

Kwong et al, "Structure of an HIV gp120 Envelope Glycoprotein in Complex with the CD4 Receptor and a Neutralizing Human Antibody," Nature, vol. 393, No. 6686, pp. 648-659 (Jun. 18, 1998).

Lasaro et al., "New Insights on Adenovirus as Vaccine Vectors", Mol. Ther., vol. 17, No. 8, pp. 1333-1339 (2009).

Lee et al, "A Single Point Mutation in HIV-1 V3 Loop Alters the Immunogenic Properties of rgp120," Archives of Virology, vol. 145, pp. 2087-2103 (2000).

Letvin et al., "Potent, Protective Anti-HIV Immune Responses Generated by Bimodal HIV Envelope DNA Plus Protein Vaccination", Proc. Natl. Acad. Sci., vol. 94, pp. 9378-9383 (1997).

Levine, "Why Do We Not Yet Have a Human Immunodeficiency Virus Vaccine," J. Virol., vol. 82, No. 24, pp. 11998-12000 (Dec. 2008).

Li et al, "Broad HIV-1 Neutralization Mediated by CD4-Binding Site Antibodies," Nature Medicine, vol. 13, No. 9, pp. 1032-1039 (Sep. 2007).

Li et al, "Characterization of Antibody Responses Elicited by Human Immunodeficiency Virus Type 1 Primary Isolate Trimeric and Monomeric Envelope Glycoproteins in Selected Adjuvants," Journal of Virology, vol. 80, No. 3, pp. 1414-1426 (Feb. 2006).

Li et al, "Evidence for Potent Autologous Neutralizing Antibody Titers and Compact Envelopes in Early Infection with Subtype C Human Immunodeficiency Virus Type 1," Journal of Virology, vol. 80, No. 11, pp. 5211-5218 (Jun. 2006).

Li et al, "Human Immunodeficiency Virus Type 1 env Clones from Acute and Early Subtype B Infections for Standardized Assessments of Vaccine-Elicited Neutralizing Antibodies," Journal of Virology, vol. 79, No. 16, pp. 10108-10125 (Aug. 2005).

Li et al, "Removal of a Single N-Linked Glycan in Human Immunodeficiency Virus Type 1 gp120 Results in an Enhanced Ability to Induce Neutralizing Antibody Responses," Journal of Virology, vol. 82, No. 2, pp. 638-651 (Jan. 2008).

Li et al, "Visualizing Antigen-Specific and Infected Cells in Situ Predicts Outcomes in Early Viral Infection", Science, vol. 323, No. 5922, pp. 1726-1729 (2009).

Lian et al., "Evaluation of Envelope Vaccines Derived from the South African Subtype C Human Immunodeficiency Virus Type 1 TV1 Strain," Journal of Virology, vol. 79, No. 21, pp. 13338-13349 (Nov. 2005).

Liao et al, "A Group M Consensus Envelope Glycoprotein Induces Antibodies That Neutralize Subsets of Subtype B and C HIV-1 Primary Viruses," Virology, vol. 353, No. 2, pp. 268-282 (Sep. 30, 2006).

Liao et al, "Antigenicity and Immunogenicity of Transmitted/Founder, Consensus, and Chronic Envelope Glycoproteins of Human Immunodeficiency Virus Type 1," Journal of Virology, vol. 87, No. 8, pp. 4185-4201 (Apr. 2013).

Liao et al, "Co-Evolution of a Broadly Neutralizing HIV-1 Antibody and Founder Virus," Nature, vol. 496, No. 7446, pp. 469-476 (Apr. 25, 2013).

Lin et al, "Designing Immunogens to Elicit Broadly Neutralizing Antibodies to the HIV-1 Envelope Glycoprotein," Current HIV Research, vol. 5, No. 6, pp. 514-541 (2007).

Liu et al., "Magnitude and Phenotype of Cellular Immune Responses Elicited by Recombinant Adenovirus Vectors and Heterologous Prime-Boost Regimens in Rhesus Monkeys", J. Viol., vol. 82, No. 10, pp. 4844-4852 (2008).

Liu et al., Immune Control of an SIV Challenge by a T-Cell-Based Vaccine in Rhesus Monkeys, Nature, vol. 457, No. 7225, pp. 87-91(2009).

Li et al, "Genetic and Neutralization Properties of Subtype C Human Immunodeficiency Virus Type 1 Molecular env Clones From Acute Early Heterosexually Acquired Infections in Southern Africa," Journal of Virology, vol. 80, No. 23, 11776-11790 (Dec. 2006).

* cited by examiner

HIV VACCINE FORMULATION

CROSS-REFERENCE TO RELATED APPLICATIONS

This application is entitled to priority pursuant to 35 U.S.C. § 119(e) to U.S. Provisional Application No. 62/350,919, filed on Jun. 16, 2016, which is incorporated by reference herein in its entirety.

REFERENCE TO SEQUENCE LISTING SUBMITTED ELECTRONICALLY

This application contains a sequence listing, which is submitted electronically via EFS-Web as an ASCII formatted sequence listing with a file name "688097_115U1_Sequence Listing," creation date of Jun. 13, 2017, and having a size of 80.3 kb. The sequence listing submitted via EFS-Web is part of the specification and is herein incorporated by reference in its entirety.

BACKGROUND OF THE INVENTION

Human Immunodeficiency Virus (HIV) affects millions of people worldwide, and the prevention of HIV through an efficacious vaccine remains a very high priority, even in an era of widespread antiretroviral treatment. HIV-1 is the most common and pathogenic strain of the virus, with more than 90% of HIV/AIDS cases deriving from infection with HIV-1 group M. The M group is subdivided further into clades or subtypes. An efficacious vaccine ideally would be capable of eliciting both potent cellular responses and broadly neutralizing antibodies capable of neutralizing HIV-1 strains from different clades.

The high genetic variability of HIV-1 makes the development of a HIV-1 vaccine an unprecedented challenge. In order to improve coverage of potential T-cell epitopes, and improve cellular responses, "mosaic" HIV-1 Gag, Pol and Env antigens, derived from HIV Group Antigen (Gag), Polymerase (Pol), and Envelope (Env) proteins, were described by others and developed in an attempt to provide maximal coverage of potential T-cell epitopes (e.g., Barouch et al, *Nat Med* 2010, 16: 319-323). The mosaic antigens are similar in length and domain structure to wild-type, naturally occurring HIV-1 antigens.

Sequences encoding mosaic antigens have been cloned in vectors, for example, such as recombinant adenovirus serotype 26 (rAd26), and these recombinant vectors have been used in vaccines to generate immune responses against HIV (see e.g. Barouch et al, supra; and WO 2010/059732). Viral vectors expressing such mosaic HIV antigens have proven to be effective in eliciting an immune response against HIV infection.

Another therapeutic strategy that has been explored for inducing immune responses against HIV is the use of trimeric HIV envelope proteins as immunogens in vaccines, such as gp140. The native envelope spike on the surface of HIV is trimeric. Examples of trimeric envelope proteins include clade C gp140 protein, and a mosaic envelope trimer protein, such as those disclosed in WO 2014/042942 and WO 2014/107744.

Clade C gp140 protein has previously been described e.g. in WO 2010/042942 and in Nkolola et al. 2010, but there was no focus on any pharmaceutical formulation work in those disclosures. The protein was in phosphate-buffered saline (PBS) in some of the experiments in those disclosures. Mosaic gp140 has been described previously e.g. in WO 2014/107744 and in Nkolola et al 2014, but again there was no focus on any pharmaceutical formulation work in those disclosures. The protein was in 25 mM Tris pH 7.5 and 150 mM NaCl in some of the experiments in those disclosures.

Trimeric HIV envelope proteins, such as gp140, are capable of inducing potent immune responses. Such envelope proteins can also be administered in combination with other HIV antigens, such as mosaic antigens, to provide enhanced immunity against HIV. However, the stability of the HIV envelope proteins as trimers is not optimal under conditions typically used for clinical and commercial manufacturing. The trimeric HIV envelope proteins are susceptible to both chemical and physical degradation. Moreover, many different factors, such as the buffer formulation, can affect the stability of proteins, and the effects are often unpredictable. For example, the use of HEPES buffer in protein formulations has been shown to result in generation of hydrogen peroxide when exposed to ambient light during the manufacturing process, which can impact the stability of the protein as well as other components in the formulation, such as surfactants. See, e.g., Baicu et al. *Cryobiology* (2002) 45(1) 33-48; Lepe-Zuniga et al. *J. Immunol. Methods* (1987) 103(1), 145; and Zigler et al. In *Vitro Cell. Dev. Biol.* (1985) 21(5), 282-287. It is desirable to have an HIV vaccine gp140 formulation that would be suitable for stability of different variants of gp140 protein, such as Clade C or mosaic gp140, and preferably with Aluminum Phosphate adjuvant as a single vial drug product (rather than being entirely dependent upon pharmacy mixing immediately prior to delivery of the vaccine), and in addition would enable drug product manufacturing meeting large late phase and commercial scale demands. It is generally unpredictable which combination of ingredients will result in a formulation that meets all these requirements.

Accordingly, there is a need in the art for improved formulations of HIV gp140 proteins with better stability under conditions used for clinical and commercial manufacturing in order to realize the full therapeutic potential of such trimeric envelope proteins. These formulations should also be compatible for use with additional HIV antigen(s), including vectors expressing HIV antigen(s), and/or adjuvants.

BRIEF SUMMARY OF THE INVENTION

The invention relates to immunogenic compositions of HIV gp140 proteins that have improved stability. The immunogenic compositions of the invention can be stored under refrigerated conditions for extended periods of time, and are more optimal for use in clinical and commercial manufacturing. The immunogenic compositions of the invention can also include an adjuvant. The invention also relates to methods of preparing the immunogenic compositions, and methods of using the immunogenic compositions to induce an immune response against HIV.

In one general aspect, the invention relates to an immunogenic composition comprising, relative to the total volume of the composition:
 a. 0.05 mg/mL to 5 mg/mL of an HIV gp140 protein;
 b. 2% to 15% (w/v) sorbitol;
 c. 0.01 to 0.05% (w/v) polysorbate 20; and
 d. 5 to 20 mM histidine buffer at a pH of 5.5 to 7.0.

Preferably, an immunogenic composition according to an embodiment of the invention comprises a stabilized trimeric HIV gp140 protein, such as an HIV gp140 protein comprising the amino acid sequence of SEQ ID NO: 1 or SEQ ID NO: 2.

In particular embodiments of the invention, the immunogenic composition comprises 0.2 mg/mL to 1 mg/mL of an HIV gp140 protein.

In particular embodiments, an immunogenic composition according to an embodiment of the invention comprises 5% (w/v) to 12% (w/v) sorbitol.

In particular embodiments, the immunogenic composition comprises 0.02% (w/v) polysorbate 20.

In particular embodiments, the immunogenic composition comprises 10 mM histidine buffer at a pH of 6.5.

According to embodiments of the invention, the immunogenic composition can further comprise an adjuvant, such as aluminum phosphate adjuvant. In certain of such embodiments, aluminum phosphate may be present in the composition at a concentration of 0.7-5.0 mg/mL, e.g. 0.8-4.0 mg/mL, e.g. 0.85 mg/mL, 1 mg/mL, 1.5 mg/mL, 2.0 mg/mL, 2.5 mg/mL, 3.0 mg/mL, 3.5 mg/mL, 3.84 mg/mL, 4.0 mg/mL. In certain embodiments, aluminum phosphate is present in the immunogenic compositions at a concentration of 0.85 mg/mL. In certain embodiments, aluminum phosphate is present in the immunogenic compositions at a concentration of 3.84 mg/mL.

In a preferred embodiment of the invention, an immunogenic composition comprises, relative to a total volume of the composition,
  a. 0.2 mg/mL to 1 mg/mL of an HIV gp140 protein comprising the amino acid sequence of SEQ ID NO: 1 or SEQ ID NO: 2
  b. 5% to 12% (w/v) sorbitol;
  c. 0.02% (w/v) polysorbate 20;
  d. 10 mM histidine buffer at a pH of 6.5; and
  e. aluminum phosphate adjuvant, preferably at a concentration of 0.7-4.0 mg/mL.

In another general aspect, the invention relates to a method of preparing an immunogenic composition comprising admixing:
  a. 0.05 mg/mL to 5 mg/mL of an HIV gp140 protein;
  b. 2% to 15% (w/v) sorbitol;
  c. 0.01 to 0.05% polysorbate 20; and
  d. 5 to 20 mM histidine buffer at a pH of 5.5 to 7.0;
to thereby obtain the immunogenic composition.

In certain embodiments, the immunogenic composition of the invention comprises aluminum phosphate adjuvant, preferably at a concentration of 0.7-4.0 mg/mL, and is stable upon storage at a temperature of 2-8° C., for at least one month, preferably at least 2, 3, 4, 5, 6 months, more preferably at least 7, 8, 9, 10, 11, 12 months, still more preferably at least 13, 14, 15, 16, 17, 18, 19, 20, 21, 22, 23, 24 months, most preferably at least 25, 26, 27, 28, 29, 30, 31, 32, 33, 34, 35, 36 months or longer, e.g. 1-72 months, e.g. 6-48 months, e.g. 12-36 months. In certain embodiments, the immunogenic composition of the invention comprises aluminum phosphate adjuvant, preferably at a concentration of 0.7-4.0 mg/mL, and is stable at a temperature of 25° C. for at least 6 months, e.g. 6-12 months, or 6-24 months. In certain embodiments, the immunogenic composition of the invention comprises aluminum phosphate adjuvant, preferably at a concentration of 0.7-4.0 mg/mL, and is stable at a temperature of 40° C. for at least 1 week, e.g. 1-12 weeks, e.g. at least 2 weeks, 3 weeks, 4 weeks, 1 month, e.g. 1-2 months, 1-3 months, or 3-6 months.

And in another general aspect, the invention relates to a method of inducing an immune response against a human immunodeficiency virus (HIV) in a subject in need thereof, comprising administering to the subject an effective amount of an immunogenic composition of the invention.

In a particular embodiment, a method of inducing an immune response against an HIV comprises administering to a subject in need thereof an immunogenic composition comprising, relative to the total volume of the composition,
  a. 0.2 mg/mL to 1 mg/mL of an HIV gp140 protein comprising the amino acid sequence of SEQ ID NO: 1 or SEQ ID NO: 2;
  b. 5% to 12% (w/v) sorbitol;
  c. 0.02% polysorbate 20;
  d. 10 mM histidine buffer at a pH of 6.5; and
  e. aluminum phosphate adjuvant, preferably at a concentration of 0.7-4.0 mg/mL.

In certain embodiments of the invention, a method of inducing an immune response against an HIV further comprises administering to the subject an effective amount of a second immunogenic composition comprising or encoding one or more additional HIV antigens, such as those comprising or encoding an amino acid sequence of SEQ ID NOs: 3-12. Preferably, the method comprises administering one or more vectors, preferably adenovirus 26 vectors, encoding one or more HIV antigens, such as those comprising an amino acid sequence of SEQ ID NOs: 3-12. Methods of inducing an immune response against an HIV can also comprise administering one or more MVA vectors encoding one or more HIV antigens, such as those comprising an amino acid sequence of SEQ ID NOs: 3-12. The one or more additional HIV antigens can also comprise SEQ ID NO: 11 having one or more mutations selected from the group consisting of (i) I529P (Ile to Pro at position 529), (ii) K480E (Lys to Glu at position 480), and (iii) a combination of EK479-480RRRR (i.e. replacing GluLys at position 479 and 480 by four consecutive Arg residues), I529P (Ile to Pro at position 529), A471C (Ala to Cys at position 471) and T575C (Thr to Cys at position 575). In one embodiment, the antigen comprising SEQ ID NO: 11 comprises SEQ ID NO: 12.

In another general aspect, the invention relates to a method for preparing a long-term, storage stable immunogenic composition that comprises HIV gp140 protein, the method comprising:
(i) admixing the following components to create an immunogenic composition comprising these components in amounts relative to the total volume of the composition:
  (a) 0.05 mg/mL to 5 mg/mL of an HIV gp140 protein;
  (b) 2% to 15% (w/v) sorbitol;
  (c) 0.01 to 0.05% (w/v) polysorbate 20; and
  (d) 5 to 20 mM histidine buffer at a pH of 5.5 to 7.0,
  (e) water,
  (f) aluminum phosphate adjuvant, preferably at a concentration of 0.7-4.0 mg/mL;
and
(ii) storing the composition at 2-8° C. for at least one month, e.g. 1-72 months, e.g. 6-48 months, e.g. 12-36 months.

BRIEF DESCRIPTION OF THE FIGURES

The foregoing summary, as well as the following detailed description of the invention, will be better understood when read in conjunction with the appended drawings. It should be understood that the invention is not limited to the precise embodiments shown in the drawings.

In the figures:

FIG. 1A shows the results of the SolvoVPE analysis; the change in absorbance at 350 nm (turbidity) is plotted against the change in absorbance at 280 nm (concentration); data points indicate the change between samples analyzed at time 0 ($T_0$) and after stressing the samples at 40° C. for 24 hours ($T_{24}$); SolvoVPE analysis was performed as described in Example 1;

FIG. 1B shows the results of the DLS analysis; the change in radius ($R_h$) from time 0 ($T_0$) at 20° C. to time 7 days ($T_{7\ days}$) at 70° C. is plotted by sugar (sucrose vs. sorbitol); DLS analysis was performed as described in Example 1;

FIG. 2A shows the relative amount (%) of hexamer and trimer species of HIV clade C gp40 protein in $T_0$ samples at different protein concentrations (0.2 mg/mL and 1.0 mg/mL);

FIG. 2B shows the relative amount (%) of hexamer and trimer species of HIV gp140 clade C protein in $T_0$ samples at different concentrations of surfactant (0.02% and 0.1%); the data shown is a combination of data collected from samples containing PS20 and samples containing PS80;

FIG. 2C shows the relative amount (%) of hexamer and trimer species of HIV clade C gp140 protein in $T_{24}$ samples at different protein concentrations (0.2 mg/mL and 1.0 mg/mL);

FIG. 2D shows the relative amount (%) of hexamer and trimer species of HIV gp140 clade C protein in $T_{24}$ samples at different concentrations of surfactant (0.02% and 0.1%); the data shown is a combination of data collected from samples containing PS20 and samples containing PS80;

FIG. 2E shows the relative amount (%) of low molecular weight species of HIV clade C gp140 protein based on surfactant type (PS20 versus PS80) in $T_0$ samples;

FIG. 2F shows the relative amount (%) of low molecular weight species of HIV gp140 clade C protein in $T_{24}$ samples at different concentrations of surfactant;

FIG. 3A shows the protein concentration after one, three, and five freeze-thaw cycles as determined by measuring the absorbance at 280 nm; and FIG. 3B shows the turbity of the tested formulations after one, three, and five freeze-thaw cycles as determined by measuring the absorbance at 350 nm.

FIG. 4A shows the relative protein concentration (%) of HIV clade C gp140 formulations stored at 25° C. and 60% RH without any aluminum phosphate adjuvant;

FIG. 4B shows the relative protein concentration (%) of HIV clade C gp140 formulations stored at 40° C. and 75% RH without any aluminum phosphate adjuvant;

FIG. 4C shows the relative protein concentration (%) of HIV clade C gp140 formulations stored at 25° C. and 60% RH with aluminum phosphate adjuvant.

DETAILED DESCRIPTION OF THE INVENTION

Figure 1A:
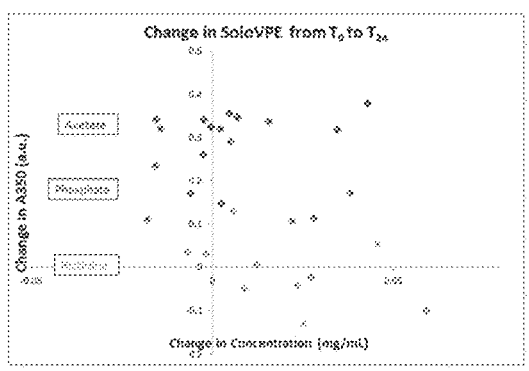
FIGS. 1A and 1B show the results of SolvoVPE analysis of HIV gp140 protein formulations prepared with acetate buffer, phosphate buffer, and histidine buffer, and dynamic light scattering (DLS) analysis of HIV gp140 protein formulations prepared with sorbitol and sucrose; in particular.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification. All patents, published patent applications and publications cited herein are incorporated by reference as if set forth fully herein. It must be noted that as used herein and in the appended claims, the singular forms "a," "an," and "the" include plural reference unless the context clearly dictates otherwise.

Unless otherwise stated, any numerical values, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

As used herein, "subject" means any animal, preferably a mammal, most preferably a human, to whom will be or has been administered an immunogenic composition according to embodiments of the invention. The term "mammal" as used herein, encompasses any mammal. Examples of mammals include, but are not limited to, mice, rats, rabbits, guinea pigs, monkeys, humans, etc., more preferably a human.

The invention generally relates to immunogenic compositions comprising HIV gp140 protein and optionally adjuvant, methods of preparing and storing such compositions, and methods of inducing an immune response against HIV in a subject with the immunogenic compositions, alone or in combination with one or more additional HIV antigens, which are preferably expressed by one or more vectors.

HIV Antigens

Human immunodeficiency virus (HIV) is a member of the genus Lentivirinae, which is part of the family of Retroviridae. Two species of HIV infect humans: HIV-1 and HIV-2. HIV-1 is the most common strain of HIV virus, and is known to be more pathogenic than HIV-2. As used herein, the terms "human immunodeficiency virus" and "HIV" refer to, but are not limited to, HIV-1 and HIV-2.

HIV is categorized into multiple clades with a high degree of genetic divergence. As used herein, the term "HIV clade" or "HIV subtype" refers to related human immunodeficiency viruses classified according to their degree of genetic similarity. There are currently three groups of HIV-1 isolates: M, N, and O. Group M (major strains) consists of at least ten clades, A through J. Group O (outer strains) can consist of a similar number of clades. Group N is a new HIV-1 isolate that has not been categorized in either group M or O.

As used herein, the terms "HIV antigen," "HIV antigenic protein," "HIV antigenic polypeptide," and "HIV immunogen" refer to a polypeptide capable of inducing an immune response, e.g., a humoral and/or cellular mediated response, against HIV in a subject. The HIV antigen can be a protein of HIV, a fragment or epitope thereof, or a combination of multiple HIV proteins or portions thereof, that can induce an immune response or produce an immunity, e.g., protective immunity, against HIV in a subject.

Preferably, an antigen is capable of raising in a host a protective immune response, e.g., inducing an immune response against a viral disease or infection, and/or producing an immunity in (i.e., vaccinating) a subject against a viral disease or infection, that protects the subject against the viral disease or infection. For example, the antigen can comprise a protein or fragments thereof from HIV, such as the HIV gag, pol and env gene products.

An HIV antigen can be any HIV-1 or HIV-2 antigen or fragment thereof. Examples of HIV antigens include, but are not limited to gag, pol, and env gene products, which encode structural proteins and essential enzymes. Gag, pol, and env gene products are synthesized as polyproteins, which are further processed into multiple other protein products. The primary protein product of the gag gene is the viral structural protein Gag polyprotein, which is further processed into MA, CA, SP1, NC, SP2, and P6 protein products. The pol gene encodes viral enzymes (Pol, polymerase), and the primary protein product is further processed into RT, RNase H, IN, and PR protein products. The env gene encodes structural proteins, specifically glycoproteins of the virion envelope. The primary protein product of the env gene is gp160, which is further processed into gp120 and gp41.

In certain embodiments, the HIV antigen comprises an HIV Gag, Env, or Pol antigen, or any antigenic portion or epitope or combination thereof, preferably an HIV-1 Gag, Env, or Pol antigen or any antigenic portion or epitope or combination thereof.

HIV antigens can also be mosaic HIV antigens. As used herein, "mosaic antigen" refers to a recombinant protein assembled from fragments of natural sequences. Mosaic antigens resemble natural antigens, but are optimized to maximize the coverage of potential T-cell epitopes found in the natural sequences, which improves the breadth and coverage of the immune response. Mosaic HIV antigens for use with the invention are preferably mosaic HIV-1 Gag, Pol, and/or Env antigens. Mosaic HIV Gag, Pol, and/or Env antigens are mosaic antigens comprising multiple epitopes derived from one or more of the Gag, Pol, and/or Env polyprotein sequences of HIV. For example, a mosaic Gag-Pol antigen comprises a mosaic Gag sequence and a mosaic Pol sequence.

Examples of mosaic HIV Gag, Pol, and/or Env antigens that can be used in the invention include those described in, e.g., US20120076812; Barouch et al., *Nat Med* 2010, 16:319-323; and Barouch et al., *Cell* 155:1-9, 2013, all of which are incorporated herein by reference in their entirety.

Preferably, mosaic HIV Gag, Pol, and/or Env antigens for use with the invention include, but are not limited to, mos1Env (SEQ ID NO: 3), mos2Env (SEQ ID NO: 4), mos1Pol (SEQ ID NO: 5), mos2Pol (SEQ ID NO: 6), mos1Gag (SEQ ID NO: 7), mos2Gag (SEQ ID NO: 8), and combinations thereof, for example mos1GagPol (SEQ ID NO: 9) and mos2GagPol (SEQ ID NO: 10). Other examples of mosaic HIV antigens include synthetic HIV Env proteins, which are non-naturally occurring HIV envelope proteins optimized to induce an immune response or provide an immunity against one or more naturally occurring HIV strains, such as that comprising SEQ ID NO: 11, or SEQ ID NO: 11 having one or more mutations selected from the group consisting of (i) I529P (Ile to Pro at position 529), (ii) K480E (Lys to Glu at position 480), and (iii) a combination of EK479-480RRRR (i.e. replacing GluLys at position 479 and 480 by four consecutive Arg residues), I529P (Ile to Pro at position 529), A471C (Ala to Cys at position 471) and T575C (Thr to Cys at position 575), or in preferred embodiments, the antigen comprising SEQ ID NO: 11 comprises the amino acid sequence of SEQ ID NO: 12, all as described in PCT/EP2016/081159 (filed on 15 Dec. 2016 in the name of Janssen Vaccines & Prevention B.V.), which is herein incorporated by reference in its entirety.

HIV gp140 Protein

As used herein, the term "HIV gp140 protein" refers to an uncleaved ectodomain of trimeric gp160 envelope protein, i.e., $(gp160)_3$. Embodiments of the invention relate to improved formulations of HIV gp140, preferably a trimer and/or hexamer of the gp140 subunits bound to the ectodomain of the gp41 subunits lacking the gp41 transmembrane and cytoplasmic segments. The HIV env gene encodes the precursor protein gp160, which is proteolytically cleaved into the two mature envelope glycoproteins gp120 and gp41. First, gp160 trimerizes to $(gp160)_3$ and then undergoes cleavage into the two noncovalently associated proteins gp120 and gp41 via a cleavage reaction mediated by a host cell protease, furin, at a sequence highly conserved in retroviral envelope glycoprotein precursors. Viral entry is subsequently mediated by a trimer of gp120/gp41 heterodimers. Gp120 is the receptor binding fragment, and binds to the CD4 receptor on a target cell that has such a receptor, such as, e.g., a T-helper cell. Gp41, which is non-covalently bound to gp120, is the fusion fragment and provides the second step by which HIV enters the cell. Gp41 is originally buried within the viral envelope, but when gp120 binds to a CD4 receptor, gp120 changes its conformation causing gp41 to become exposed, where it can assist in fusion with the host cell. HIV gp140 protein has been used as a surrogate for the native state of the cleaved, viral spike.

Expression of gp140 proteins has been described in several publications (e.g. Zhang et al., 2001; Sanders et al., 2002; Harris et al., 2011), and the protein can nowadays also be ordered from service providers, in different variants e.g. based on different HIV strains. A gp140 protein according to the invention can have a cleavage site mutation so that the gp120 domain and gp41 ectodomain are covalently linked, or alternatively the gp120 domain and gp41 ectodomain can be non-covalently linked (e.g. by a disulphur bridge as for instance in SOSIP variants). Gp140 proteins have been used in various vaccination experiments (e.g. Nkolola et al., 2010, 2014; Kovacs et al., 2012; Barouch et al., 2015; Sanders et al., 2015).

According to embodiments of the invention, the HIV gp140 protein can be a homotrimer (e.g., trimers comprising three identical polypeptide units), or a heterotrimer (e.g., trimers comprising three polypeptides that are not all identical). The HIV gp140 protein can also be a hexamer. Both trimer species and hexamer species of HIV gp140 protein have immunogenicity against HIV, or can induce immune responses against HIV in vivo. Preferably, the HIV gp140 protein is a trimer, and more preferably a homotrimer. An HIV gp140 protein can be a naturally occurring sequence, e.g., a sequence isolated from any HIV clade, such as clade A, clade B, clade C, etc., or a mosaic gp140 protein. A "mosaic gp140 protein" contains multiple epitopes derived from one or more gp140 sequences of one or more HIV clades.

Preferably, an HIV gp140 protein is a stabilized trimeric gp140 protein. A "stabilized trimeric gp140 protein" is a gp140 protein that can have or can be modified to include a polypeptide sequence, such as a trimerization domain, that increases the stability of the trimeric structure, or it can be a gp140 protein that is modified to contain mutations (as compared to natural gp140 sequences) that stabilize a trimeric structure, such as SOSIP and/or other mutations. Examples of trimerization domains include, but are not limited to, the T4-fibritin "foldon" trimerization domain, e.g., that having the amino acid sequence of GSGGYIPEAPRDGQAYVRKDGEWVLLSTFL (SEQ ID NO: 13); the coiled-coil trimerization domain derived from GCN4, e.g., that having the amino acid sequence of MKQIEDKIEEILSKIYHIENEIARIKKLIGEV (SEQ ID NO: 14); and the catalytic subunit of *E. coli* aspartate transcarbamoylase as a trimer tag. Such trimerization domains can be used to support stable trimer formation (see e.g. WO 2010/042942, Nkolola et al. 2010, WO 2014/107744, and Nkolola et al. 2014, for stabilized trimers of gp140 proteins). A stabilized trimeric gp140 protein for use in the invention can also include cleavage site mutations to enhance stability, e.g., in the furin cleavage sites, and/or so-called SOSIP mutations (see, e.g. Sanders et al., 2002, 2015). A stabilized trimeric gp140 protein can be derived from a gp140 protein isolated from any HIV clade, e.g., clade A, clade B, clade C, etc. A stabilized trimeric gp140 protein can also be a stabilized mosaic gp140 protein.

Exemplary HIV gp140 proteins that can be used in the invention include HIV clade C gp140 protein (SEQ ID NO: 1), HIV mosaic gp140 protein (SEQ ID NO: 2), and combinations thereof. Both the HIV clade C gp140 protein (SEQ ID NO: 1) and HIV mosaic gp140 protein (SEQ ID NO: 2) are stabilized trimeric gp140 proteins comprising a T4-fibritin "foldon" trimerization domain.

Immunogenic Compositions

In a first aspect, the invention relates to an immunogenic composition comprising an HIV gp140 protein. An "immunogenic composition" as used herein refers to a composition capable of inducing an immune response in a subject who has been or will be administered the composition. An immunogenic composition can be a vaccine. A "vaccine" refers to a composition that can provide protective immunity or a protective immune response to a subject, or that can be used to vaccinate a subject. According to embodiments of the invention, any HIV gp140 protein known in the art in view of the present disclosure can be used in an immunogenic composition of the invention. An immunogenic composition can comprise one or more HIV gp140 proteins, such as one, two, or three HIV gp140 proteins.

Preferably, the immunogenic composition of the invention comprises a stabilized trimeric gp140 protein. In one preferred embodiment, an HIV gp140 protein is an HIV clade C gp140 protein, such as that comprising the amino acid sequence of SEQ ID NO: 1. In another preferred embodiment, an HIV gp140 protein is a HIV mosaic gp140 protein, such as that comprising the amino acid sequence of SEQ ID NO: 2.

In other embodiments, an immunogenic composition comprises both an HIV clade C gp140 protein and an HIV mosaic gp140 protein, such as those comprising SEQ ID NO: 1 and SEQ ID NO: 2. For example, an immunogenic composition can comprise a mixture of an HIV clade C gp140 protein comprising the amino acid sequence of SEQ ID NO: 1 and an HIV mosaic gp140 protein comprising the amino acid sequence of SEQ ID NO: 2, e.g., in a 1:1 ratio.

The immunogenic compositions of the invention also comprise water, preferably water for injection. It is added to the composition in sufficient quantity (q.s.), depending on the volume of the composition being prepared.

According to embodiments of the invention, an immunogenic composition comprises 0.05 mg/mL to 5 mg/mL of an HIV gp140 protein, such as 0.05 mg/mL, 0.1 mg/mL, 0.2 mg/mL, 0.5 mg/mL, 1 mg/mL, 2 mg/mL, 3 mg/mL, 4 mg/mL, or 5 mg/mL. In particular embodiments of the invention, an immunogenic composition comprises 0.2 mg/mL or 1 mg/mL of an HIV gp140 protein, such as those comprising SEQ ID NO: 1 or SEQ ID NO: 2. In other particular embodiments of the invention, an immunogenic composition comprises a 0.05 mg/mL to 5 mg/mL of a mixture of HIV gp140 proteins, such as those comprising SEQ ID NO: 1 and SEQ ID NO: 2, e.g., in a 1:1 ratio.

Immunogenic compositions of the invention further comprise sorbitol (sugar), polysorbate 20 (surfactant), and histidine buffer. The inventors surprisingly discovered that the stability of the HIV gp140 protein in a composition comprising histidine had improved stability as compared to that in compositions comprising other amino acids. The inventors also surprisingly discovered that inclusion of polysorbate 20 in the composition further improved the stability of the HIV gp140 protein in the composition. Typically, buffers used for protein formulations contain a combination of acetate and sorbitol, or a combination of histidine and sucrose (see e.g., Uchiyama, *Biochimica Biophysica Acta* (2014) 1844, 2041-2052). Histidine and sorbitol are not usually used in combination in a buffer for protein formulations. To the best of the knowledge of the inventors, the combination of histidine and sorbitol with polysorbate 20 (surfactant) has not been used in any commercial protein drug formulations. Therefore, it was surprising to see that the combination of histidine and sorbitol improved the stability of the HIV gp140 protein.

According to embodiments of the invention, the concentration of sorbitol can be in a range of 2% to 15% (w/v), such as 2%, 3%, 4%, 5%, 6%, 7%, 8%, 9%, 10%, 11%, 12%, 13%, 14% or 15% (w/v). In one preferred embodiment, the concentration of sorbitol is 5% (w/v). In another preferred embodiment, the concentration of sorbitol is 12% (w/v).

According to embodiments of the invention, the concentration of polysorbate 20 can be in a range of 0.01% to 0.05% (w/v), such as 0.01%, 0.02%, 0.03%, 0.04%, or 0.05% (w/v). In one preferred embodiment, the concentration of polysorbate 20 is 0.02% (w/v).

According to embodiments of the invention, the concentration of histidine buffer is in a range of 5 mM to 20 mM, such as 5 mM, 10 mM, 15 mM or 20 mM, and is preferably 10 mM. The pH of the histidine buffer is in a range of 5.5 to 7.0, such as 5.5, 6.0, 6.5, or 7.0, and is preferably 6.5. In one preferred embodiment, the concentration of the histidine buffer is 10 mM and the pH of the histidine buffer is 6.5. Any pH value described herein, is to be understood as being modified in all instances by the term "about," which, when used with reference to a pH value includes ±0.5 of the recited pH value. Unless specified otherwise, all pH values refer to the pH of the histidine buffer itself that is included in an immunogenic composition of the invention.

In certain embodiments of the invention, an immunogenic composition further comprises an adjuvant. The terms "adjuvant" and "immune stimulant" are used interchangeably herein, and are defined as one or more substances that cause stimulation of the immune system, or enhance an immune response. For example, an adjuvant can be used to enhance an immune response to an HIV gp140 protein and/or an immunogenic composition of the invention when administered alone or further in combination with one or more adenovirus vectors encoding one or more HIV antigens. Adjuvants suitable for use with the invention should be ones that are potentially safe, well tolerated and effective in people, such as, for instance QS-21, Iscomatrix, Detox-PC, MPL-SE, MoGM-CSF, TiterMax-G, CRL-1005, GERBU, TERamide, PSC97B, Adjumer, PG-026, GSK-I, GcMAF, B-alethine, MPC-026, Adjuvax, CpG ODN, Betafectin, aluminum salts (e.g. aluminum hydroxide, and/or aluminum phosphate; an example of an aluminum phosphate adjuvant is AdjuPhos, a sterilized aluminum phosphate wet gel suspension), Adjuplex, and MF59. Preferably, the adjuvant is an aluminum phosphate adjuvant.

According to embodiments of the invention, an aluminum phosphate adjuvant can be included in an immunogenic composition at concentrations of between about 0.7 and 5.0 mg/mL, for instance 0.7, 0.75, 0.8, 0.85, 0.9, 0.95, or 1 mg/ml, e.g. at a fixed concentration of 0.85 mg/mL, or for instance 1.5, 2.0, 2.5, 3.0, 3.5, 3.6, 3.7, 3.8, 3.85, 3.9, 3.95, 4.0, 4.5, or 5.0 mg/mL, e.g. at a fixed concentration of 3.84 mg/mL. One goal of the invention was to provide long-term stable formulations with aluminum phosphate adjuvant present together with the gp140 protein immunogen. It was surprisingly found that the liquid formulations of the invention that comprise HIV gp140, histidine buffer, sorbitol, and polysorbate 20, are stable for at least 6 months at 2-8° C. These formulations were also found to be stable for at least 6 months at elevated temperatures of 25° C. In addition, these formulations were even found to be stable for at least 2 weeks, 1 month, or even up to 3 months at 40° C., as measured by reduced SDS PAGE.

In an exemplary embodiment of the invention, an immunogenic composition comprises, relative to the total volume of the composition:
  a. 0.2 mg/mL to 1 mg/mL of an HIV gp140 protein comprising the amino acid sequence of SEQ ID NO: 1 or SEQ ID NO: 2;
  b. 5% to 12% (w/v) sorbitol;
  c. 0.02% (w/v) polysorbate 20;
  d. 10 mM histidine buffer at a pH of 6.5; and
  e. 0.7 to 4.0 mg/mL (e.g. 0.85 mg/mL or 3.84 mg/mL) aluminum phosphate adjuvant.

Immunogenic compositions of the invention can be formulated in any matter suitable for administration to a subject to facilitate administration and improve efficacy, including, but not limited to, oral (enteral) administration and parenteral injections. The parenteral injections for instance can include subcutaneous injection, intramuscular injection, or intradermal injection. Immunogenic compositions of the invention can also be formulated for other routes of administration, e.g. transmucosal, rectal, sublingual administration, oral, or intranasal. Preferably, an immunogenic composition is formulated for intramuscular injection.

Immunogenic compositions of the invention are advantageous in that the HIV gp140 protein can be stably stored in liquid form at refrigerated temperature, for instance 2° C. to 8° C., for extended periods of time, such as about 2 years. In certain embodiments, the immunogenic compositions include an adjuvant, for instance aluminum phosphate adjuvant. The immunogenic compositions containing adjuvant are also compatible with storage in liquid form under refrigerated conditions for extended periods of time. The immunogenic compositions of the invention are also compatible with storage in lyophilized form. However, the compositions of the invention are thus preferably liquid formulations, meaning that they are in liquid form at the preferred storage temperature, i.e. at 2-8° C. Typically the liquid formulations or compositions according to the invention are aqueous suspensions, meaning that not all protein and/or particulate material such as aluminum phosphate may be entirely dissolved. In such cases it is advised to mix the composition before use. It is preferred to store the compositions of the invention that comprise aluminum phosphate adjuvant above the freezing point of water, most preferably at 2-8° C., e.g. e.g. 2° C., 3° C., 4° C., 5° C., 6° C., 7° C., or 8° C. Advantages are that no resource-intensive and costly lyophilization and associated re-dissolving before use is needed, no bed-side mixing and separate storage of the aluminum phosphate adjuvant is needed but rather the formulations can be stored 'ready-for-use'. In addition, storage at refrigerated but not frozen conditions makes that the compositions can be used more easily in resource-limited settings e.g. where no freezing capacity is available. Moreover, the observed maintained stability at elevated temperatures (e.g. 25° C., and even 40° C.) of the compositions of the invention indicates that inadvertent temperature excursions, e.g. when temporarily the composition is exposed to room temperature even in warm climates, should not immediately be detrimental to the vaccine composition of the invention.

The compositions of the invention, surprisingly including the ones comprising aluminum phosphate, are stable upon storage at a temperature of 2-8° C. for at least one day, one week, two weeks, one month, preferably at least 2, 3, 4, 5, 6 months. More preferably these compositions are stable under these conditions for at least 7, 8, 9, 10, 11, 12 months, still more preferably at least 13, 14, 15, 16, 17, 18, 19, 20, 21, 22, 23, 24 months, most preferably at least 25, 26, 27, 28, 29, 30, 31, 32, 33, 34, 35, 36 months or longer, e.g. 1-72 months, e.g. 6-48 months, e.g. 12-36 months. The invention in certain embodiments thus provides compositions according to the invention, which are stable when stored at 2-8° C. for at least one month, at least three months, at least 6 months. Preferably such compositions are stable for at least 12 months, at least 18 months, at least 24 months, at least 30 months, at least 36 months. In certain embodiments, the invention provides using the immunogenic compositions of the invention for vaccinating a subject, preferably a human subject, after the immunogenic compositions have been stored at 2-8° C. for at least one day, at least one week, at least two weeks, at least three weeks, at least one month, at least two months, at least three months, at least 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 months.

For the purpose of the present invention, an immunogenic composition that comprises HIV gp140 protein and that after having been stored for at least one week, preferably at least one month, at a given temperature does not show more than 25%, preferably not more than 10%, of degradation of said gp140 protein on a reduced SDS PAGE gel, is considered a long-term storage stable immunogenic composition at said temperature. An immunogenic composition that comprises HIV gp140 protein is considered "stable" according to the present invention under certain conditions (e.g. 2-8° C.) for a specified time (e.g. 6 months), if under these conditions after said specified time said gp140 protein does not show more than 25%, preferably less than 20%, preferably less than 15%, preferably less than 10%, most preferably less than 5%, of degradation (compared to initial measurement at t=0) on a reduced SDS PAGE gel. Degradation is visible as additional bands below the gp140 band of desired molecular weight. Alternative assays such as ELISA can also be used to measure stability, and in certain embodiments, a composition that is stable as defined above, also does not show more than 50%, preferably less than 25%, degradation (reduction as compared to initial signal at t=0) in an ELISA assay.

Methods of Preparing an Immunogenic Composition

The invention also relates to a method of preparing an immunogenic composition of the invention. According to embodiments of the invention, a method of preparing an immunogenic composition comprises admixing an HIV gp140 protein, sorbitol, polysorbate 20, and histidine buffer in the appropriate concentration ranges. One of ordinary skill in the art will be familiar with conventional techniques used to prepare such compositions.

For example, immunogenic compositions can be prepared by mixing histidine buffer, sorbitol, and polysorbate 20 at the desired concentrations. Then, the HIV gp140 protein can be added. The pH of the composition can be adjusted before or after addition of the HIV gp140 protein. As another illustrative example, first a buffer solution containing histidine and sorbitol can be prepared. The HIV gp140 protein is prepared in buffer at the desired concentration, and then added to the buffer solution containing histidine and sorbitol, followed by addition of Polysorbate at the target concentration. Adjuvant can be added last to obtain the final composition. The invention also provides methods for preparing a long-term, storage stable immunogenic composition that comprises HIV gp140 protein. In certain embodiments, such methods comprise: (i) providing an immunogenic composition according to the invention (i.e. comprising 0.05-5 mg/mL HIV gp140 protein, 2-15% (w/v) sorbitol, 0.01-0.05% polysorbate 20, 5-20 mM histine buffer pH 5.5-7.0, water, and preferably 0.7-4.0 mg/mL aluminum phosphate), and (ii) storing said composition at 2-8° C. for at least one month, e.g. 1-72 months, e.g. 6-48 months, e.g. 12-36 months, e.g. 18-30 months. In certain embodiments, such methods comprise:

(i) admixing the following components to create an immunogenic composition comprising these components in amounts relative to the total volume of the composition:
 (a) 0.05 mg/mL to 5 mg/mL of an HIV gp140 protein;
 (b) 2% to 15% (w/v) sorbitol;
 (c) 0.01 to 0.05% (w/v) polysorbate 20;
 (d) 5 to 20 mM histidine buffer at a pH of 5.5 to 7.0,
 (e) water (preferably water for injection),
 (f) aluminum phosphate adjuvant, preferably at a concentration of 0.7-4 mg/mL; and
(ii) storing the composition at 2-8° C. for at least one month, e.g. 1-72 months, e.g. 6-48 months, e.g. 12-36 months, e.g. 18-30 months.

Methods of Inducing an Immune Response

The invention also relates to methods of inducing an immune response against human immunodeficiency virus (HIV) in a subject in need thereof with an immunogenic composition of the invention. The immune response can be against one or more HIV clades. The methods described herein also include administering an immunogenic composition of the invention in combination with one or more additional HIV antigens that are preferably expressed from one or more vectors, such as adenovirus vectors or MVA vectors, including methods of priming and boosting an immune response.

In one general aspect, a method of inducing an immune response against a human immunodeficiency virus (HIV) in a subject in need thereof comprises administering to the subject an effective amount of an immunogenic composition comprising an HIV gp140 protein according to an embodiment of the invention. Any of the immunogenic compositions described herein can be used in a method of inducing an immune response against HIV in a subject. Preferably, the composition comprises a stabilized trimeric HIV gp140 protein, such as an HIV clade C gp140 protein comprising the amino acid sequence of SEQ ID NO: 1, or an HIV mosaic gp140 protein comprising the amino acid sequence of SEQ ID NO: 2, or a mixture thereof. The composition can further comprise an adjuvant, such as aluminum phosphate adjuvant. An exemplary embodiment of an immunogenic composition for use in the methods of the invention comprises, relative to the total volume of the composition,
 a. 0.2 mg/mL to 1 mg/mL of an HIV gp140 protein comprising the amino acid sequence of SEQ ID NO: 1 or SEQ ID NO: 2;
 b. 5% to 12% (w/v) sorbitol;
 c. 0.02% (w/v) polysorbate 20;
 d. 10 mM histidine buffer at a pH of 6.5; and
 e. 0.7 to 4.0 mg/mL (e.g. 0.85 mg/mL or 3.84 mg/mL) aluminum phosphate adjuvant.

According to embodiments of the invention, "inducing an immune response" when used with reference to the methods and compositions described herein encompasses providing protective immunity and/or vaccinating a subject against an infection, such as an HIV infection, for prophylactic purposes, as well as causing a desired immune response or effect in a subject in need thereof against an infection, such as an HIV infection, for therapeutic purposes. Preferably, the methods of the invention are for prophylactic purposes, such as for providing protective immunity. The immune response can be a cellular immune response and/or a humoral immune response.

As used herein, the term "protective immunity" or "protective immune response" means that the vaccinated subject is able to control an infection with the pathogenic agent against which the vaccination was done. Usually, the subject having developed a "protective immune response" develops only mild to moderate clinical symptoms or no symptoms at all. Usually, a subject having a "protective immune response" or "protective immunity" against a certain agent will not die as a result of the infection with said agent.

Typically, administration of immunogenic compositions according to embodiments of the invention will have a prophylactic aim to generate an immune response against an HIV antigen before infection or development of symptoms. In other embodiments, the immunogenic compositions can be administered for post-exposure prophylactics. Immunogenic compositions of the invention can also be administered to a non-human mammal, such as for experimental purposes.

As used herein, "an effective amount" or "immunologically effective amount" means an amount of a composition sufficient to induce a desired immune effect or immune response in a subject in need thereof. In one embodiment, an effective amount means an amount sufficient to induce an immune response in a subject in need thereof. In certain embodiments, an effective amount means an amount sufficient to produce immunity in a subject in need thereof, e.g., provide a protective effect against a disease such as a viral infection. In certain embodiments, an effective amount means an amount sufficient to enhance an immune response in a subject in need thereof. For example, when used in combination with one or more other components or immunogenic compositions capable of effecting an immune response, such as in a prime-boost regimen, an effective amount can be an amount sufficient to enhance the immune response induced by the one or more other components or immunogenic compositions.

An effective amount can vary depending upon a variety of factors, such as the physical condition of the subject, age, weight, health, etc.; the particular application, e.g., whether inducing immune response or providing protective immunity; and the particular disease, e.g., viral infection, for which immunity is desired. An effective amount can readily be determined by one of ordinary skill in the art in view of the present disclosure. As general guidance, when used with reference to an HIV gp140 protein an effective amount can range from, e.g. about 0.3 to about 3000 microgram (μg), e.g. 1-1000 μg, e.g. 10-500 μg, e.g. about 50, 100, 150, 200, 250, 300, 350, 400, 450 or 500 μg.

An effective amount of an immunogenic composition can be administered in a single composition, or in multiple compositions, such as 1, 2, 3, 4, 5, 6, 7, 8, 9, or 10 compositions (e.g., tablets, capsules and/or injectables), wherein the administration of the multiple compositions (e.g., tablets, capsules and/or injectables) collectively provides a subject with the immunogenically effective amount. It is also possible to administer an effective amount of an immunogenic composition to a subject, and subsequently administer another dose of an effective amount of an immunogenic composition to the same subject, in a so-called prime-boost regimen, as described in greater detail below.

According to embodiments of the invention, an immunogenic composition can be administered to a subject by any means known in the art including, but not limited to, oral (enteral) administration and parenteral injections. The parenteral injections could for instance include subcutaneous injection, intramuscular injection, or intradermal injection. Preferably, the immunogenic composition is administered by intramuscular injection.

It is also possible to administer immunogenic compositions of the invention together with one or more additional HIV antigens, or one or more vectors, such as adenovirus vectors, encoding one or more additional HIV antigens. As used herein, the terms "co-delivery," "co-administration," "administered together with," or "administered in combination with" refer to simultaneous administration of two or more components, such as an immunogenic composition comprising an HIV gp140 protein, or multiple viral expression vectors, such as adenovirus vectors. "Simultaneous administration" can be administration of the two or more components at least within the same day. When two components are "administered together with," they can be administered in separate compositions sequentially within a short time period, such as 24, 20, 16, 12, 8, or 4 hours, or within 1 hour or less, or they can be administered in a single composition at the same time. Non-limiting examples of administration of immunogenic compositions of gp140 protein with one or more additional HIV antigens encoded by vectors such as adenoviral vectors, are provided in WO 2016/049287, the disclosure of which is herein incorporated by reference in its entirety.

Thus, in certain embodiments of the invention, a method of inducing an immune response further comprises administering to the subject an effective amount of a second immunogenic composition comprising one or more HIV antigens or one or more vectors encoding the HIV antigens. Any HIV antigen known to those skilled in the art in view of the present disclosure can be used, such as HIV Nef, Gag, Env, or Pol antigens or any antigenic portion or epitope or combination thereof. Mosaic HIV antigens can also be used. Exemplary HIV antigens include, but are not limited to, mosaic Env, Gag, and/or Pol antigens and combinations thereof, such as those comprising the amino acid sequences of SEQ ID NOs: 3-12, or SEQ ID NO: 11 having one or more mutations selected from the group consisting of (i) I529P (Ile to Pro at position 529), (ii) K480E (Lys to Glu at position 480), and (iii) a combination of EK479-480RRRR (i.e. replacing GluLys at position 479 and 480 by four consecutive Arg residues), I529P (Ile to Pro at position 529), A471C (Ala to Cys at position 471) and T575C (Thr to Cys at position 575). The additional HIV antigens can for instance be administered to the subject as isolated proteins or polypeptides or as vectors encoding these proteins or polypeptides.

Preferably, in the method comprising administering to the subject an effective amount of a second immunogenic composition, the second immunogenic composition comprises one or more vectors encoding one or more HIV antigens.

Any vector known to those skilled in the art in view of the present disclosure can be used. Preferably, the vector is an adenovirus vector, more preferably an adenovirus 26 vector. The preparation of recombinant adenoviral vectors is well known in the art. Preparation of recombinant adenovirus 26 (rAd26) vectors is described, for example, in WO 2007/104792 and in Abbink et al., (2007) Virol 81(9): 4654-63. Exemplary genome sequences of Ad26 are found in GenBank Accession EF 153474 and in SEQ ID NO: 1 of WO 2007/104792. Examples of vectors useful for the invention for instance include those described in WO2012/082918, the disclosure of which is incorporated herein by reference in its entirety. Other adenovirus vectors that can be used in combination with immunogenic compositions of the invention include those described in WO 2016/049287 and PCT Application No. PCT/EP2016/081159, the disclosures of which are herein incorporated by reference in their entirety.

According to embodiments of the invention, adenovirus vectors can comprise one HIV antigen, or more than one HIV antigen, such as two, three, or four or more HIV antigens. Immunogenic compositions can comprise one or more adenovirus vectors, such as two, three, four or more HIV antigens, encoding one or more different HIV antigens. Also according to embodiments of the invention, a second composition can comprise one adenovirus vector, or more than one adenovirus vector, such as two, three, four or more adenovirus vectors. If a second composition comprises more than one adenovirus vector, the adenovirus vectors can encode the same or different HIV antigens.

Adenovirus vectors encoding one or more HIV antigens for use in the methods of the invention comprise nucleic acid encoding an HIV antigen that is operably linked to a promoter, meaning that the nucleic acid is under the control of a promoter. The promoter can be a homologous promoter (i.e., derived from the same genetic source as the vector) or a heterologous promoter (i.e., derived from a different vector or genetic source). Examples of suitable promoters include the cytomegalovirus (CMV) promoter and the Rous Sarcoma virus (RSV) promoter. Preferably, the promoter is located upstream of the nucleic acid within an expression cassette.

As general guidance, an "effective amount" when used with reference to adenovirus vectors, can range from about $10^8$ viral particles to about $10^{12}$ viral particles, for example $10^8$, $10^9$, $10^{10}$, $10^{11}$, or $10^{12}$ viral particles. The preparation and use of immunogenic compositions comprising adenovirus vectors, such as adenovirus 26 vectors, are well known to those of ordinary skill in the art. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can also be included.

For instance recombinant adenovirus vector can be stored in the buffer that is also used for the Adenovirus World Standard (Hoganson et al. 2002, *Bioprocessing J* 1: 43-8): 20 mM Tris pH 8, 25 mM NaCl, and 2.5% glycerol. Another useful adenovirus formulation buffer suitable for administration to humans is 20 mM Tris, 2 mM $MgCl_2$, 25 mM NaCl, 10% (w/v) sucrose, and 0.2% (w/v) polysorbate-80. Another formulation buffer that is suitable for recombinant adenovirus comprises 10-25 mM citrate buffer pH 5.9-6.2, 4-6% (w/w) hydroxypropyl-beta-cyclodextrin (HBCD), 70-100 mM NaCl, 0.018-0.035% (w/w) polysorbate-80, and optionally 0.3-0.45% (w/w) ethanol. Other buffers can be used, and several examples of suitable formulations for the storage and for pharmaceutical administration of purified vectors are known.

Administration of immunogenic compositions comprising the one or more additional HIV antigens or one or more adenovirus vectors encoding the one or more additional HIV antigens is typically intramuscular, intradermal or subcutaneous. However, other modes of administration such as intravenous, rectal, cutaneous, oral, nasal, etc. can be envisaged as well. Intramuscular administration of the immunogenic compositions can be achieved by using a needle to inject a suspension of the expression vectors, e.g. adenovirus vectors, and/or antigenic polypeptides. An alternative is the use of a needleless injection device to administer the composition (using, e.g., Biojector™) or a freeze-dried powder containing the vaccine.

In one embodiment, an immunogenic composition comprising a gp140 protein according to an embodiment of the invention is used in combination with an adenovirus vector, preferably an adenovirus 26 vector, encoding a HIV antigen comprising the amino acid sequence of SEQ ID NO: 3.

In one embodiment, an immunogenic composition comprising an HIV gp140 protein according to an embodiment of the invention is used in combination with an adenovirus vector, preferably an adenovirus 26 vector, encoding a HIV antigen comprising the amino acid sequence of SEQ ID NO: 4.

In one embodiment, an immunogenic composition comprising an HIV gp140 protein according to an embodiment of the invention is used in combination with an adenovirus vector, preferably an adenovirus 26 vector, encoding a HIV antigen comprising the amino acid sequence of SEQ ID NO: 5.

In one embodiment, an immunogenic composition comprising an HIV gp140 protein according to an embodiment of the invention is used in combination with an adenovirus vector, preferably an adenovirus 26 vector, encoding a HIV antigen comprising the amino acid sequence of SEQ ID NO: 6.

In one embodiment, an immunogenic composition comprising an HIV gp140 protein according to an embodiment of the invention is used in combination with an adenovirus vector, preferably an adenovirus 26 vector, encoding a HIV antigen comprising the amino acid sequence of SEQ ID NO: 7.

In one embodiment, an immunogenic composition comprising an HIV gp140 protein according to an embodiment of the invention is used in combination with an adenovirus vector, preferably an adenovirus 26 vector, encoding a HIV antigen comprising the amino acid sequence of SEQ ID NO: 8.

In one embodiment, an immunogenic composition comprising an HIV gp140 protein according to an embodiment of the invention is used in combination with an adenovirus vector, preferably an adenovirus 26 vector, encoding a HIV antigen comprising the amino acid sequence of SEQ ID NO: 9.

In one embodiment, an immunogenic composition comprising an HIV gp140 protein according to an embodiment of the invention is used in combination with an adenovirus vector, preferably an adenovirus 26 vector, encoding a HIV antigen comprising the amino acid sequence of SEQ ID NO: 10.

In one embodiment, an immunogenic composition comprising an HIV gp140 protein according to an embodiment of the invention is used in combination with an adenovirus vector, preferably an adenovirus 26 vector, encoding a HIV antigen comprising the amino acid sequence of SEQ ID NO: 11, SEQ ID NO: 11 having one or more mutations selected from the group consisting of (i) I529P (Ile to Pro at position 529), (ii) K480E (Lys to Glu at position 480), and (iii) a combination of EK479-480RRRR (i.e. replacing GluLys at position 479 and 480 by four consecutive Arg residues), I529P (Ile to Pro at position 529), A471C (Ala to Cys at position 471) and T575C (Thr to Cys at position 575), or SEQ ID NO: 12.

Upon administration of adenovirus vectors encoding one or more HIV antigens, the adenovirus vector expresses the encoded HIV antigens, such that the HIV antigens are presented to the immune system of the subject, thereby inducing the required response to produce immunity, or induce an immune response. An immunogenic composition comprising an HIV gp140 protein according to an embodiment of the invention can be administered together with the one or more adenovirus vectors to prime the immune response, and/or subsequent to administration of the one or more adenovirus vectors to boost the immune response.

Thus, in other embodiments of the invention, a method of inducing an immune response against an HIV in a subject in need thereof comprises (i) administering to the subject an effective amount of an immunogenic composition comprising an HIV gp140 protein according to an embodiment of the invention, and preferably further comprising an adjuvant, and (ii) administering to the subject an effective amount of a second immunogenic composition comprising one or more adenovirus vectors encoding one or more HIV antigens. Steps (i) and (ii) are conducted in either order, with one of the steps for priming immunization and the other for boosting immunization. Optionally, the method can further comprise administering one or more Modified Vaccinia Ankara (MVA) vectors encoding one or more HIV antigens. MVA vectors can encode any HIV antigen described herein. Preferably, the MVA vectors encode one or more HIV antigens selected from the group consisting of SEQ ID NOs: 3-12, or SEQ ID NO: 11 having one or more mutations selected from the group consisting of (i) I529P (Ile to Pro at position 529), (ii) K480E (Lys to Glu at position 480), and (iii) a combination of EK479-480RRRR (i.e. replacing GluLys at position 479 and 480 by four consecutive Arg residues), I529P (Ile to Pro at position 529), A471C (Ala to Cys at position 471) and T575C (Thr to Cys at position 575).

Examples of adenovirus vectors, MVA vectors, and prime-boost regimens that can be used in combination with an immunogenic composition comprising an HIV gp140 protein according to an embodiment of the invention include those described in WO 2016/049287, the disclosure of which is herein incorporated by reference in its entirety.

For example, in one embodiment of the disclosed methods, one or more adenovirus vectors encoding one or more HIV antigens are used to prime the immune response. An immunogenic composition comprising an HIV gp140 protein according to the invention can be used together with the one or more adenovirus vectors for the priming immunization. The priming immunization can be administered only once, but can optionally also be administered multiple times, for example, initial priming administration at time 0, followed by another priming administration about 4-14 weeks, e.g. 10-14 weeks after the initial priming administration. The immunogenic composition comprising an HIV gp140 protein optionally together with one or more additional adenovirus or MVA vectors encoding one or more additional HIV antigens can be used to boost the immune response. A boosting immunization can also be administered once or multiple times, for example, first at about 22-26 weeks after the initial priming administration, followed by another boosting administration at about 46-50 weeks after the initial priming administration. The immune response induced by the immunization is monitored.

In other general aspects, the invention relates to vaccine combinations for inducing an immune response against a human immunodeficiency virus (HIV) in a subject in need thereof. According to embodiments of the invention, the vaccine combination comprises an immunogenic composition comprising an HIV gp140 protein, such as that comprising the amino acid sequence of SEQ ID NO: 1 or SEQ ID NO: 2; one or more adenovirus vectors, preferably adenovirus 26 vectors, encoding one or more HIV antigens, such as an HIV antigen comprising an amino acid sequence selected from the group consisting of SEQ ID NO:s 3 to 12, and SEQ ID NO: 11 having one or more mutations selected from the group consisting of (i) I529P (Ile to Pro at position 529), (ii) K480E (Lys to Glu at position 480), and (iii) a combination of EK479-480RRRR (i.e. replacing GluLys at position 479 and 480 by four consecutive Arg residues), I529P (lie to Pro at position 529), A471C (Ala to Cys at position 471) and T575C (Thr to Cys at position 575) and optionally one or more MVA vectors encoding one or more HIV antigens, such as an HIV antigen comprising an amino acid sequence selected from the group consisting of SEQ ID NO:s 3 to 12, and SEQ ID NO: 11 having one or more mutations selected from the group consisting of (i) I529P (Ile to Pro at position 529), (ii) K480E (Lys to Glu at position 480), and (iii) a combination of EK479-480RRRR (i.e. replacing GluLys at position 479 and 480 by four consecutive Arg residues), I529P (Ile to Pro at position 529), A471C (Ala to Cys at position 471) and T575C (Thr to Cys at position 575).

According to embodiments of the invention, the vaccine combinations can be used in any of the methods described herein for inducing an immune response against an HIV in a subject in need thereof, including for priming and boosting an immune response.

EMBODIMENTS

Embodiment 1 is an immunogenic composition comprising, relative to the total volume of the composition:

a. 0.05 mg/mL to 5 mg/mL of an HIV gp140 protein;
b. 2% to 15% (w/v) sorbitol;
c. 0.01 to 0.05% (w/v) polysorbate 20; and
d. 5 to 20 mM histidine buffer at a pH of 5.5 to 7.0.

Embodiment 2 is the immunogenic composition of embodiment 1, wherein the concentration of the HIV gp140 is 0.2 mg/mL.

Embodiment 3 is the immunogenic composition of embodiment 1, wherein the concentration of the HIV gp140 is 1 mg/mL.

Embodiment 4 is the immunogenic composition of any of embodiments 1 to 3, wherein the concentration of sorbitol is 5% (w/v).

Embodiment 5 is the immunogenic composition of any of embodiments 1 to 3, wherein the concentration of sorbitol is 12% (w/v).

Embodiment 6 is the immunogenic composition of any of embodiments 1-5, wherein the concentration of polysorbate 20 is 0.02% (w/v).

Embodiment 7 is the immunogenic composition of any of embodiments 1-6, wherein the concentration of the histidine buffer is 10 mM, and the pH of the histidine buffer is 6.5.

Embodiment 8 is the immunogenic composition of any of embodiments 1-7, further comprising aluminum phosphate adjuvant, for instance at a concentration of 0.7-1.0 mg/mL, preferably at a concentration of 0.85 mg/mL.

Embodiment 9 is the immunogenic composition of any of embodiments 1-8, wherein the HIV gp140 protein comprises the amino acid sequence of SEQ ID NO: 1.

Embodiment 10 is the immunogenic composition of any of embodiments 1-8, wherein the HIV gp140 protein comprises the amino acid sequence of SEQ ID NO: 2.

Embodiment 11 is an immunogenic composition comprising, relative to the total volume of the composition, a. 0.2 mg/mL to 1 mg/mL of an HIV gp140 protein comprising the amino acid sequence of SEQ ID NO: 1 or SEQ ID NO: 2;
b. 5% to 12% (w/v) sorbitol;
c. 0.02% (w/v) polysorbate 20;
d. 10 mM histidine buffer at a pH of 6.5; and
e. aluminum phosphate adjuvant, e.g. at a concentration of 0.7-4.0 mg/mL, e.g. 0.85 mg/mL or 3.84 mg/mL.

Embodiment 12 is the immunogenic composition of embodiment 11, comprising 0.2 mg/mL HIV gp140 protein comprising the amino acid sequence of SEQ ID NO: 1 and 5% (w/v) sorbitol.

Embodiment 13 is the immunogenic composition of embodiment 11, comprising 0.2 mg/mL HIV gp140 protein comprising the amino acid sequence of SEQ ID NO: 2 and 5% (w/v) sorbitol.

Embodiment 14 is the immunogenic composition of embodiment 11, comprising 0.2 mg/mL HIV gp140 protein comprising the amino acid sequence of SEQ ID NO: 1 and 12% (w/v) sorbitol.

Embodiment 15 is the immunogenic composition of embodiment 11, comprising 0.2 mg/mL HIV gp140 protein comprising the amino acid sequence of SEQ ID NO: 2 and 12% (w/v) sorbitol.

Embodiment 16 is the immunogenic composition of embodiment 11, comprising 1.0 mg/mL HIV gp140 protein comprising the amino acid sequence of SEQ ID NO: 1 and 5% (w/v) sorbitol.

Embodiment 17 is the immunogenic composition of embodiment 11, comprising 1.0 mg/mL HIV gp140 protein comprising the amino acid sequence of SEQ ID NO: 2 and 5% (w/v) sorbitol.

Embodiment 18 is the immunogenic composition of embodiment 11, comprising 1.0 mg/mL HIV gp140 protein comprising the amino acid sequence of SEQ ID NO: 1 and 12% (w/v) sorbitol.

Embodiment 19 is the immunogenic composition of embodiment 11, comprising 1.0 mg/mL HIV gp140 protein comprising the amino acid sequence of SEQ ID NO: 2 and 12% (w/v) sorbitol.

Embodiment 20 is an immunogenic composition according to any of embodiments 1 to 19 formulated for intramuscular injection.

Embodiment 21 is a method of preparing an immunogenic composition comprising admixing:
a. 0.05 mg/mL to 5 mg/mL of an HIV gp140 protein;
b. 2% to 15% (w/v) sorbitol;
c. 0.01 to 0.05% polysorbate 20; and
d. 5 to 20 mM histidine buffer at a pH of 5.5 to 7.0;
to thereby obtain the immunogenic composition.

Embodiment 22 is a method of inducing an immune response against an HIV in a subject in need thereof, comprising administering to the subject an effective amount of an immunogenic composition comprising, relative to the total volume of the composition,
a. 0.05 mg/mL to 5 mg/mL of an HIV gp140 protein;
b. 2% to 15% (w/v) sorbitol;
c. 0.01 to 0.05% polysorbate 20; and
d. 5 to 20 mM histidine buffer at a pH of 5.5 to 7.0.

Embodiment 23 is the method of embodiment 22, wherein the immunogenic composition comprises, relative to the total volume of the composition,
a. 0.2 mg/mL to 1 mg/mL of an HIV gp140 protein comprising the amino acid sequence of SEQ ID NO: 1 or SEQ ID NO: 2;
b. 5% to 12% (w/v) sorbitol;
c. 0.02% polysorbate 20;
d. 10 mM histidine buffer at a pH of 6.5; and
e. aluminum phosphate adjuvant, e.g. at a concentration of 0.7-4.0 mg/mL, e.g. 0.85 mg/mL or 3.84 mg/mL.

Embodiment 24 is a method of inducing an immune response against an HIV in a subject in need thereof, comprising administering to the subject an effective amount of an immunogenic composition according to any one of embodiments 1 to 20, or to any one of embodiments 36-37.

Embodiment 25 is the method of any one of embodiments 22 to 24, further comprising administering to the subject an effective amount of one or more adenovirus vectors, preferably adenovirus 26 vectors, encoding one or more HIV antigens.

Embodiment 26 is the method of any one of embodiments 22 to 25 further comprising administering to the subject an effective amount of one or more MVA vectors encoding one or more HIV antigens.

Embodiment 27 is the method of embodiment 25 or embodiment 26, wherein the one or more HIV antigens comprise an amino acid sequence selected from the group consisting of SEQ ID NOs: 3 to 12, and SEQ ID NO: 11 having one or more mutations selected from the group consisting of (i) I529P (Ile to Pro at position 529), (ii) K480E (Lys to Glu at position 480), and (iii) a combination of EK479-480RRRR (i.e. replacing GluLys at position 479 and 480 by four consecutive Arg residues), I529P (Ile to Pro at position 529), A471C (Ala to Cys at position 471) and T575C (Thr to Cys at position 575).

Embodiment 28 is an immunogenic composition according to any one of embodiments 1-20, or to any one of embodiments 36-37, which is stable at 2-8° C. for at least six months.

Embodiment 29 is an immunogenic composition according to any one of embodiments 1-20, or to any one of embodiments 36-37, which is stable at 2-8° C. for at least 12 months, at least 18 months, at least 24 months, at least 30 months, at least 36 months.

Embodiment 30 is an immunogenic composition according to any one of embodiments 1-20, or to any one of embodiments 36-37, which is stable at 2-8° C. for 6-72 months.

Embodiment 31 is an immunogenic composition according to any one of embodiments 1-20, or to any one of embodiments 36-37, which is stable at 25° C. for at least six months.

Embodiment 32 is an immunogenic composition according to any one of embodiments 1-20, or to any one of embodiments 36-37, which is stable at 40° C. for at least one week, preferably at least two weeks.

Embodiment 33 is a method for storing an immunogenic composition comprising HIV gp140 protein, the method comprising providing a immunogenic composition according to any one of embodiments 1-20, or to any one of embodiments 28-32, or to any one of embodiments 36-37 and storing said composition at 2-8° C. for at least one day, e.g. at least one week, e.g. at least one month, e.g. 1 day-72 months, e.g. 6-48 months, e.g. 12-36 months, e.g. 18-30 months.

Embodiment 34 is a method for preparing a long-term, storage stable immunogenic composition that comprises HIV gp140 protein, the method comprising: (i) providing an immunogenic composition that comprises 0.05-5 mg/mL HIV gp140 protein, 2-15% (w/v) sorbitol, 0.01-0.05% polysorbate 20, 5-20 mM histine buffer pH 5.5-7.0, water, and preferably 0.7-4.0 mg/mL aluminum phosphate), and (ii) storing said composition at 2-8° C. for at least one week, e.g. at least one month, e.g. 1-72 months, e.g. 6-48 months, e.g. 12-36 months, e.g. 18-30 months.

Embodiment 35 is use of an immunogenic composition according to any one of embodiments 1-20, or to any one of embodiments 28-32, or to any one of embodiments 36-37, for administering to a subject, preferably a human subject, to induce an immune response against HIV, wherein the immunogenic composition prior to said administering has been stored at 2-8° C. for at least one day, e.g. at least one week, e.g. at least two weeks, e.g. at least three weeks, e.g. at least one month, e.g. at least two months, e.g. at least three months, e.g. at least 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 months.

Embodiment 36 is the immunogenic composition of any one of embodiments 1-9, wherein the HIV gp140 protein comprises a mixture of an HIV gp140 protein comprising the amino acid sequence of SEQ ID NO: 1 and an HIV gp140 protein comprising the amino acid sequence of SEQ NO: 2.

Embodiment 37 is the immunogenic composition of embodiment 36, wherein the HIV gp140 protein comprising the amino acid sequence of SEQ ID NO:1 and the HIV gp140 protein comprising the amino acid sequence of SEQ NO: 2 are present in the mixture at a 1:1 ratio.

EXAMPLES

Example 1: Formulation Development Study for HIV Clade C Gp140 Protein

There are numerous possibilities for each component that can be included in a protein formulation, e.g., buffer, sugar, pH value, surfactant etc. For example, different possibilities for buffers can include phosphate, acetate, HEPES, Tris, MOPS, etc.; different possibilities for amino acids can include histidine, arginine, lysine, alanine, etc.; different possibilities for sugars can include sucrose, sorbitol, glycerol, mannitol, trehalose, etc.; and different possibilities for surfactant can include polysorbate 20, polysorbate 80, Tween-20, Tween-80, etc. There are also many other types of excipients, and numerous possibilities for each, that can further be included in a protein formulation, such as osmolytes (e.g., glycine, proline, glycerol, urea, etc.), salts (e.g., sodium chloride, potassium chloride, sodium sulfate, etc.), carbohydrates (e.g., lactose), proteins and polymers (e.g., HSA, gelatin, PVP, PLGA, PEG, etc.), chelators and antioxidants (e.g., EDTA, DTPA, ethanol, etc.), preservatives (e.g., benzyl alcohol, m-cresol, phenol, etc.), etc. See, e.g., Kamerzell et al. Advanced Drug Delivery Reviews (2011) 63, 1118-1159. Accordingly, there are many different theoretical combinations of components that could be used to identify a formulation. However, the most suitable formulation is dependent upon the particular protein in the formulation.

The inventors therefore set out to find improved formulations that could meet the complex requirements in the unpredictable art of protein formulation, in particular, an improved HIV gp140 formulation that enables drug product manufacturing meeting large late phase and commercial scale demands, and includes aluminum phosphate adjuvant and gp140 protein to be stored as drug product in single vials at refrigerated temperature, and prevents instability associated with certain components present in currently used formulations. The formulations were designed for storage in liquid form, but with the potential to be stored in lyophilized form and reconstituted in liquid prior to injection.

Formulation screening studies were designed to evaluate different buffers (histidine, phosphate, and acetate), buffer strengths (10 mM to 50 mM), sugars (sucrose and sorbitol from 2% to 12% w/v), surfactants (polysorbate 20 and polysorbate 80 from 0.02% to 1% w/v), and pH values from 4.5 to 7.5 on the stability of HIV clade C gp140 protein formulations. The parameters were varied as shown in Table 1.

TABLE 1

HIV clade C gp140 protein formulation study design

| Buffer | Histidine (His) | Phosphate (Pho) | Acetate (Ace) |
|---|---|---|---|
| pH | 5.5-6.5 | 6.5-7.5 | 4.5-5.5 |
| Buffer Strength | 10 mM, 20 mM, or 50 mM | | |
| Sugar | Sucrose or sorbitol at 2% or 12% (w/v) | | |
| Surfactant | Polysorbate 20 (PS20) or polysorbate 80 (PS80) at 0.02%, 0.05%, or 0.10% (w/v) | | |

The formulations were prepared by adding the buffer components at the pH value to be tested, followed by addition of sugar and surfactant. The pH was adjusted as necessary. Then, the clade C gp140 protein (SEQ ID NO: 1) was added to a concentration of 1 mg/mL or 0.2 mg/mL.

Formulation stability was analyzed using a SolvoVPE system to evaluate concentration and turbidity. Samples of each formulation were analyzed at time 0 ($T_0$), and then after stressing at 40° C. for 24 hours ($T_{24}$). Formulation stability was also analyzed using dynamic light scattering (DLS).

Figure 1B:
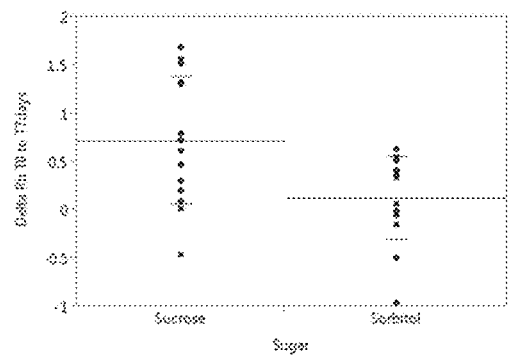
Figure 2A:
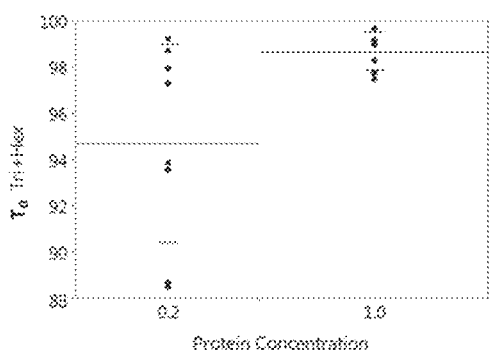
FIGS. 2A-2F show the results of high-performance size exclusion chromatography (HP-SEC) analysis of HIV gp140 formulations as described in Example 2; the relative amount of hexamer, trimer and high/low molecular weight species of HIV clade C gp140 protein was determined by HP-SEC of samples analyzed at time 0 ($T_0$) and after stressing the samples at 40° C. for 24 hours ($T_{24}$); "Tri+Hex" refers to the relative amount of trimer and hexamer species of HIV clade C gp140 protein; "LMW" refers to low molecular weight species, e.g., cleavage or degradation products, in particular.
Figure 2B:
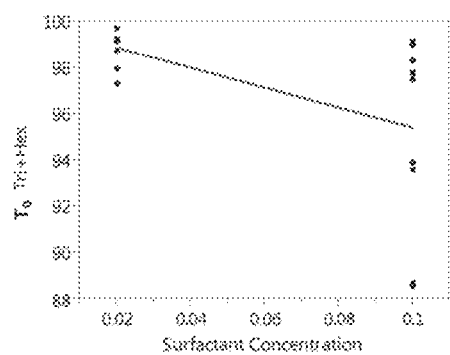
Figure 2C:
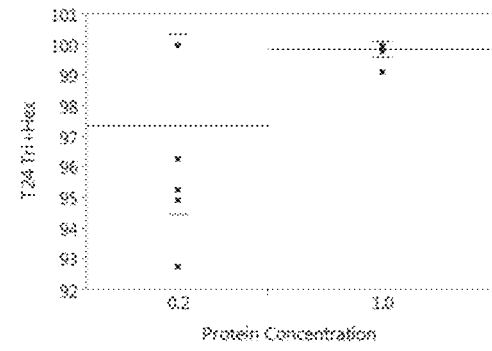
Figure 2D:
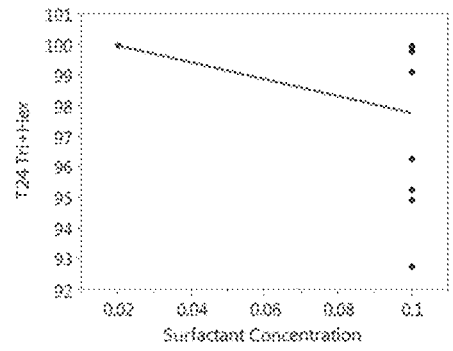
Figure 2E:
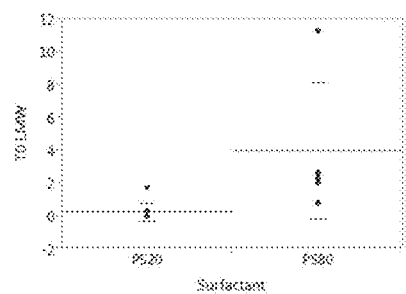
Figure 2F:
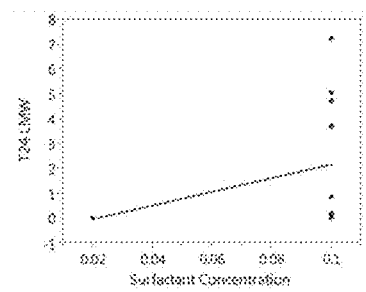

SolvoVPE Analysis:

A SolvoVPE (C Technologies, Inc.; Bridgeport, N.J., USA) was used to determine protein concentration by measuring the UV absorbance of samples of each formulation at 280 nm and 350 nm. The change in turbidity was determined from the difference in absorbance at 350 nm between $T_0$ and $T_{24}$ measurements. For desired formulations, any change in turbidity should preferably be as small as possible. Increases in turbidity indicate that the protein is precipitating out of solution, and that the formulation is thus less stable. The results of the SolvoVPE analysis are shown in FIG. 1.

The results of the SolvoVPE analysis show that the acetate buffer formulations had the highest increase in turbidity (average change of +0.339), whereas phosphate buffer formulations showed a moderate increase (average change of +0.177), and histidine buffer formulations shows almost no change in turbidity (average change of –0.010). Since a large change in turbidity is undesirable, the turbidity data indicate that histidine buffer is the most optimal buffer of those tested for improving the stability of HIV gp140 protein.

Dynamic Light Scattering (DLS) Analysis:

DLS was used to evaluate the colloidal stability, and specifically whether there was any protein aggregation in the protein formulations. The change in radius ($R_h$) from $T_0$ at 20° C. to $T_{7\ days}$ at 70° C. was measured. More specifically, the $R_h$ was measured for the initial sample at 20° C. Then, the sample was heated to 70° C., and held at a temperature of 70° C. for 7 days before measuring the final $R_h$. The difference in the initial $R_h$ value and the final $R_h$ values is plotted in FIG. 1B. A large change in $R_h$ indicates that there is protein aggregation, and that the formulation is thus less desirable.

The results of the DLS analysis show that formulations containing sorbitol had a lower change in $R_h$ as compared to formulations containing sucrose. Since a larger change in $R_h$ is undesirable, the DLS data indicate that sorbitol is the most optimal sugar of those tested for improving the stability of HIV gp140 protein.

The results of the above described studies also indicated that the sugar, sugar concentration, surfactant, surfactant concentration and protein concentration had an effect on the stability, so these parameters were further investigated as described in Example 2 below.

Example 2: Effect of Sugar, Surfactant, and Protein Concentration on Stability of HIV Clade C Gp140 Formulations HIV gp140 protein immunogenic formulations were prepared in a 10 mM histidine buffer, pH 6.0±0.5, with the following parameters being varied: sugar (sorbitol and sucrose), sugar concentration (2% and 12% w/v), polysorbate (PS20 and PS80), polysorbate concentration (0.02% and 0.1% w/v), and protein concentration (0.2 mg/mL and 1.0 mg/mL). The formulations were prepared by adding 10 mM histidine buffer, pH 6.0±0.5, followed by addition of sugar and surfactant. The pH was adjusted as necessary. HIV gp140 clade C protein (SEQ ID NO: 1) was added to the desired concentration. The formulations were then analyzed by High-Performance Size Exclusion Chromatography (HP-SEC), as described below.

The formulations prepared and tested are shown below in Table 2.

TABLE 2

HIV gp140 protein formulations

| Formulation | Sugar | Sugar Concentration (% w/v) | Surfactant | Surfactant Concentration (% w/v) | Protein concentration (mg/mL) |
|---|---|---|---|---|---|
| 1 | sorbitol | 12 | PS20 | 0.02 | 0.2 |
| 2 | sorbitol | 12 | PS80 | 0.1 | 0.2 |
| 3 | sorbitol | 2 | PS20 | 0.1 | 0.2 |
| 4 | sorbitol | 2 | PS20 | 0.1 | 0.2 |
| 5 | sorbitol | 2 | PS80 | 0.02 | 1 |
| 6 | sorbitol | 12 | PS80 | 0.02 | 1 |
| 7 | sorbitol | 12 | PS20 | 0.02 | 1 |
| 8 | sorbitol | 2 | PS80 | 0.1 | 1 |
| 9 | sorbitol | 12 | PS80 | 0.1 | 1 |
| 10 | sucrose | 12 | PS80 | 0.02 | 0.2 |
| 11 | sucrose | 2 | PS20 | 0.02 | 0.2 |
| 12 | sucrose | 12 | PS80 | 0.1 | 0.2 |
| 13 | sucrose | 2 | PS80 | 0.02 | 0.2 |
| 14 | sucrose | 2 | PS80 | 0.1 | 1 |
| 15 | sucrose | 2 | PS20 | 0.02 | 1 |
| 16 | sucrose | 2 | PS20 | 0.1 | 1 |
| 17 | sucrose | 12 | PS20 | 0.1 | 1 |
| 18 | sucrose | 12 | PS20 | 0.1 | 1 |

High-Performance Size Exclusion Chromatography (HP-SEC) Analysis:

HP-SEC was used to analyze the amount of hexamer, trimer, and high/low molecular weight species in formulation samples by monitoring the absorbance at 280 nm. The HIV gp140 protein exists predominantly as a trimer. Some HIV gp140 protein hexamer species is also observed. Although the trimer species is the desired species, immunogenicity against HIV is observed for both the trimer species and the hexamer species. High molecular weight (HMW) and low molecular weight (LMW) species in the formulations are undesired. In particular, the presence of LMW species indicates cleavage and/or degradation of the gp140 protein. HMW species may be caused by a number of factors, such as aggregation of the gp140 protein. Samples of each formulation were analyzed at time 0 ($T_0$), and then stressed at 40° C. for 24 hours ($T_{24}$). Formulations containing 1 mg/mL clade C gp140 protein were diluted two-fold before injection into the HP-SEC system, and formulations containing 0.2 mg/mL clade C gp140 protein were not diluted prior to injection.

The results of the HP-SEC analysis are shown below in Table 3, and in FIGS. 2A-2F. The results indicate that amount of trimer and hexamer for both $T_0$ and $T_{24}$ samples depends on the concentration of surfactant and HIV gp140 protein. Formulations having a lower surfactant concentration (0.02% w/v) had a higher observed value of trimer+hexamer species of the HIV gp140 protein, with less high/low molecular weight species observed (see FIGS. 2B, 2D, and 2F), both before and after sample stressing. Formulations having a higher HIV gp140 protein concentration (1.0 mg/mL) also had a higher observed value of trimer+hexamer species of the HIV gp140 protein, with less high/low molecular weight species observed (see FIGS. 2B and 2D), both before and after sample stressing (see FIGS. 2A and 2C). Formulations containing polysorbate 20, as opposed to polysorbate 80, also had a lower amount of lower molecular weight species present (see FIG. 2E).

TABLE 3

Results of HP-SEC Analysis.

| Formulation | High Molecular Weight Species (%) | | Hexamer (%) | | Trimer (%) | | Low Molecular Weight Species (%) | |
|---|---|---|---|---|---|---|---|---|
| | $T_0$ | $T_{24}$ | $T_0$ | $T_{24}$ | $T_0$ | $T_{24}$ | $T_0$ | $T_{24}$ |
| 1 | 0.57 | 0 | 10.69 | 10.13 | 88.05 | 89.87 | 0 | 0 |
| 2 | 0.22 | 0 | 8.48 | 9.55 | 80.08 | 85.39 | 11.22 | 5.06 |
| 3 | 0.2 | 0 | 9.15 | 9.51 | 84.47 | 85.77 | 0 | 4.72 |
| 4 | 0 | 0 | 9.26 | 9.56 | 84.63 | 86.71 | 0 | 3.73 |
| 5 | 0 | 0 | 10.72 | 12.27 | 88.41 | 87.73 | 0.86 | 0 |
| 6 | 0 | 0 | 10.78 | 11.6 | 88.44 | 88.4 | 0.78 | 0 |
| 7 | 0 | 0 | 11.08 | 11.7 | 88.6 | 88.3 | 0.32 | 0 |
| 8 | 0 | 0 | 10.46 | 11.67 | 87.33 | 88.33 | 2.21 | 0 |
| 9 | 0 | 0 | 10.6 | 11.57 | 86.91 | 88.43 | 2.48 | 0 |
| 10 | 0 | 0 | 9.79 | 10.02 | 88.17 | 89.98 | 2.05 | 0 |
| 11 | 0 | 0 | 10.52 | 10.54 | 88.75 | 89.46 | 0 | 0 |
| 12 | 0 | 0 | 8.9 | 9.23 | 79.79 | 83.51 | 11.31 | 7.26 |
| 13 | 0 | 0 | 9.74 | 10.58 | 87.58 | 89.42 | 2.68 | 0 |
| 14 | 0 | 0 | 10.37 | 11.82 | 87.38 | 87.98 | 2.25 | 0.2 |
| 15 | 0 | 0 | 10.91 | 12.15 | 88.77 | 87.85 | 0.32 | 0 |
| 16 | 0 | 0 | 10.57 | 11.42 | 87.71 | 87.72 | 1.72 | 0.86 |
| 17 | 0 | 0 | 10.63 | 11.45 | 88.51 | 88.43 | 0 | 0.12 |
| 18 | 0 | 0 | 10.74 | 11.54 | 88.28 | 88.46 | 0 | 0 |

The data shown in Table 3 indicates that the combination of sorbitol and histidine buffer is preferable to the combination of histidine buffer and sucrose. For examples, the formulations containing histidine buffer and sorbitol, such as formulations 1, 4, and 7, showed the least change between $T_0$ and T24 in the amount of hexamer and trimer species as compared to that observed for the formulations containing histidine buffer and sucrose. This result was surprising because histidine buffer and sorbitol are not typically used in combination for protein formulations, whereas histidine buffer and sucrose are often used in combination. It was thus unexpected that the most optimal formulation comprised histidine buffer (pH 6.0±0.5) and sorbitol, rather than histidine buffer and sucrose. The above study also indicates that including polysorbate 20 as a surfactant (see, e.g., FIG. 2E) at a concentration of 0.2% (w/v) (see, e.g., FIGS. 2B, 2D, and 2F) provides a formulation in which the stability of the HIV gp140 protein is further improved.

Advantages of the formulations identified herein over the one that is currently used for gp140 drug product in clinical trials, include that they use existing qualified compendial grade excipients that are readily available for large scale manufacturing and do not suffer from known issues that might negatively influence stability in the long term, and they enable storage of stable bulk drug substance and antigen drug product. Moreover, these formulations enable storage and stability of adjuvanted drug product as a single vial drug product at refrigerated temperature. These formulations are suitable for storage in liquid form, but also have the potential to be stored in lyophilized form and then reconstituted in liquid prior to injection, which is yet another advantage.

Example 3: Stability Studies of HIV Mosaic Gp140 Protein Formulations

Two formulations containing HIV mosaic gp140 protein (SEQ ID NO: 2) were examined for stability in a freeze-thaw and temperature cycling study. The formulations tested are shown in Table 4

TABLE 4

HIV Mosaic gp140 Protein Formulations

| Formulation | Protein | Buffer | Sugar | Surfactant |
|---|---|---|---|---|
| F1 | 1.0 mg/mL | 10 mM histidine, pH 6.5 | 12% sorbitol | 0.02% PS20 |
| F2 | 1.0 mg/mL | 10 mM histidine, pH 6.5 | 2% sorbitol | 0.02% PS20 |

Figure 3A:
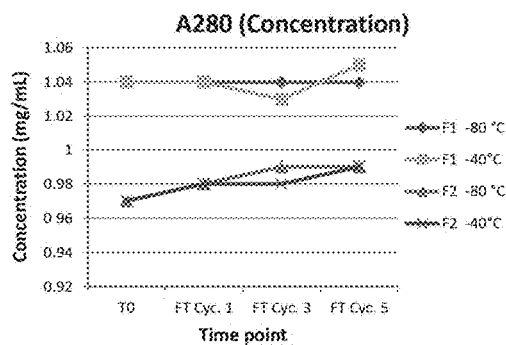
FIGS. 3A and 3B show the results of stability studies of HIV gp140 protein formulations according to embodiments of the invention; HIV mosaic gp140 protein formulations were subjected to multiple freeze-thaw cycles as described in Example 3.
Figure 3B:
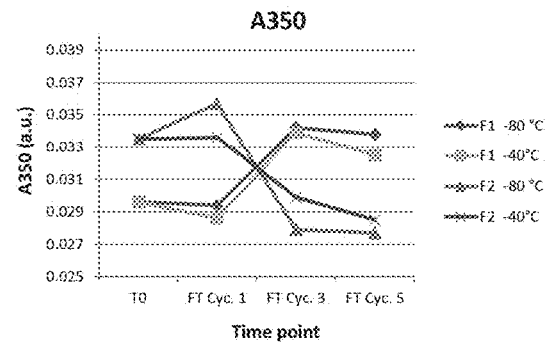

The formulations were subjected to multiple freeze-thaw cycles. One freeze-thaw cycle was conducted by freezing at −80° C. or −40° C. for 24 hours, followed by thawing at −2° C. to 8° C. for 24 hours. Samples were analyzed at the end of 1, 3, and 5 cycles of freeze-thaw by measuring the absorbance at 280 nm (concentration) and 350 nm (turbidity). The results are shown in FIG. 3A and FIG. 3B.

The results show that the absorbance at 350 nm and 280 nm was largely unchanged for both formulations F1 and F2 after multiple freeze-thaw cycles, indicating that the concentration and turbidity of the formulation were relatively unaffected. This demonstrates that the HIV gp140 protein in the formulations is stable to freeze-thaw.

Example 4: Long Term Stability Study of HIV Gp140 Protein Formulations

The stability of HIV gp140 protein compositions in histidine buffer, both with and without adjuvant according to embodiments of the invention was compared to the stability of an HIV gp140 protein composition formulated in HEPES buffer, both with and without adjuvant. The compositions tested are shown in Table 5. All formulations contained 0.2 mg/mL HIV clade C gp140 protein (SEQ ID NO: 1).

TABLE 5

HIV gp140 protein formulations for long term stability study.

| Formulation | Buffer Composition | Adjuvant? |
|---|---|---|
| 1 | 20 mM HEPES, pH 6.5<br>90 m, M NaCl<br>4% (w/v) sucrose<br>0.02% polysorbate 80 | No adjuvant |
| 2 | 10 mM histidine buffer, pH 6.5<br>12% (w/v) sorbitol<br>0.02% (w/v) polysorbate 20 | No adjuvant |
| 3 | 10 mM histidine buffer, pH 6.5<br>2% (w/v) sorbitol<br>0.02% (w/v) polysorbate 20 | No adjuvant |
| 4 | 10 mM histidine buffer, pH 6.5<br>5% (w/v) sorbitol<br>0.02% (w/v) polysorbate 20 | No adjuvant |
| 5 | 20 mM HEPES, pH 6.5<br>90 m, M NaCl<br>4% (w/v) sucrose<br>0.02% polysorbate 80 | + aluminum phosphate adjuvant (0.85 mg/mL) |
| 6 | 10 mM histidine buffer, pH 6.5<br>12% (w/v) sorbitol<br>0.02% (w/v) polysorbate 20 | + aluminum phosphate adjuvant (0.85 mg/mL) |
| 7 | 10 mM histidine buffer, pH 6.5<br>2% (w/v) sorbitol<br>0.02% (w/v) polysorbate 20 | + aluminum phosphate adjuvant (0.85 mg/mL) |
| 8 | 10 mM histidine buffer, pH 6.5<br>5% (w/v) sorbitol<br>0.02% (w/v) polysorbate 20 | + aluminum phosphate adjuvant (0.85 mg/mL) |

Compositions were stored at 2° C. to 8° C.; 25° C. and 60% relative humidity (RH); and 40° C. and 75% RH. The study is ongoing, and samples are tested after storage for 2 weeks, 1, 2, 3, 6, 9, 12, 18, 24, 30, and 36 months.

Figure 4A:
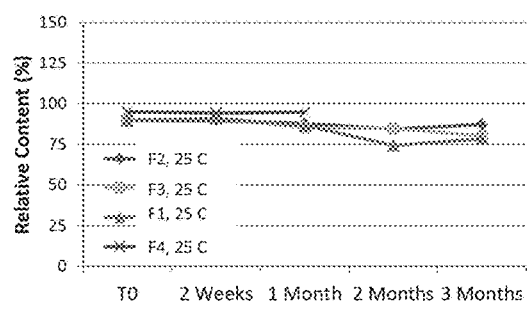
FIGS. 4A-4C show the results of stability studies of HIV clade C gp140 protein formulations; HIV clade C gp140 protein formulations were stored at 25° C. and 60% relative humidity (RH), and 40° C. and 75% RH, both with and without aluminum phosphate adjuvant, and then tested using a reduced SDS analytical method as described in Example 4.
Figure 4B:
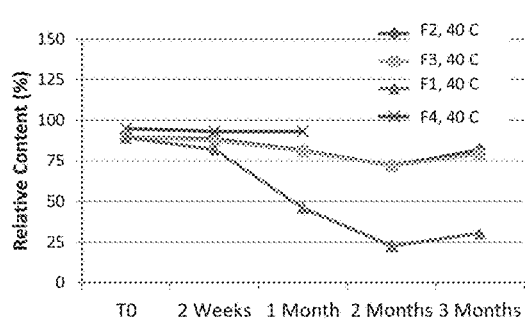
Figure 4C:
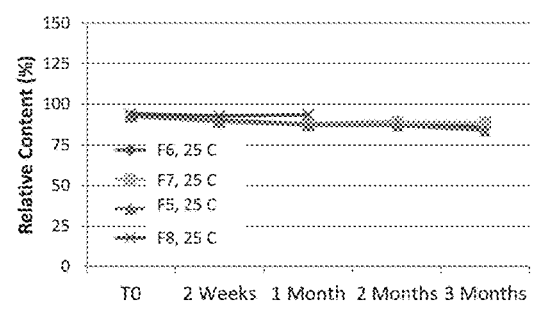
Figure 4D:
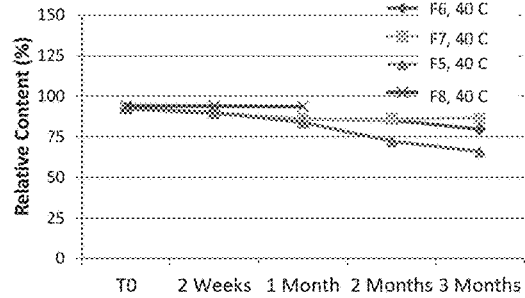
FIG. 4D shows the relative protein concentration (%) of HIV clade C gp140 formulations stored at 40° C. and 75% RH with aluminum phosphate adjuvant.

Samples were tested by reduced SDS after storage for up to three months. Under reducing conditions, as the SDS-PAGE was performed, the trimeric and hexameric forms were reduced to a monomeric form that showed up a single band on the gel. Any degradation of the protein to lower molecular weight species resulted in a change (decrease) in the monomeric form of the protein observed on the gel. The data for samples stored at 25° C. and 60% RH, and at 40° C. and 75% RH are shown in FIGS. 4A-4D. The data show that all formulations were stable under storage at 25° C. and 60% RH both with and without aluminum phosphate adjuvant for up to three months (FIGS. 4A and 4C). However, formulations containing histidine buffer and sorbitol were more stable than the formulation containing HEPES and sucrose (FIGS. 4B and 4D) when stored at 40° C. and 75% RH, both with and without aluminum phosphate adjuvant. In addition, after six months storage at 25° C. the histidine formulated material with 12% sorbitol, without aluminum phosphate adjuvant, showed better stability compared to the HEPES buffered formulation as measured by SDS-PAGE (smaller change in % compared to initial measurement; data not shown). Moreover, gp140 that was formulated with histidine buffer, sorbitol and aluminum phosphate was observed to be stable at 25° C. for at least six months (data not shown). Also when formulated with histidine buffer and sorbitol, at higher concentrations of aluminum phosphate adjuvant (3.84 mg/mL), the HIV gp140 protein was observed to be stable at 25° C. for at least six months and at 40° C. for at least three months as measured by reduced SDS PAGE (less than 25% reduction, data not shown; while measurements using ELISA showed stability (less than 50% reduction) at 40° C. for at least two weeks, data not shown). These data further indicate that HIV gp140 protein formulations containing histidine buffer and sorbitol have enhanced stability, and can thus be stored as an adjuvanted drug product in a single vial at elevated temperatures, which is an advantage as it is often difficult to formulate adjuvanted protein that is stable to storage at elevated temperatures. This means that the drug product with adjuvant can be stored in a single vial at a manufacturing or a fill-and-finish site, and does not require separate storage with mixing in a pharmacy or at bed-side just prior to administration. Apart from being economically beneficial, this is a huge advantage especially for an HIV vaccine product that is intended to be also used in many places where capacity and facilities may be limited. It is also an advantage of limiting the number of operations to be performed with the drug product on site where a large number of subjects are to be vaccinated in a single campaign. Thus, the formulations of the invention surprisingly improve the practical properties for use of the final vaccine, especially in resource-limited settings.

A combination of two HIV gp140 proteins, one having SEQ ID NO: 1 and one having SEQ ID NO: 2 is mixed (total protein concentration 0.2-1.0 mg/mL, e.g. 0.1 mg/mL for each protein resulting in a total concentration of gp140 protein of 0.2 mg/mL) and tested in the preferred formulation, i.e. 2% to 15% (w/v) sorbitol; 0.01 to 0.05% (w/v), e.g. 0.02%, polysorbate 20; and 5 to 20 mM, e.g. 10 mM, histidine buffer at a pH of 5.5 to 7.0, e.g. pH 6.5, and preferably aluminum phosphate, e.g. 0.7-4 mg/mL, e.g. 0.85 or 3.84 mg/mL, using methods as described above. This composition is also expected to be stable for at least six months at 2-8° C., like the individual proteins in this formulation as indicated above.

It is understood that the examples and embodiments described herein are for illustrative purposes only, and that changes could be made to the embodiments described above without departing from the broad inventive concept thereof. It is understood, therefore, that this invention is not limited to the particular embodiments disclosed, but it is intended to cover modifications within the spirit and scope of the invention as defined by the appended claims.

REFERENCES

1. Abbink et al., *Virol* (2007) 81(9): 4654-63.
2. Baicu et al., *Cryobiology* (2002) 45(1) 33-48.
3. Barouch et al., *Nat Med* (2010), 16: 319-323.
4. Barouch D H et al., *Science* (2015) 349: 320-324.
5. Barouch et al., *Cell* (2013) 155: 1-9.
6. Harris A et al., *Proc Natl Acad Sci USA* (2011) 108: 11440-11445.
7. Hoganson et al., *Bioprocessing* (2002) J 1: 43-8.
8. Kamerzell et al., *Advanced Drug Delivery Reviews* (2011) 63, 1118-1159.
9. Kovacs J M et al., *Proc Natl Acac Sci USA* (2012) 109: 12111-12116.
10. Lepe-Zuniga et al., *J. Immunol. Methods* (1987) 103(1), 145.
11. Nkolola et al., *J. Virol.* (2014) 88(17), 9538-9552.
12. Nkolola et al., *J. Virol.* (2010) 84(7), 3270-3279.
13. Sanders R W et al., *J. Virol.* (2002) 76: 8875-8889.
14. Sanders R W et al., *Science* (2015) 349(6244): aac4223, doi: 10.1126/science.aac4223.
15. Uchiyama, *Biochimica Biophysica Acta* (2014) 1844, 2041-2052.
16. Zhang C W-H et al., *J Biol Chem* (2001) 276: 39577-39585.
17. Zigler et al., In *Vitro Cell. Dev. Biol.* (1985) 21(5), 282-287.
18. WO 2010/042942
19. WO 2014/107744
20. US20120076812;
21. WO 2016/049287
22. WO 2010/059732
23. US20120076812
24. WO 2007/104792
25. PCT/EP2016/081159

The invention claimed is:

1. An immunogenic composition comprising, relative to the total volume of the composition:
   a. 0.05 mg/mL to 5 mg/mL of an HIV gp140 protein or of a mixture of at least two HIV gp140 proteins;
   b. 2% to 15% (w/v) sorbitol;
   c. 0.01 to 0.05% (w/v) polysorbate 20; and
   d. 5 to 20 mM histidine buffer at a pH of 5.5 to 7.0.

2. The immunogenic composition of claim 1, wherein the concentration of the HIV gp140 protein or of the mixture of HIV gp140 proteins is 0.2 mg/mL.

3. The immunogenic composition of claim 1, wherein the concentration of the HIV gp140 protein or of the mixture of HIV gp140 proteins is 1 mg/mL.

4. The immunogenic composition of claim 1, wherein the concentration of sorbitol is 5% (w/v).

5. The immunogenic composition of claim 1, wherein the concentration of sorbitol is 12% (w/v).

6. The immunogenic composition of claim 1, wherein the concentration of polysorbate 20 is 0.02% (w/v).

7. The immunogenic composition of claim 1, wherein the concentration of the histidine buffer is 10 mM, and the pH of the histidine buffer is 6.5.

8. The immunogenic composition of claim 1, further comprising aluminum phosphate adjuvant.

9. The immunogenic composition of claim 1, wherein the HIV gp140 protein comprises the amino acid sequence of SEQ ID NO: 1.

10. The immunogenic composition of claim 1, wherein the HIV gp140 protein comprises the amino acid sequence of SEQ ID NO: 2.

11. The immunogenic composition of claim 1, comprising a mixture of an HIV gp140 protein comprising the amino acid sequence of SEQ ID NO: 1 and an HIV gp140 protein comprising the amino acid sequence of SEQ NO: 2.

12. The immunogenic composition of claim 1, which is stable upon storage at 2-8° C. for at least six months.

13. The immunogenic composition of claim 1, being a liquid composition.

14. The immunogenic composition of claim 8, wherein the aluminum phosphate adjuvant is present at 0.7-5.0 mg/mL.

15. The immunogenic composition of claim 8, wherein the HIV gp140 protein upon storage for one week at 40° C. is not degraded by more than 25% as measured by SDS-PAGE.

16. An immunogenic composition comprising, relative to the total volume of the composition,
   a. 0.2 mg/mL or 1 mg/mL of an HIV gp140 protein comprising the amino acid sequence of SEQ ID NO: 1 or SEQ ID NO: 2 or of a mixture of an HIV gp140 protein comprising the amino acid sequence of SEQ ID NO: 1 and an HIV gp140 protein comprising the amino acid sequence of SEQ NO: 2;
   b. 5% or 12% (w/v) sorbitol;
   c. 0.02% (w/v) polysorbate 20;
   d. 10 mM histidine buffer at a pH of 6.5; and
   e. aluminum phosphate adjuvant.

17. The immunogenic composition of claim 16, being a liquid composition.

18. The immunogenic composition of claim 16, comprising the aluminum phosphate adjuvant at 0.85 mg/mL or 3.84 mg/mL.

19. A method of preparing an immunogenic composition comprising admixing:
   a. 0.05 mg/mL to 5 mg/mL of an HIV gp140 protein or of at least two HIV gp140 proteins;
   b. 2% to 15% (w/v) sorbitol;
   c. 0.01 to 0.05% polysorbate 20; and
   d. 5 to 20 mM histidine buffer at a pH of 5.5 to 7.0;
to thereby obtain the immunogenic composition.

20. A method according to claim 19, further comprising admixing: aluminum phosphate adjuvant.

21. A method for preparing a long-term, storage stable immunogenic composition that comprises HIV gp140 protein, the method comprising: (i) providing an immunogenic composition according to claim 1, and (ii) storing said composition at 2-8° C. for at least one week.

22. The method of claim 20, wherein the aluminum phosphate adjuvant is mixed to a concentration of 0.7-5.0 mg/mL.

23. A method of inducing an immune response against HIV in a subject, the method comprising administering to the subject an immunogenic composition according to claim 1, wherein the immunogenic composition prior to said administering has been stored at 2-8° C. for one day to 36 months.

24. A method of inducing an immune response against HIV in a subject, the method comprising administering to the subject an immunogenic composition according to claim 16, wherein the immunogenic composition prior to said administering has been stored at 2-8° C. for one day to 36 months.

* * * * *

SEQUENCE LISTING

```
<160> NUMBER OF SEQ ID NOS: 14

<210> SEQ ID NO 1
<211> LENGTH: 679
<212> TYPE: PRT
<213> ORGANISM: Artificial Sequence
<220> FEATURE:
<223> OTHER INFORMATION: HIV clade C gp140 protein

<400> SEQUENCE: 1

Ala Glu Asn Leu Trp Val Gly Asn Met Trp Val Thr Val Tyr Tyr Gly
1               5                   10                  15

Val Pro Val Trp Thr Asp Ala Lys Thr Thr Leu Phe Cys Ala Ser Asp
            20                  25                  30

Thr Lys Ala Tyr Asp Arg Glu Val His Asn Val Trp Ala Thr His Ala
        35                  40                  45

Cys Val Pro Thr Asp Pro Asn Pro Gln Glu Ile Val Leu Glu Asn Val
    50                  55                  60

Thr Glu Asn Phe Asn Met Trp Lys Asn Asp Met Val Asp Gln Met His
65                  70                  75                  80

Glu Asp Ile Ile Ser Leu Trp Asp Gln Ser Leu Lys Pro Cys Val Lys
                85                  90                  95

Leu Thr Pro Leu Cys Val Thr Leu His Cys Thr Asn Ala Thr Phe Lys
            100                 105                 110

Asn Asn Val Thr Asn Asp Met Asn Lys Glu Ile Arg Asn Cys Ser Phe
        115                 120                 125

Asn Thr Thr Thr Glu Ile Arg Asp Lys Lys Gln Gln Gly Tyr Ala Leu
    130                 135                 140

Phe Tyr Arg Pro Asp Ile Val Leu Leu Lys Glu Asn Arg Asn Asn Ser
145                 150                 155                 160

Asn Asn Ser Glu Tyr Ile Leu Ile Asn Cys Asn Ala Ser Thr Ile Thr
                165                 170                 175

Gln Ala Cys Pro Lys Val Asn Phe Asp Pro Ile Pro Ile His Tyr Cys
            180                 185                 190

Ala Pro Ala Gly Tyr Ala Ile Leu Lys Cys Asn Asn Lys Thr Phe Ser
        195                 200                 205

Gly Lys Gly Pro Cys Asn Asn Val Ser Thr Val Gln Cys Thr His Gly
```

-continued

```
                210                 215                 220
Ile Lys Pro Val Val Ser Thr Gln Leu Leu Asn Gly Ser Leu Ala
225                 230                 235                 240

Glu Lys Glu Ile Ile Ile Arg Ser Glu Asn Leu Thr Asp Asn Val Lys
                245                 250                 255

Thr Ile Ile Val His Leu Asn Lys Ser Val Glu Ile Val Cys Thr Arg
                260                 265                 270

Pro Asn Asn Asn Thr Arg Lys Ser Met Arg Ile Gly Pro Gly Gln Thr
            275                 280                 285

Phe Tyr Ala Thr Gly Asp Ile Ile Gly Asp Ile Arg Gln Ala Tyr Cys
            290                 295                 300

Asn Ile Ser Gly Ser Lys Trp Asn Glu Thr Leu Lys Arg Val Lys Glu
305                 310                 315                 320

Lys Leu Gln Glu Asn Tyr Asn Asn Asn Lys Thr Ile Lys Phe Ala Pro
                325                 330                 335

Ser Ser Gly Gly Asp Leu Glu Ile Thr Thr His Ser Phe Asn Cys Arg
            340                 345                 350

Gly Glu Phe Phe Tyr Cys Asn Thr Thr Arg Leu Phe Asn Asn Asn Ala
            355                 360                 365

Thr Glu Asp Glu Thr Ile Thr Leu Pro Cys Arg Ile Lys Gln Ile Ile
370                 375                 380

Asn Met Trp Gln Gly Val Gly Arg Ala Met Tyr Ala Pro Pro Ile Ala
385                 390                 395                 400

Gly Asn Ile Thr Cys Lys Ser Asn Ile Thr Gly Leu Leu Leu Val Arg
            405                 410                 415

Asp Gly Gly Glu Asp Asn Lys Thr Glu Glu Ile Phe Arg Pro Gly Gly
            420                 425                 430

Gly Asn Met Lys Asp Asn Trp Arg Ser Glu Leu Tyr Lys Tyr Lys Val
            435                 440                 445

Ile Glu Leu Lys Pro Leu Gly Ile Ala Pro Thr Gly Ala Lys Glu Arg
            450                 455                 460

Val Val Glu Arg Glu Glu Arg Ala Val Gly Ile Gly Ala Val Phe Leu
465                 470                 475                 480

Gly Phe Leu Gly Ala Ala Gly Ser Thr Met Gly Ala Ala Ser Leu Thr
                485                 490                 495

Leu Thr Val Gln Ala Arg Gln Leu Leu Ser Ser Ile Val Gln Gln Gln
            500                 505                 510

Ser Asn Leu Leu Arg Ala Ile Glu Ala Gln Gln His Met Leu Gln Leu
            515                 520                 525

Thr Val Trp Gly Ile Lys Gln Leu Gln Thr Arg Val Leu Ala Ile Glu
530                 535                 540

Arg Tyr Leu Lys Asp Gln Gln Leu Leu Gly Ile Trp Gly Cys Ser Gly
545                 550                 555                 560

Lys Leu Ile Cys Thr Thr Asn Val Pro Trp Asn Ser Ser Trp Ser Asn
                565                 570                 575

Lys Ser Gln Thr Asp Ile Trp Asn Asn Met Thr Trp Met Glu Trp Asp
            580                 585                 590

Arg Glu Ile Ser Asn Tyr Thr Asp Thr Ile Tyr Arg Leu Leu Glu Asp
            595                 600                 605

Ser Gln Thr Gln Gln Glu Lys Asn Glu Lys Asp Leu Leu Ala Leu Asp
            610                 615                 620

Ser Trp Lys Asn Leu Trp Ser Trp Phe Asp Ile Ser Asn Trp Leu Trp
625                 630                 635                 640
```

```
Tyr Ile Lys Ser Arg Ile Glu Gly Arg Gly Ser Gly Tyr Ile Pro
            645                 650                 655

Glu Ala Pro Arg Asp Gly Gln Ala Tyr Val Arg Lys Asp Gly Glu Trp
        660                 665                 670

Val Leu Leu Ser Thr Phe Leu
        675

<210> SEQ ID NO 2
<211> LENGTH: 695
<212> TYPE: PRT
<213> ORGANISM: Artificial Sequence
<220> FEATURE:
<223> OTHER INFORMATION: HIV mosaic gp140 protein

<400> SEQUENCE: 2

Ala Gly Lys Leu Trp Val Thr Val Tyr Tyr Gly Val Pro Val Trp Lys
1               5                   10                  15

Glu Ala Thr Thr Thr Leu Phe Cys Ala Ser Asp Ala Lys Ala Tyr Asp
            20                  25                  30

Thr Glu Val His Asn Val Trp Ala Thr His Ala Cys Val Pro Thr Asp
        35                  40                  45

Pro Asn Pro Gln Glu Val Val Leu Glu Asn Val Thr Glu Asn Phe Asn
    50                  55                  60

Met Trp Lys Asn Asn Met Val Glu Gln Met His Glu Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Asn Cys Thr Asp Asp Val Arg Asn Val Thr Asn Asn Ala
            100                 105                 110

Thr Asn Thr Asn Ser Ser Trp Gly Glu Pro Met Glu Lys Gly Glu Ile
        115                 120                 125

Lys Asn Cys Ser Phe Asn Ile Thr Thr Ser Ile Arg Asn Lys Val Gln
    130                 135                 140

Lys Gln Tyr Ala Leu Phe Tyr Lys Leu Asp Val Val Pro Ile Asp Asn
145                 150                 155                 160

Asp Ser Asn Asn Thr Asn Tyr Arg Leu Ile Ser Cys Asn Thr Ser Val
                165                 170                 175

Ile Thr Gln Ala Cys Pro Lys Val Ser Phe Glu Pro Ile Pro Ile His
            180                 185                 190

Tyr Cys Ala Pro Ala Gly Phe Ala Ile Leu Lys Cys Asn Asp Lys Lys
        195                 200                 205

Phe Asn Gly Thr Gly Pro Cys Thr Asn Val Ser Thr Val Gln Cys Thr
    210                 215                 220

His Gly Ile Arg Pro Val Val Ser Thr Gln Leu Leu Asn Gly Ser
225                 230                 235                 240

Leu Ala Glu Glu Glu Val Val Ile Arg Ser Glu Asn Phe Thr Asn Asn
                245                 250                 255

Ala Lys Thr Ile Met Val Gln Leu Asn Val Ser Val Glu Ile Asn Cys
            260                 265                 270

Thr Arg Pro Asn Asn Asn Thr Arg Lys Ser Ile His Ile Gly Pro Gly
        275                 280                 285

Arg Ala Phe Tyr Thr Ala Gly Asp Ile Ile Gly Asp Ile Arg Gln Ala
    290                 295                 300

His Cys Asn Ile Ser Arg Ala Asn Trp Asn Asn Thr Leu Arg Gln Ile
305                 310                 315                 320
```

Val Glu Lys Leu Gly Lys Gln Phe Gly Asn Asn Lys Thr Ile Val Phe
                325                 330                 335

Asn His Ser Ser Gly Gly Asp Pro Glu Ile Val Met His Ser Phe Asn
            340                 345                 350

Cys Gly Gly Glu Phe Phe Tyr Cys Asn Ser Thr Lys Leu Phe Asn Ser
        355                 360                 365

Thr Trp Thr Trp Asn Asn Ser Thr Trp Asn Asn Thr Lys Arg Ser Asn
370                 375                 380

Asp Thr Glu Glu His Ile Thr Leu Pro Cys Arg Ile Lys Gln Ile Ile
385                 390                 395                 400

Asn Met Trp Gln Glu Val Gly Lys Ala Met Tyr Ala Pro Pro Ile Arg
                405                 410                 415

Gly Gln Ile Arg Cys Ser Ser Asn Ile Thr Gly Leu Leu Leu Thr Arg
            420                 425                 430

Asp Gly Gly Asn Asp Thr Ser Gly Thr Glu Ile Phe Arg Pro Gly Gly
        435                 440                 445

Gly Asp Met Arg Asp Asn Trp Arg Ser Glu Leu Tyr Lys Tyr Lys Val
    450                 455                 460

Val Lys Ile Glu Pro Leu Gly Val Ala Pro Thr Lys Ala Lys Glu Arg
465                 470                 475                 480

Val Val Gln Arg Glu Glu Arg Ala Val Gly Ile Gly Ala Val Phe Leu
                485                 490                 495

Gly Phe Leu Gly Ala Ala Gly Ser Thr Met Gly Ala Ala Ser Met Thr
            500                 505                 510

Leu Thr Val Gln Ala Arg Leu Leu Leu Ser Gly Ile Val Gln Gln Gln
        515                 520                 525

Asn Asn Leu Leu Arg Ala Ile Glu Ala Gln Gln His Leu Leu Gln Leu
530                 535                 540

Thr Val Trp Gly Ile Lys Gln Leu Gln Ala Arg Val Leu Ala Val Glu
545                 550                 555                 560

Arg Tyr Leu Lys Asp Gln Gln Leu Leu Gly Ile Trp Gly Cys Ser Gly
                565                 570                 575

Lys Leu Ile Cys Thr Thr Thr Val Pro Trp Asn Ala Ser Trp Ser Asn
            580                 585                 590

Lys Ser Leu Asp Lys Ile Trp Asn Asn Met Thr Trp Met Glu Trp Glu
        595                 600                 605

Arg Glu Ile Asn Asn Tyr Thr Ser Leu Ile Tyr Thr Leu Ile Glu Glu
    610                 615                 620

Ser Gln Asn Gln Gln Glu Lys Asn Glu Gln Glu Leu Leu Glu Leu Asp
625                 630                 635                 640

Lys Trp Ala Ser Leu Trp Asn Trp Phe Asp Ile Ser Asn Trp Leu Trp
                645                 650                 655

Tyr Ile Lys Ser Arg Ile Glu Gly Arg Gly Ser Gly Gly Tyr Ile Pro
            660                 665                 670

Glu Ala Pro Arg Asp Gly Gln Ala Tyr Val Arg Lys Asp Gly Glu Trp
        675                 680                 685

Val Leu Leu Ser Thr Phe Leu
    690                 695

<210> SEQ ID NO 3
<211> LENGTH: 660
<212> TYPE: PRT
<213> ORGANISM: Artificial Sequence
<220> FEATURE:

<223> OTHER INFORMATION: Mos1Env mosaic HIV antigen

<400> SEQUENCE: 3

```
Met Arg Val Thr Gly Ile Arg L

```
Trp Asn Asn Ser Thr Trp Asn Asn Thr Lys Arg Ser Asn Asp Thr Glu
                405                 410                 415

Glu His Ile Thr Leu Pro Cys Arg Ile Lys Gln Ile Ile Asn Met Trp
            420                 425                 430

Gln Glu Val Gly Lys Ala Met Tyr Ala Pro Pro Ile Arg Gly Gln Ile
        435                 440                 445

Arg Cys Ser Ser Asn Ile Thr Gly Leu Leu Leu Thr Arg Asp Gly Gly
    450                 455                 460

Asn Asp Thr Ser Gly Thr Glu Ile Phe Arg Pro Gly Gly Gly Asp Met
465                 470                 475                 480

Arg Asp Asn Trp Arg Ser Glu Leu Tyr Lys Tyr Lys Val Val Lys Ile
            485                 490                 495

Glu Pro Leu Gly Val Ala Pro Thr Lys Ala Lys Arg Arg Val Val Gln
        500                 505                 510

Ser Glu Lys Ser Ala Val Gly Ile Gly Ala Val Phe Leu Gly Phe Leu
    515                 520                 525

Gly Ala Ala Gly Ser Thr Met Gly Ala Ala Ser Met Thr Leu Thr Val
530                 535                 540

Gln Ala Arg Leu Leu Leu Ser Gly Ile Val Gln Gln Gln Asn Asn Leu
545                 550                 555                 560

Leu Arg Ala Ile Glu Ala Gln Gln His Leu Leu Gln Leu Thr Val Trp
            565                 570                 575

Gly Ile Lys Gln Leu Gln Ala Arg Val Leu Ala Val Glu Arg Tyr Leu
        580                 585                 590

Lys Asp Gln Gln Leu Leu Gly Ile Trp Gly Cys Ser Gly Lys Leu Ile
    595                 600                 605

Cys Thr Thr Thr Val Pro Trp Asn Ala Ser Trp Ser Asn Lys Ser Leu
610                 615                 620

Asp Lys Ile Trp Asn Asn Met Thr Trp Met Glu Trp Glu Arg Glu Ile
625                 630                 635                 640

Asn Asn Tyr Thr Ser Leu Ile Tyr Thr Leu Ile Glu Glu Ser Gln Asn
            645                 650                 655

Gln Gln Glu Lys
            660

<210> SEQ ID NO 4
<211> LENGTH: 684
<212> TYPE: PRT
<213> ORGANISM: Artificial Sequence
<220> FEATURE:
<223> OTHER INFORMATION: Mos2Env mosaic HIV antigen

<400> SEQUENCE: 4

Met Arg Val Arg Gly Ile Gln Arg Asn Trp Pro Gln Trp Trp Ile Trp
1               5                   10                  15

Gly Ile Leu Gly Phe Trp Met Ile Ile Ile Cys Arg Val Met Gly Asn
            20                  25                  30

Leu Trp Val Thr Val Tyr Tyr Gly Val Pro Val Trp Lys Glu Ala Lys
        35                  40                  45

Thr Thr Leu Phe Cys Ala Ser Asp Ala Lys Ala Tyr Glu Lys Glu Val
    50                  55                  60

His Asn Val Trp Ala Thr His Ala Cys Val Pro Thr Asp Pro Asn Pro
65                  70                  75                  80

Gln Glu Met Val Leu Glu Asn Val Thr Glu Asn Phe Asn Met Trp Lys
                85                  90                  95
```

```
Asn Asp Met Val Asp Gln Met His Glu Asp Ile Ile Arg Leu Trp Asp
            100                 105                 110
Gln Ser Leu Lys Pro Cys Val Lys Leu Thr Pro Leu Cys Val Thr Leu
        115                 120                 125
Glu Cys Arg Asn Val Arg Asn Val Ser Ser Asn Gly Thr Tyr Asn Ile
    130                 135                 140
Ile His Asn Glu Thr Tyr Lys Glu Met Lys Asn Cys Ser Phe Asn Ala
145                 150                 155                 160
Thr Thr Val Val Glu Asp Arg Lys Gln Lys Val His Ala Leu Phe Tyr
                165                 170                 175
Arg Leu Asp Ile Val Pro Leu Asp Glu Asn Asn Ser Ser Glu Lys Ser
            180                 185                 190
Ser Glu Asn Ser Ser Glu Tyr Tyr Arg Leu Ile Asn Cys Asn Thr Ser
        195                 200                 205
Ala Ile Thr Gln Ala Cys Pro Lys Val Ser Phe Asp Pro Ile Pro Ile
    210                 215                 220
His Tyr Cys Ala Pro Ala Gly Tyr Ala Ile Leu Lys Cys Asn Asn Lys
225                 230                 235                 240
Thr Phe Asn Gly Thr Gly Pro Cys Asn Asn Val Ser Thr Val Gln Cys
                245                 250                 255
Thr His Gly Ile Lys Pro Val Val Ser Thr Gln Leu Leu Leu Asn Gly
            260                 265                 270
Ser Leu Ala Glu Glu Ile Ile Ile Arg Ser Glu Asn Leu Thr Asn
        275                 280                 285
Asn Ala Lys Thr Ile Ile Val His Leu Asn Glu Thr Val Asn Ile Thr
    290                 295                 300
Cys Thr Arg Pro Asn Asn Asn Thr Arg Lys Ser Ile Arg Ile Gly Pro
305                 310                 315                 320
Gly Gln Thr Phe Tyr Ala Thr Gly Asp Ile Ile Gly Asp Ile Arg Gln
                325                 330                 335
Ala His Cys Asn Leu Ser Arg Asp Gly Trp Asn Lys Thr Leu Gln Gly
            340                 345                 350
Val Lys Lys Lys Leu Ala Glu His Phe Pro Asn Lys Thr Ile Asn Phe
        355                 360                 365
Thr Ser Ser Ser Gly Gly Asp Leu Glu Ile Thr Thr His Ser Phe Asn
    370                 375                 380
Cys Arg Gly Glu Phe Phe Tyr Cys Asn Thr Ser Gly Leu Phe Asn Gly
385                 390                 395                 400
Thr Tyr Met Pro Asn Gly Thr Asn Ser Asn Ser Ser Asn Ile Thr
                405                 410                 415
Leu Pro Cys Arg Ile Lys Gln Ile Ile Asn Met Trp Gln Glu Val Gly
            420                 425                 430
Arg Ala Met Tyr Ala Pro Pro Ile Ala Gly Asn Ile Thr Cys Arg Ser
        435                 440                 445
Asn Ile Thr Gly Leu Leu Leu Thr Arg Asp Gly Gly Ser Asn Asn Gly
    450                 455                 460
Val Pro Asn Asp Thr Glu Thr Phe Arg Pro Gly Gly Gly Asp Met Arg
465                 470                 475                 480
Asn Asn Trp Arg Ser Glu Leu Tyr Lys Tyr Lys Val Val Glu Val Lys
                485                 490                 495
Pro Leu Gly Val Ala Pro Thr Glu Ala Lys Arg Arg Val Val Glu Ser
            500                 505                 510
Glu Lys Ser Ala Val Gly Ile Gly Ala Val Phe Leu Gly Ile Leu Gly
```

```
            515                 520                 525
Ala Ala Gly Ser Thr Met Gly Ala Ala Ser Ile Thr Leu Thr Val Gln
        530                 535                 540

Ala Arg Gln Leu Leu Ser Gly Ile Val Gln Gln Ser Asn Leu Leu
545                 550                 555                 560

Arg Ala Ile Glu Ala Gln Gln His Met Leu Gln Leu Thr Val Trp Gly
                565                 570                 575

Ile Lys Gln Leu Gln Thr Arg Val Leu Ala Ile Glu Arg Tyr Leu Gln
            580                 585                 590

Asp Gln Gln Leu Leu Gly Leu Trp Gly Cys Ser Gly Lys Leu Ile Cys
        595                 600                 605

Thr Thr Ala Val Pro Trp Asn Thr Ser Trp Ser Asn Lys Ser Gln Thr
        610                 615                 620

Asp Ile Trp Asp Asn Met Thr Trp Met Gln Trp Asp Lys Glu Ile Gly
625                 630                 635                 640

Asn Tyr Thr Gly Glu Ile Tyr Arg Leu Leu Glu Glu Ser Gln Asn Gln
                645                 650                 655

Gln Glu Lys Asn Glu Lys Asp Leu Leu Ala Leu Asp Ser Trp Lys Asn
            660                 665                 670

Leu Trp Asn Trp Phe Asp Ile Thr Asn Trp Leu Trp
        675                 680

<210> SEQ ID NO 5
<211> LENGTH: 840
<212> TYPE: PRT
<213> ORGANISM: Artificial Sequence
<220> FEATURE:
<223> OTHER INFORMATION: Mos1Pol mosaic HIV antigen

<400> SEQUENCE: 5

Met Ala Pro Ile Ser Pro Ile Glu Thr Val Pro Val Lys Leu Lys Pro
1               5                   10                  15

Gly Met Asp Gly Pro Arg Val Lys Gln Trp Pro Leu Thr Glu Glu Lys
            20                  25                  30

Ile Lys Ala Leu Thr Ala Ile Cys Glu Glu Met Glu Lys Glu Gly Lys
        35                  40                  45

Ile Thr Lys Ile Gly Pro Glu Asn Pro Tyr Asn Thr Pro Val Phe Ala
    50                  55                  60

Ile Lys Lys Lys Asp Ser Thr Lys Trp Arg Lys Leu Val Asp Phe Arg
65                  70                  75                  80

Glu Leu Asn Lys Arg Thr Gln Asp Phe Trp Glu Val Gln Leu Gly Ile
                85                  90                  95

Pro His Pro Ala Gly Leu Lys Lys Lys Ser Val Thr Val Leu Ala
            100                 105                 110

Val Gly Asp Ala Tyr Phe Ser Val Pro Leu Asp Glu Gly Phe Arg Lys
        115                 120                 125

Tyr Thr Ala Phe Thr Ile Pro Ser Thr Asn Asn Glu Thr Pro Gly Ile
    130                 135                 140

Arg Tyr Gln Tyr Asn Val Leu Pro Gln Gly Trp Lys Gly Ser Pro Ala
145                 150                 155                 160

Ile Phe Gln Cys Ser Met Thr Arg Ile Leu Glu Pro Phe Arg Ala Lys
                165                 170                 175

Asn Pro Glu Ile Val Ile Tyr Gln Tyr Met Ala Ala Leu Tyr Val Gly
            180                 185                 190

Ser Asp Leu Glu Ile Gly Gln His Arg Ala Lys Ile Glu Glu Leu Arg
```

```
              195                 200                 205
Glu His Leu Leu Lys Trp Gly Phe Thr Thr Pro Asp Lys Lys His Gln
    210                 215                 220
Lys Glu Pro Pro Phe Leu Trp Met Gly Tyr Glu Leu His Pro Asp Lys
225                 230                 235                 240
Trp Thr Val Gln Pro Ile Gln Leu Pro Glu Lys Asp Ser Trp Thr Val
                245                 250                 255
Asn Asp Ile Gln Lys Leu Val Gly Lys Leu Asn Trp Ala Ser Gln Ile
            260                 265                 270
Tyr Pro Gly Ile Lys Val Arg Gln Leu Cys Lys Leu Leu Arg Gly Ala
        275                 280                 285
Lys Ala Leu Thr Asp Ile Val Pro Leu Thr Glu Glu Ala Glu Leu Glu
290                 295                 300
Leu Ala Glu Asn Arg Glu Ile Leu Lys Glu Pro Val His Gly Val Tyr
305                 310                 315                 320
Tyr Asp Pro Ser Lys Asp Leu Ile Ala Glu Ile Gln Lys Gln Gly His
                325                 330                 335
Asp Gln Trp Thr Tyr Gln Ile Tyr Gln Glu Pro Phe Lys Asn Leu Lys
            340                 345                 350
Thr Gly Lys Tyr Ala Lys Met Arg Thr Ala His Thr Asn Asp Val Lys
        355                 360                 365
Gln Leu Thr Glu Ala Val Gln Lys Ile Ala Met Glu Ser Ile Val Ile
370                 375                 380
Trp Gly Lys Thr Pro Lys Phe Arg Leu Pro Ile Gln Lys Glu Thr Trp
385                 390                 395                 400
Glu Thr Trp Trp Thr Asp Tyr Trp Gln Ala Thr Trp Ile Pro Glu Trp
                405                 410                 415
Glu Phe Val Asn Thr Pro Pro Leu Val Lys Leu Trp Tyr Gln Leu Glu
            420                 425                 430
Lys Asp Pro Ile Ala Gly Val Glu Thr Phe Tyr Val Ala Gly Ala Ala
        435                 440                 445
Asn Arg Glu Thr Lys Leu Gly Lys Ala Gly Tyr Val Thr Asp Arg Gly
450                 455                 460
Arg Gln Lys Ile Val Ser Leu Thr Glu Thr Thr Asn Gln Lys Thr Ala
465                 470                 475                 480
Leu Gln Ala Ile Tyr Leu Ala Leu Gln Asp Ser Gly Ser Glu Val Asn
                485                 490                 495
Ile Val Thr Ala Ser Gln Tyr Ala Leu Gly Ile Ile Gln Ala Gln Pro
            500                 505                 510
Asp Lys Ser Glu Ser Glu Leu Val Asn Gln Ile Ile Glu Gln Leu Ile
        515                 520                 525
Lys Lys Glu Arg Val Tyr Leu Ser Trp Val Pro Ala His Lys Gly Ile
530                 535                 540
Gly Gly Asn Glu Gln Val Asp Lys Leu Val Ser Ser Gly Ile Arg Lys
545                 550                 555                 560
Val Leu Phe Leu Asp Gly Ile Asp Lys Ala Gln Glu Glu His Glu Lys
                565                 570                 575
Tyr His Ser Asn Trp Arg Ala Met Ala Ser Asp Phe Asn Leu Pro Pro
            580                 585                 590
Val Val Ala Lys Glu Ile Val Ala Ser Cys Asp Gln Cys Gln Leu Lys
        595                 600                 605
Gly Glu Ala Met His Gly Gln Val Asp Cys Ser Pro Gly Ile Trp Gln
610                 615                 620
```

```
Leu Ala Cys Thr His Leu Glu Gly Lys Ile Ile Leu Val Ala Val His
625                 630                 635                 640

Val Ala Ser Gly Tyr Ile Glu Ala Glu Val Ile Pro Ala Glu Thr Gly
            645                 650                 655

Gln Glu Thr Ala Tyr Phe Ile Leu Lys Leu Ala Gly Arg Trp Pro Val
        660                 665                 670

Lys Val Ile His Thr Ala Asn Gly Ser Asn Phe Thr Ser Ala Ala Val
    675                 680                 685

Lys Ala Ala Cys Trp Trp Ala Gly Ile Gln Gln Glu Phe Gly Ile Pro
690                 695                 700

Tyr Asn Pro Gln Ser Gln Gly Val Val Ala Ser Met Asn Lys Glu Leu
705                 710                 715                 720

Lys Lys Ile Ile Gly Gln Val Arg Asp Gln Ala Glu His Leu Lys Thr
            725                 730                 735

Ala Val Gln Met Ala Val Phe Ile His Asn Phe Lys Arg Lys Gly Gly
        740                 745                 750

Ile Gly Gly Tyr Ser Ala Gly Glu Arg Ile Ile Asp Ile Ile Ala Thr
    755                 760                 765

Asp Ile Gln Thr Lys Glu Leu Gln Lys Gln Ile Lys Ile Gln Asn
770                 775                 780

Phe Arg Val Tyr Arg Asp Ser Arg Asp Pro Ile Trp Lys Gly Pro
785                 790                 795                 800

Ala Lys Leu Leu Trp Lys Gly Glu Gly Ala Val Val Ile Gln Asp Asn
            805                 810                 815

Ser Asp Ile Lys Val Val Pro Arg Arg Lys Val Lys Ile Ile Lys Asp
        820                 825                 830

Tyr Gly Lys Gln Met Ala Gly Ala
        835                 840

<210> SEQ ID NO 6
<211> LENGTH: 850
<212> TYPE: PRT
<213> ORGANISM: Artificial Sequence
<220> FEATURE:
<223> OTHER INFORMATION: Mos2Pol mosaic HIV antigen

<400> SEQUENCE: 6

Met Ala Pro Ile Ser Pro Ile Glu Thr Val Pro Val Lys Leu Lys Pro
1               5                   10                  15

Gly Met Asp Gly Pro Lys Val Lys Gln Trp Pro Leu Thr Glu Glu Lys
            20                  25                  30

Ile Lys Ala Leu Val Glu Ile Cys Thr Glu Met Glu Lys Glu Gly Lys
        35                  40                  45

Ile Ser Lys Ile Gly Pro Glu Asn Pro Tyr Asn Thr Pro Ile Phe Ala
    50                  55                  60

Ile Lys Lys Lys Asp Ser Thr Lys Trp Arg Lys Leu Val Asp Phe Arg
65                  70                  75                  80

Glu Leu Asn Lys Arg Thr Gln Asp Phe Trp Glu Val Gln Leu Gly Ile
                85                  90                  95

Pro His Pro Ala Gly Leu Lys Lys Lys Ser Val Thr Val Leu Ala
            100                 105                 110

Val Gly Asp Ala Tyr Phe Ser Val Pro Leu Asp Glu Asp Phe Arg Lys
        115                 120                 125

Tyr Thr Ala Phe Thr Ile Pro Ser Ile Asn Asn Glu Thr Pro Gly Ile
    130                 135                 140
```

```
Arg Tyr Gln Tyr Asn Val Leu Pro Gln Gly Trp Lys Gly Ser Pro Ala
145                 150                 155                 160

Ile Phe Gln Ser Ser Met Thr Lys Ile Leu Glu Pro Phe Arg Lys Gln
                165                 170                 175

Asn Pro Asp Ile Val Ile Tyr Gln Tyr Met Ala Ala Leu Tyr Val Gly
            180                 185                 190

Ser Asp Leu Glu Ile Gly Gln His Arg Thr Lys Ile Glu Glu Leu Arg
        195                 200                 205

Gln His Leu Leu Arg Trp Gly Phe Thr Thr Pro Asp Lys Lys His Gln
    210                 215                 220

Lys Glu Pro Pro Phe Leu Trp Met Gly Tyr Glu Leu His Pro Asp Lys
225                 230                 235                 240

Trp Thr Val Gln Pro Ile Val Leu Pro Glu Lys Asp Ser Trp Thr Val
                245                 250                 255

Asn Asp Ile Gln Lys Leu Val Gly Lys Leu Asn Trp Ala Ser Gln Ile
            260                 265                 270

Tyr Ala Gly Ile Lys Val Lys Gln Leu Cys Lys Leu Leu Arg Gly Thr
        275                 280                 285

Lys Ala Leu Thr Glu Val Val Pro Leu Thr Glu Glu Ala Glu Leu Glu
    290                 295                 300

Leu Ala Glu Asn Arg Glu Ile Leu Lys Glu Pro Val His Gly Val Tyr
305                 310                 315                 320

Tyr Asp Pro Ser Lys Asp Leu Ile Ala Glu Ile Gln Lys Gln Gly Gln
                325                 330                 335

Gly Gln Trp Thr Tyr Gln Ile Tyr Gln Glu Pro Phe Lys Asn Leu Lys
            340                 345                 350

Thr Gly Lys Tyr Ala Arg Met Arg Gly Ala His Thr Asn Asp Val Lys
        355                 360                 365

Gln Leu Thr Glu Ala Val Gln Lys Ile Ala Thr Glu Ser Ile Val Ile
    370                 375                 380

Trp Gly Lys Thr Pro Lys Phe Lys Leu Pro Ile Gln Lys Glu Thr Trp
385                 390                 395                 400

Glu Ala Trp Trp Thr Glu Tyr Trp Gln Ala Thr Trp Ile Pro Glu Trp
                405                 410                 415

Glu Phe Val Asn Thr Pro Pro Leu Val Lys Leu Trp Tyr Gln Leu Glu
            420                 425                 430

Lys Glu Pro Ile Val Gly Ala Glu Thr Phe Tyr Val Ala Gly Ala Ala
        435                 440                 445

Asn Arg Glu Thr Lys Leu Gly Lys Ala Gly Tyr Val Thr Asp Arg Gly
    450                 455                 460

Arg Gln Lys Val Val Ser Leu Thr Asp Thr Thr Asn Gln Lys Thr Ala
465                 470                 475                 480

Leu Gln Ala Ile His Leu Ala Leu Gln Asp Ser Gly Leu Glu Val Asn
                485                 490                 495

Ile Val Thr Ala Ser Gln Tyr Ala Leu Gly Ile Ile Gln Ala Gln Pro
            500                 505                 510

Asp Lys Ser Glu Ser Glu Leu Val Ser Gln Ile Ile Glu Gln Leu Ile
        515                 520                 525

Lys Lys Glu Lys Val Tyr Leu Ala Trp Val Pro Ala His Lys Gly Ile
    530                 535                 540

Gly Gly Asn Glu Gln Val Asp Lys Leu Val Ser Arg Gly Ile Arg Lys
545                 550                 555                 560
```

```
Val Leu Phe Leu Asp Gly Ile Asp Lys Ala Gln Glu Glu His Glu Lys
                565                 570                 575

Tyr His Ser Asn Trp Arg Ala Met Ala Ser Glu Phe Asn Leu Pro Pro
            580                 585                 590

Ile Val Ala Lys Glu Ile Val Ala Ser Cys Asp Lys Cys Gln Leu Lys
        595                 600                 605

Gly Glu Ala Ile His Gly Gln Val Asp Cys Ser Pro Gly Ile Trp Gln
    610                 615                 620

Leu Ala Cys Thr His Leu Glu Gly Lys Val Ile Leu Val Ala Val His
625                 630                 635                 640

Val Ala Ser Gly Tyr Ile Glu Ala Glu Val Ile Pro Ala Glu Thr Gly
                645                 650                 655

Gln Glu Thr Ala Tyr Phe Leu Leu Lys Leu Ala Gly Arg Trp Pro Val
            660                 665                 670

Lys Thr Ile His Thr Ala Asn Gly Ser Asn Phe Thr Ser Ala Thr Val
        675                 680                 685

Lys Ala Ala Cys Trp Trp Ala Gly Ile Lys Gln Glu Phe Gly Ile Pro
    690                 695                 700

Tyr Asn Pro Gln Ser Gln Gly Val Val Ala Ser Ile Asn Lys Glu Leu
705                 710                 715                 720

Lys Lys Ile Ile Gly Gln Val Arg Asp Gln Ala Glu His Leu Lys Thr
                725                 730                 735

Ala Val Gln Met Ala Val Phe Ile His Asn Phe Lys Arg Lys Gly Gly
            740                 745                 750

Ile Gly Glu Tyr Ser Ala Gly Glu Arg Ile Val Asp Ile Ile Ala Ser
        755                 760                 765

Asp Ile Gln Thr Lys Glu Leu Gln Lys Gln Ile Thr Lys Ile Gln Asn
    770                 775                 780

Phe Arg Val Tyr Tyr Arg Asp Ser Arg Asp Pro Leu Trp Lys Gly Pro
785                 790                 795                 800

Ala Lys Leu Leu Trp Lys Gly Glu Gly Ala Val Val Ile Gln Asp Asn
                805                 810                 815

Ser Asp Ile Lys Val Val Pro Arg Arg Lys Ala Lys Ile Ile Arg Asp
            820                 825                 830

Tyr Gly Lys Gln Met Ala Gly Asp Asp Cys Val Ala Ser Arg Gln Asp
        835                 840                 845

Glu Asp
    850

<210> SEQ ID NO 7
<211> LENGTH: 500
<212> TYPE: PRT
<213> ORGANISM: Artificial Sequence
<220> FEATURE:
<223> OTHER INFORMATION: Mos1Gag mosaic HIV antigen

<400> SEQUENCE: 7

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Tyr Arg Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60
```

```
Gln Pro Ser Leu Gln Thr Gly Ser Glu Glu Leu Arg Ser Leu Tyr Asn
 65                  70                  75                  80

Thr Val Ala Thr Leu Tyr Cys Val His Gln Arg Ile Glu Ile Lys Asp
                 85                  90                  95

Thr Lys Glu Ala Leu Glu Lys Ile Glu Glu Gln Asn Lys Ser Lys
            100                 105                 110

Lys Lys Ala Gln Gln Ala Ala Ala Asp Thr Gly Asn Ser Ser Gln Val
        115                 120                 125

Ser Gln Asn Tyr Pro Ile Val Gln Asn Ile Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Val His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Val Ser Ile Leu Asp Ile Arg Gln Gly
        275                 280                 285

Pro Lys Glu Pro Phe Arg Asp Tyr Val Asp Arg Phe Tyr Lys Thr Leu
290                 295                 300

Arg Ala Glu Gln Ala Ser Gln Asp Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Val Thr Asn Ser Ala Thr Ile Met Met Gln Arg Gly Asn Phe Arg
    370                 375                 380

Asn Gln Arg Lys Thr Val Lys Cys Phe Asn Cys Gly Lys Glu Gly His
385                 390                 395                 400

Ile Ala Lys Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
            420                 425                 430

Phe Leu Gly Lys Ile Trp Pro Ser Asn Lys Gly Arg Pro Gly Asn Phe
        435                 440                 445

Leu Gln Asn Arg Pro Glu Pro Thr Ala Pro Glu Glu Ser Phe Arg
    450                 455                 460

Phe Gly Glu Glu Thr Thr Thr Pro Ser Gln Lys Gln Glu Pro Ile Asp
465                 470                 475                 480

Lys Glu Met Tyr Pro Leu Ala Ser Leu Lys Ser Leu Phe Gly Asn Asp
```

Pro Ser Ser Gln
            500

<210> SEQ ID NO 8
<211> LENGTH: 491
<212> TYPE: PRT
<213> ORGANISM: Artificial Sequence
<220> FEATURE:
<223> OTHER INFORMATION: Mos2Gag mosaic HIV antigen

<400> SEQUENCE: 8

Met Gly Ala Arg Ala Ser Ile Leu Arg Gly Gly Lys Leu Asp Lys Trp
1               5                   10                  15

Glu Lys Ile Arg Leu Arg Pro Gly Gly Lys Lys His Tyr Met Leu Lys
            20                  25                  30

His Leu Val Trp Ala Ser Arg Glu Leu Glu Arg Phe Ala Leu Asn Pro
        35                  40                  45

Gly Leu Leu Glu Thr Ser Glu Gly Cys Lys Gln Ile Ile Lys Gln Leu
    50                  55                  60

Gln Pro Ala Leu Gln Thr Gly Thr Glu Glu Leu Arg Ser Leu Phe Asn
65                  70                  75                  80

Thr Val Ala Thr Leu Tyr Cys Val His Ala Glu Ile Glu Val Arg Asp
                85                  90                  95

Thr Lys Glu Ala Leu Asp Lys Ile Glu Glu Gln Asn Lys Ser Gln
            100                 105                 110

Gln Lys Thr Gln Gln Ala Lys Glu Ala Asp Gly Lys Val Ser Gln Asn
        115                 120                 125

Tyr Pro Ile Val Gln Asn Leu Gln Gly Gln Met Val His Gln Pro Ile
    130                 135                 140

Ser Pro Arg Thr Leu Asn Ala Trp Val Lys Val Ile Glu Glu Lys Ala
145                 150                 155                 160

Phe Ser Pro Glu Val Ile Pro Met Phe Thr Ala Leu Ser Glu Gly Ala
                165                 170                 175

Thr Pro Gln Asp Leu Asn Thr Met Leu Asn Thr Val Gly Gly His Gln
            180                 185                 190

Ala Ala Met Gln Met Leu Lys Asp Thr Ile Asn Glu Glu Ala Ala Glu
        195                 200                 205

Trp Asp Arg Leu His Pro Val His Ala Gly Pro Val Ala Pro Gly Gln
    210                 215                 220

Met Arg Glu Pro Arg Gly Ser Asp Ile Ala Gly Thr Thr Ser Asn Leu
225                 230                 235                 240

Gln Glu Gln Ile Ala Trp Met Thr Ser Asn Pro Pro Ile Pro Val Gly
                245                 250                 255

Asp Ile Tyr Lys Arg Trp Ile Ile Leu Gly Leu Asn Lys Ile Val Arg
            260                 265                 270

Met Tyr Ser Pro Thr Ser Ile Leu Asp Ile Lys Gln Gly Pro Lys Glu
        275                 280                 285

Pro Phe Arg Asp Tyr Val Asp Arg Phe Phe Lys Thr Leu Arg Ala Glu
    290                 295                 300

Gln Ala Thr Gln Asp Val Lys Asn Trp Met Thr Asp Thr Leu Leu Val
305                 310                 315                 320

Gln Asn Ala Asn Pro Asp Cys Lys Thr Ile Leu Arg Ala Leu Gly Pro
                325                 330                 335

Gly Ala Thr Leu Glu Glu Met Met Thr Ala Cys Gln Gly Val Gly Gly

```
                     340                 345                 350
Pro Ser His Lys Ala Arg Val Leu Ala Glu Ala Met Ser Gln Thr Asn
            355                 360                 365

Ser Thr Ile Leu Met Gln Arg Ser Asn Phe Lys Gly Ser Lys Arg Ile
        370                 375                 380

Val Lys Cys Phe Asn Cys Gly Lys Glu Gly His Ile Ala Arg Asn Cys
385                 390                 395                 400

Arg Ala Pro Arg Lys Lys Gly Cys Trp Lys Cys Gly Lys Glu Gly His
                405                 410                 415

Gln Met Lys Asp Cys Thr Glu Arg Gln Ala Asn Phe Leu Gly Lys Ile
            420                 425                 430

Trp Pro Ser His Lys Gly Arg Pro Gly Asn Phe Leu Gln Ser Arg Pro
        435                 440                 445

Glu Pro Thr Ala Pro Pro Ala Glu Ser Phe Arg Phe Glu Glu Thr Thr
    450                 455                 460

Pro Ala Pro Lys Gln Glu Pro Lys Asp Arg Glu Pro Leu Thr Ser Leu
465                 470                 475                 480

Arg Ser Leu Phe Gly Ser Asp Pro Leu Ser Gln
                485                 490

<210> SEQ ID NO 9
<211> LENGTH: 1350
<212> TYPE: PRT
<213> ORGANISM: Artificial Sequence
<220> FEATURE:
<223> OTHER INFORMATION: Mos1GagPol mosaic HIV antigen

<400> SEQUENCE: 9

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Lys Tyr Arg Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Glu Lys Ile Glu Glu Glu Gln Asn Lys Ser Lys
            100                 105                 110

Lys Lys Ala Gln Gln Ala Ala Ala Asp Thr Gly Asn Ser Ser Gln Val
        115                 120                 125

Ser Gln Asn Tyr Pro Ile Val Gln Asn Ile Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Val His Pro Val His Ala Gly Pro Ile Ala
```

```
            210                 215                 220
Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Val Ser Ile Leu Asp Ile Arg Gln Gly
        275                 280                 285

Pro Lys Glu Pro Phe Arg Asp Tyr Val Asp Arg Phe Tyr Lys Thr Leu
    290                 295                 300

Arg Ala Glu Gln Ala Ser Gln Asp Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Val Thr Asn Ser Ala Thr Ile Met Met Gln Arg Gly Asn Phe Arg
    370                 375                 380

Asn Gln Arg Lys Thr Val Lys Cys Phe Asn Cys Gly Lys Glu Gly His
385                 390                 395                 400

Ile Ala Lys Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
            420                 425                 430

Phe Leu Gly Lys Ile Trp Pro Ser Asn Lys Gly Arg Pro Gly Asn Phe
        435                 440                 445

Leu Gln Asn Arg Pro Glu Pro Thr Ala Pro Pro Glu Glu Ser Phe Arg
    450                 455                 460

Phe Gly Glu Glu Thr Thr Thr Pro Ser Gln Lys Gln Glu Pro Ile Asp
465                 470                 475                 480

Lys Glu Met Tyr Pro Leu Ala Ser Leu Lys Ser Leu Phe Gly Asn Asp
                485                 490                 495

Pro Ser Ser Gln Met Ala Pro Ile Ser Pro Ile Glu Thr Val Pro Val
            500                 505                 510

Lys Leu Lys Pro Gly Met Asp Gly Pro Arg Val Lys Gln Trp Pro Leu
        515                 520                 525

Thr Glu Glu Lys Ile Lys Ala Leu Thr Ala Ile Cys Glu Glu Met Glu
    530                 535                 540

Lys Glu Gly Lys Ile Thr Lys Ile Gly Pro Glu Asn Pro Tyr Asn Thr
545                 550                 555                 560

Pro Val Phe Ala Ile Lys Lys Lys Asp Ser Thr Lys Trp Arg Lys Leu
                565                 570                 575

Val Asp Phe Arg Glu Leu Asn Lys Arg Thr Gln Asp Phe Trp Glu Val
            580                 585                 590

Gln Leu Gly Ile Pro His Pro Ala Gly Leu Lys Lys Lys Ser Val
        595                 600                 605

Thr Val Leu Ala Val Gly Asp Ala Tyr Phe Ser Val Pro Leu Asp Glu
    610                 615                 620

Gly Phe Arg Lys Tyr Thr Ala Phe Thr Ile Pro Ser Thr Asn Asn Glu
625                 630                 635                 640
```

```
Thr Pro Gly Ile Arg Tyr Gln Tyr Asn Val Leu Pro Gln Gly Trp Lys
            645                 650                 655
Gly Ser Pro Ala Ile Phe Gln Cys Ser Met Thr Arg Ile Leu Glu Pro
            660                 665                 670
Phe Arg Ala Lys Asn Pro Glu Ile Val Ile Tyr Gln Tyr Met Ala Ala
            675                 680                 685
Leu Tyr Val Gly Ser Asp Leu Glu Ile Gly Gln His Arg Ala Lys Ile
            690                 695                 700
Glu Glu Leu Arg Glu His Leu Leu Lys Trp Gly Phe Thr Thr Pro Asp
705                 710                 715                 720
Lys Lys His Gln Lys Glu Pro Pro Phe Leu Trp Met Gly Tyr Glu Leu
            725                 730                 735
His Pro Asp Lys Trp Thr Val Gln Pro Ile Gln Leu Pro Glu Lys Asp
            740                 745                 750
Ser Trp Thr Val Asn Asp Ile Gln Lys Leu Val Gly Lys Leu Asn Trp
            755                 760                 765
Ala Ser Gln Ile Tyr Pro Gly Ile Lys Val Arg Gln Leu Cys Lys Leu
            770                 775                 780
Leu Arg Gly Ala Lys Ala Leu Thr Asp Ile Val Pro Leu Thr Glu Glu
785                 790                 795                 800
Ala Glu Leu Glu Leu Ala Glu Asn Arg Glu Ile Leu Lys Glu Pro Val
            805                 810                 815
His Gly Val Tyr Tyr Asp Pro Ser Lys Asp Leu Ile Ala Glu Ile Gln
            820                 825                 830
Lys Gln Gly His Asp Gln Trp Thr Tyr Gln Ile Tyr Gln Glu Pro Phe
            835                 840                 845
Lys Asn Leu Lys Thr Gly Lys Tyr Ala Lys Met Arg Thr Ala His Thr
850                 855                 860
Asn Asp Val Lys Gln Leu Thr Glu Ala Val Gln Lys Ile Ala Met Glu
865                 870                 875                 880
Ser Ile Val Ile Trp Gly Lys Thr Pro Lys Phe Arg Leu Pro Ile Gln
            885                 890                 895
Lys Glu Thr Trp Glu Thr Trp Trp Thr Asp Tyr Trp Gln Ala Thr Trp
            900                 905                 910
Ile Pro Glu Trp Glu Phe Val Asn Thr Pro Pro Leu Val Lys Leu Trp
            915                 920                 925
Tyr Gln Leu Glu Lys Asp Pro Ile Ala Gly Val Glu Thr Phe Tyr Val
            930                 935                 940
Ala Gly Ala Ala Asn Arg Glu Thr Lys Leu Gly Lys Ala Gly Tyr Val
945                 950                 955                 960
Thr Asp Arg Gly Arg Gln Lys Ile Val Ser Leu Thr Glu Thr Thr Asn
            965                 970                 975
Gln Lys Thr Ala Leu Gln Ala Ile Tyr Leu Ala Leu Gln Asp Ser Gly
            980                 985                 990
Ser Glu Val Asn Ile Val Thr Ala  Ser Gln Tyr Ala Leu  Gly Ile Ile
            995                1000                  1005
Gln Ala  Gln Pro Asp Lys Ser  Glu Ser Glu Leu Val  Asn Gln Ile
    1010                 1015                 1020
Ile Glu  Gln Leu Ile Lys Lys  Glu Arg Val Tyr Leu  Ser Trp Val
    1025                 1030                 1035
Pro Ala  His Lys Gly Ile Gly  Gly Asn Glu Gln Val  Asp Lys Leu
    1040                 1045                 1050
```

Val Ser Ser Gly Ile Arg Lys Val Leu Phe Leu Asp Gly Ile Asp
    1055                1060                1065

Lys Ala Gln Glu Glu His Glu Lys Tyr His Ser Asn Trp Arg Ala
    1070                1075                1080

Met Ala Ser Asp Phe Asn Leu Pro Pro Val Val Ala Lys Glu Ile
    1085                1090                1095

Val Ala Ser Cys Asp Gln Cys Gln Leu Lys Gly Glu Ala Met His
    1100                1105                1110

Gly Gln Val Asp Cys Ser Pro Gly Ile Trp Gln Leu Ala Cys Thr
    1115                1120                1125

His Leu Glu Gly Lys Ile Ile Leu Val Ala Val His Val Ala Ser
    1130                1135                1140

Gly Tyr Ile Glu Ala Glu Val Ile Pro Ala Glu Thr Gly Gln Glu
    1145                1150                1155

Thr Ala Tyr Phe Ile Leu Lys Leu Ala Gly Arg Trp Pro Val Lys
    1160                1165                1170

Val Ile His Thr Ala Asn Gly Ser Asn Phe Thr Ser Ala Ala Val
    1175                1180                1185

Lys Ala Ala Cys Trp Trp Ala Gly Ile Gln Gln Glu Phe Gly Ile
    1190                1195                1200

Pro Tyr Asn Pro Gln Ser Gln Gly Val Val Ala Ser Met Asn Lys
    1205                1210                1215

Glu Leu Lys Lys Ile Ile Gly Gln Val Arg Asp Gln Ala Glu His
    1220                1225                1230

Leu Lys Thr Ala Val Gln Met Ala Val Phe Ile His Asn Phe Lys
    1235                1240                1245

Arg Lys Gly Gly Ile Gly Gly Tyr Ser Ala Gly Glu Arg Ile Ile
    1250                1255                1260

Asp Ile Ile Ala Thr Asp Ile Gln Thr Lys Glu Leu Gln Lys Gln
    1265                1270                1275

Ile Ile Lys Ile Gln Asn Phe Arg Val Tyr Tyr Arg Asp Ser Arg
    1280                1285                1290

Asp Pro Ile Trp Lys Gly Pro Ala Lys Leu Leu Trp Lys Gly Glu
    1295                1300                1305

Gly Ala Val Val Ile Gln Asp Asn Ser Asp Ile Lys Val Val Pro
    1310                1315                1320

Arg Arg Lys Val Lys Ile Ile Lys Asp Tyr Gly Lys Gln Met Ala
    1325                1330                1335

Gly Ala Asp Cys Val Ala Gly Arg Gln Asp Glu Asp
    1340                1345                1350

<210> SEQ ID NO 10
<211> LENGTH: 1341
<212> TYPE: PRT
<213> ORGANISM: Artificial Sequence
<220> FEATURE:
<223> OTHER INFORMATION: Mos2GagPol mosaic HIV antigen

<400> SEQUENCE: 10

Met Gly Ala Arg Ala Ser Ile Leu Arg Gly Gly Lys Leu Asp Lys Trp
1               5                   10                  15

Glu Lys Ile Arg Leu Arg Pro Gly Gly Lys Lys His Tyr Met Leu Lys
                20                  25                  30

His Leu Val Trp Ala Ser Arg Glu Leu Glu Arg Phe Ala Leu Asn Pro
            35                  40                  45

-continued

Gly Leu Leu Glu Thr Ser Glu Gly Cys Lys Gln Ile Ile Lys Gln Leu
    50                  55                  60

Gln Pro Ala Leu Gln Thr Gly Thr Glu Leu Arg Ser Leu Phe Asn
65                  70                  75                  80

Thr Val Ala Thr Leu Tyr Cys Val His Ala Glu Ile Glu Val Arg Asp
                85                  90                  95

Thr Lys Glu Ala Leu Asp Lys Ile Glu Glu Glu Gln Asn Lys Ser Gln
            100                 105                 110

Gln Lys Thr Gln Gln Ala Lys Glu Ala Asp Gly Lys Val Ser Gln Asn
        115                 120                 125

Tyr Pro Ile Val Gln Asn Leu Gln Gly Gln Met Val His Gln Pro Ile
    130                 135                 140

Ser Pro Arg Thr Leu Asn Ala Trp Val Lys Val Ile Glu Glu Lys Ala
145                 150                 155                 160

Phe Ser Pro Glu Val Ile Pro Met Phe Thr Ala Leu Ser Glu Gly Ala
                165                 170                 175

Thr Pro Gln Asp Leu Asn Thr Met Leu Asn Thr Val Gly Gly His Gln
            180                 185                 190

Ala Ala Met Gln Met Leu Lys Asp Thr Ile Asn Glu Glu Ala Ala Glu
        195                 200                 205

Trp Asp Arg Leu His Pro Val His Ala Gly Pro Val Ala Pro Gly Gln
    210                 215                 220

Met Arg Glu Pro Arg Gly Ser Asp Ile Ala Gly Thr Thr Ser Asn Leu
225                 230                 235                 240

Gln Glu Gln Ile Ala Trp Met Thr Ser Asn Pro Pro Ile Pro Val Gly
                245                 250                 255

Asp Ile Tyr Lys Arg Trp Ile Ile Leu Gly Leu Asn Lys Ile Val Arg
            260                 265                 270

Met Tyr Ser Pro Thr Ser Ile Leu Asp Ile Lys Gln Gly Pro Lys Glu
        275                 280                 285

Pro Phe Arg Asp Tyr Val Asp Arg Phe Phe Lys Thr Leu Arg Ala Glu
    290                 295                 300

Gln Ala Thr Gln Asp Val Lys Asn Trp Met Thr Asp Thr Leu Leu Val
305                 310                 315                 320

Gln Asn Ala Asn Pro Asp Cys Lys Thr Ile Leu Arg Ala Leu Gly Pro
                325                 330                 335

Gly Ala Thr Leu Glu Glu Met Met Thr Ala Cys Gln Gly Val Gly Gly
            340                 345                 350

Pro Ser His Lys Ala Arg Val Leu Ala Glu Ala Met Ser Gln Thr Asn
        355                 360                 365

Ser Thr Ile Leu Met Gln Arg Ser Asn Phe Lys Gly Ser Lys Arg Ile
    370                 375                 380

Val Lys Cys Phe Asn Cys Gly Lys Glu Gly His Ile Ala Arg Asn Cys
385                 390                 395                 400

Arg Ala Pro Arg Lys Lys Gly Cys Trp Lys Cys Gly Lys Glu Gly His
                405                 410                 415

Gln Met Lys Asp Cys Thr Glu Arg Gln Ala Asn Phe Leu Gly Lys Ile
            420                 425                 430

Trp Pro Ser His Lys Gly Arg Pro Gly Asn Phe Leu Gln Ser Arg Pro
        435                 440                 445

Glu Pro Thr Ala Pro Pro Ala Glu Ser Phe Arg Phe Glu Glu Thr Thr
    450                 455                 460

Pro Ala Pro Lys Gln Glu Pro Lys Asp Arg Glu Pro Leu Thr Ser Leu

-continued

```
            465                 470                 475                 480
        Arg Ser Leu Phe Gly Ser Asp Pro Leu Ser Gln Met Ala Pro Ile Ser
                        485                 490                 495
        Pro Ile Glu Thr Val Pro Val Lys Leu Lys Pro Gly Met Asp Gly Pro
                    500                 505                 510
        Lys Val Lys Gln Trp Pro Leu Thr Glu Glu Lys Ile Lys Ala Leu Val
                515                 520                 525
        Glu Ile Cys Thr Glu Met Glu Lys Glu Gly Lys Ile Ser Lys Ile Gly
            530                 535                 540
        Pro Glu Asn Pro Tyr Asn Thr Pro Ile Phe Ala Ile Lys Lys Lys Asp
        545                 550                 555                 560
        Ser Thr Lys Trp Arg Lys Leu Val Asp Phe Arg Glu Leu Asn Lys Arg
                        565                 570                 575
        Thr Gln Asp Phe Trp Glu Val Gln Leu Gly Ile Pro His Pro Ala Gly
                    580                 585                 590
        Leu Lys Lys Lys Lys Ser Val Thr Val Leu Ala Val Gly Asp Ala Tyr
                595                 600                 605
        Phe Ser Val Pro Leu Asp Glu Asp Phe Arg Lys Tyr Thr Ala Phe Thr
            610                 615                 620
        Ile Pro Ser Ile Asn Asn Glu Thr Pro Gly Ile Arg Tyr Gln Tyr Asn
        625                 630                 635                 640
        Val Leu Pro Gln Gly Trp Lys Gly Ser Pro Ala Ile Phe Gln Ser Ser
                        645                 650                 655
        Met Thr Lys Ile Leu Glu Pro Phe Arg Lys Gln Asn Pro Asp Ile Val
                    660                 665                 670
        Ile Tyr Gln Tyr Met Ala Ala Leu Tyr Val Gly Ser Asp Leu Glu Ile
                675                 680                 685
        Gly Gln His Arg Thr Lys Ile Glu Glu Leu Arg Gln His Leu Leu Arg
            690                 695                 700
        Trp Gly Phe Thr Thr Pro Asp Lys Lys His Gln Lys Glu Pro Pro Phe
        705                 710                 715                 720
        Leu Trp Met Gly Tyr Glu Leu His Pro Asp Lys Trp Thr Val Gln Pro
                        725                 730                 735
        Ile Val Leu Pro Glu Lys Asp Ser Trp Thr Val Asn Asp Ile Gln Lys
                    740                 745                 750
        Leu Val Gly Lys Leu Asn Trp Ala Ser Gln Ile Tyr Ala Gly Ile Lys
                755                 760                 765
        Val Lys Gln Leu Cys Lys Leu Leu Arg Gly Thr Lys Ala Leu Thr Glu
            770                 775                 780
        Val Val Pro Leu Thr Glu Glu Ala Glu Leu Glu Leu Ala Glu Asn Arg
        785                 790                 795                 800
        Glu Ile Leu Lys Glu Pro Val His Gly Val Tyr Tyr Asp Pro Ser Lys
                        805                 810                 815
        Asp Leu Ile Ala Glu Ile Gln Lys Gln Gly Gln Gly Gln Trp Thr Tyr
                    820                 825                 830
        Gln Ile Tyr Gln Glu Pro Phe Lys Asn Leu Lys Thr Gly Lys Tyr Ala
                835                 840                 845
        Arg Met Arg Gly Ala His Thr Asn Asp Val Lys Gln Leu Thr Glu Ala
            850                 855                 860
        Val Gln Lys Ile Ala Thr Glu Ser Ile Val Ile Trp Gly Lys Thr Pro
        865                 870                 875                 880
        Lys Phe Lys Leu Pro Ile Gln Lys Glu Thr Trp Glu Ala Trp Trp Thr
                        885                 890                 895
```

```
Glu Tyr Trp Gln Ala Thr Trp Ile Pro Glu Trp Phe Val Asn Thr
            900                 905                 910

Pro Pro Leu Val Lys Leu Trp Tyr Gln Leu Glu Lys Glu Pro Ile Val
        915                 920                 925

Gly Ala Glu Thr Phe Tyr Val Ala Gly Ala Ala Asn Arg Glu Thr Lys
        930                 935                 940

Leu Gly Lys Ala Gly Tyr Val Thr Asp Arg Gly Arg Gln Lys Val Val
945                 950                 955                 960

Ser Leu Thr Asp Thr Thr Asn Gln Lys Thr Ala Leu Gln Ala Ile His
            965                 970                 975

Leu Ala Leu Gln Asp Ser Gly Leu Glu Val Asn Ile Val Thr Ala Ser
            980                 985                 990

Gln Tyr Ala Leu Gly Ile Ile Gln Ala Gln Pro Asp Lys Ser Glu Ser
            995                 1000                1005

Glu Leu Val Ser Gln Ile Ile Glu Gln Leu Ile Lys Lys Glu Lys
            1010                1015                1020

Val Tyr Leu Ala Trp Val Pro Ala His Lys Gly Ile Gly Gly Asn
            1025                1030                1035

Glu Gln Val Asp Lys Leu Val Ser Arg Gly Ile Arg Lys Val Leu
            1040                1045                1050

Phe Leu Asp Gly Ile Asp Lys Ala Gln Glu Glu His Glu Lys Tyr
            1055                1060                1065

His Ser Asn Trp Arg Ala Met Ala Ser Glu Phe Asn Leu Pro Pro
            1070                1075                1080

Ile Val Ala Lys Glu Ile Val Ala Ser Cys Asp Lys Cys Gln Leu
            1085                1090                1095

Lys Gly Glu Ala Ile His Gly Gln Val Asp Cys Ser Pro Gly Ile
            1100                1105                1110

Trp Gln Leu Ala Cys Thr His Leu Glu Gly Lys Val Ile Leu Val
            1115                1120                1125

Ala Val His Val Ala Ser Gly Tyr Ile Glu Ala Glu Val Ile Pro
            1130                1135                1140

Ala Glu Thr Gly Gln Glu Thr Ala Tyr Phe Leu Leu Lys Leu Ala
            1145                1150                1155

Gly Arg Trp Pro Val Lys Thr Ile His Thr Ala Asn Gly Ser Asn
            1160                1165                1170

Phe Thr Ser Ala Thr Val Lys Ala Ala Cys Trp Trp Ala Gly Ile
            1175                1180                1185

Lys Gln Glu Phe Gly Ile Pro Tyr Asn Pro Gln Ser Gln Gly Val
            1190                1195                1200

Val Ala Ser Ile Asn Lys Glu Leu Lys Lys Ile Ile Gly Gln Val
            1205                1210                1215

Arg Asp Gln Ala Glu His Leu Lys Thr Ala Val Gln Met Ala Val
            1220                1225                1230

Phe Ile His Asn Phe Lys Arg Lys Gly Gly Ile Gly Glu Tyr Ser
            1235                1240                1245

Ala Gly Glu Arg Ile Val Asp Ile Ile Ala Ser Asp Ile Gln Thr
            1250                1255                1260

Lys Glu Leu Gln Lys Gln Ile Thr Lys Ile Gln Asn Phe Arg Val
            1265                1270                1275

Tyr Tyr Arg Asp Ser Arg Asp Pro Leu Trp Lys Gly Pro Ala Lys
            1280                1285                1290
```

```
Leu Leu Trp Lys Gly Glu Gly Ala Val Val Ile Gln Asp Asn Ser
    1295                1300                1305

Asp Ile Lys Val Val Pro Arg Arg Lys Ala Lys Ile Ile Arg Asp
    1310                1315                1320

Tyr Gly Lys Gln Met Ala Gly Asp Asp Cys Val Ala Ser Arg Gln
    1325                1330                1335

Asp Glu Asp
    1340

<210> SEQ ID NO 11
<211> LENGTH: 625
<212> TYPE: PRT
<213> ORGANISM: Artificial Sequence
<220> FEATURE:
<223> OTHER INFORMATION: Mos1SEnv synthetic HIV envelope protein

<400> SEQUENCE: 11

Met Gly Asn Leu Trp Val Thr Val Tyr Tyr Gly Val Pro Val Trp Lys
1               5                   10                  15

Asp Ala Lys Thr Thr Leu Phe Cys Ala Ser Asp Ala Lys Ala Tyr Glu
            20                  25                  30

Lys Glu Val His Asn Val Trp Ala Thr His Ala Cys Val Pro Thr Asp
        35                  40                  45

Pro Asn Pro Gln Glu Ile Val Leu Gly Asn Val Thr Glu Asn Phe Asn
    50                  55                  60

Met Trp Lys Asn Asp Met Val Asp Gln Met His Glu Asp Ile Ile Ser
65                  70                  75                  80

Leu Trp Asp Ala Ser Leu Glu Pro Cys Val Lys Leu Thr Pro Leu Cys
                85                  90                  95

Val Thr Leu Asn Cys Arg Asn Val Arg Asn Val Ser Ser Asn Gly Thr
            100                 105                 110

Tyr Asn Ile Ile His Asn Glu Thr Tyr Lys Glu Met Lys Asn Cys Ser
        115                 120                 125

Phe Asn Ala Thr Thr Val Val Glu Asp Arg Lys Gln Lys Val His Ala
    130                 135                 140

Leu Phe Tyr Arg Leu Asp Ile Val Pro Leu Asp Glu Asn Asn Ser Ser
145                 150                 155                 160

Glu Lys Ser Ser Glu Asn Ser Ser Glu Tyr Tyr Arg Leu Ile Asn Cys
                165                 170                 175

Asn Thr Ser Ala Ile Thr Gln Ala Cys Pro Lys Val Ser Phe Asp Pro
            180                 185                 190

Ile Pro Ile His Tyr Cys Ala Pro Ala Gly Tyr Ala Ile Leu Lys Cys
        195                 200                 205

Asn Asn Lys Thr Phe Asn Gly Thr Gly Pro Cys Asn Asn Val Ser Thr
    210                 215                 220

Val Gln Cys Thr His Gly Ile Lys Pro Val Val Ser Thr Gln Leu Leu
225                 230                 235                 240

Leu Asn Gly Ser Leu Ala Glu Glu Glu Ile Ile Ile Arg Ser Glu Asn
                245                 250                 255

Leu Thr Asn Asn Ala Lys Thr Ile Ile Val His Leu Asn Glu Thr Val
            260                 265                 270

Asn Ile Thr Cys Thr Arg Pro Asn Asn Asn Thr Arg Lys Ser Ile Arg
        275                 280                 285

Ile Gly Pro Gly Gln Thr Phe Tyr Ala Thr Gly Asp Ile Ile Gly Asp
    290                 295                 300
```

```
Ile Arg Gln Ala His Cys Asn Leu Ser Arg Asp Gly Trp Asn Lys Thr
305 310 315 320

Leu Gln Gly Val Lys Lys Lys Leu Ala Glu His Phe Pro Asn Lys Thr
325 330 335

Ile Lys Phe Ala Pro His Ser Gly Gly Asp Leu Glu Ile Thr Thr His
340 345 350

Thr Phe Asn Cys Arg Gly Glu Phe Phe Tyr Cys Asn Thr Ser Asn Leu
355 360 365

Phe Asn Glu Ser Asn Ile Glu Arg Asn Asp Ser Ile Ile Thr Leu Pro
370 375 380

Cys Arg Ile Lys Gln Ile Ile Asn Met Trp Gln Glu Val Gly Arg Ala
385 390 395 400

Ile Tyr Ala Pro Pro Ile Ala Gly Asn Ile Thr Cys Arg Ser Asn Ile
405 410 415

Thr Gly Leu Leu Leu Thr Arg Asp Gly Gly Ser Asn Asn Gly Val Pro
420 425 430

Asn Asp Thr Glu Thr Phe Arg Pro Gly Gly Gly Asp Met Arg Asn Asn
435 440 445

Trp Arg Ser Glu Leu Tyr Lys Tyr Lys Val Val Glu Val Lys Pro Leu
450 455 460

Gly Val Ala Pro Thr Glu Ala Lys Arg Arg Val Val Glu Arg Glu Lys
465 470 475 480

Arg Ala Val Gly Ile Gly Ala Val Phe Leu Gly Ile Leu Gly Ala Ala
485 490 495

Gly Ser Thr Met Gly Ala Ala Ser Ile Thr Leu Thr Val Gln Ala Arg
500 505 510

Gln Leu Leu Ser Gly Ile Val Gln Gln Gln Ser Asn Leu Leu Arg Ala
515 520 525

Ile Glu Ala Gln Gln His Met Leu Gln Leu Thr Val Trp Gly Ile Lys
530 535 540

Gln Leu Gln Thr Arg Val Leu Ala Ile Glu Arg Tyr Leu Gln Asp Gln
545 550 555 560

Gln Leu Leu Gly Leu Trp Gly Cys Ser Gly Lys Leu Ile Cys Thr Thr
565 570 575

Ala Val Pro Trp Asn Thr Ser Trp Ser Asn Lys Ser Gln Thr Asp Ile
580 585 590

Trp Asp Asn Met Thr Trp Met Gln Trp Asp Lys Glu Ile Gly Asn Tyr
595 600 605

Thr Gly Glu Ile Tyr Arg Leu Leu Glu Glu Ser Gln Asn Gln Gln Glu
610 615 620

Lys
625

<210> SEQ ID NO 12
<211> LENGTH: 711
<212> TYPE: PRT
<213> ORGANISM: Artificial Sequence
<220> FEATURE:
<223> OTHER INFORMATION: Mos2SEnv synthetic HIV envelope protein

<400> SEQUENCE: 12

Met Arg Val Arg Gly Met Leu Arg Asn Trp Gln Gln Trp Trp Ile Trp
1 5 10 15

Ser Ser Leu Gly Phe Trp Met Leu Met Ile Tyr Ser Val Met Gly Asn
20 25 30

```
Leu Trp Val Thr Val Tyr Tyr Gly Val Pro Val Trp Lys Asp Ala Lys
         35                  40                  45

Thr Thr Leu Phe Cys Ala Ser Asp Ala Lys Ala Tyr Glu Lys Glu Val
     50                  55                  60

His Asn Val Trp Ala Thr His Ala Cys Val Pro Thr Asp Pro Asn Pro
 65                  70                  75                  80

Gln Glu Ile Val Leu Gly Asn Val Thr Glu Asn Phe Asn Met Trp Lys
                 85                  90                  95

Asn Asp Met Val Asp Gln Met His Glu Asp Ile Ile Ser Leu Trp Asp
            100                 105                 110

Ala Ser Leu Glu Pro Cys Val Lys Leu Thr Pro Leu Cys Val Thr Leu
        115                 120                 125

Asn Cys Arg Asn Val Arg Asn Val Ser Ser Asn Gly Thr Tyr Asn Ile
130                 135                 140

Ile His Asn Glu Thr Tyr Lys Glu Met Lys Asn Cys Ser Phe Asn Ala
145                 150                 155                 160

Thr Thr Val Val Glu Asp Arg Lys Gln Lys Val His Ala Leu Phe Tyr
                165                 170                 175

Arg Leu Asp Ile Val Pro Leu Asp Glu Asn Asn Ser Ser Glu Lys Ser
            180                 185                 190

Ser Glu Asn Ser Ser Glu Tyr Tyr Arg Leu Ile Asn Cys Asn Thr Ser
        195                 200                 205

Ala Ile Thr Gln Ala Cys Pro Lys Val Ser Phe Asp Pro Ile Pro Ile
    210                 215                 220

His Tyr Cys Ala Pro Ala Gly Tyr Ala Ile Leu Lys Cys Asn Asn Lys
225                 230                 235                 240

Thr Phe Asn Gly Thr Gly Pro Cys Asn Asn Val Ser Thr Val Gln Cys
                245                 250                 255

Thr His Gly Ile Lys Pro Val Val Ser Thr Gln Leu Leu Leu Asn Gly
            260                 265                 270

Ser Leu Ala Glu Glu Glu Ile Ile Ile Arg Ser Glu Asn Leu Thr Asn
        275                 280                 285

Asn Ala Lys Thr Ile Ile Val His Leu Asn Glu Thr Val Asn Ile Thr
    290                 295                 300

Cys Thr Arg Pro Asn Asn Asn Thr Arg Lys Ser Ile Arg Ile Gly Pro
305                 310                 315                 320

Gly Gln Thr Phe Tyr Ala Thr Gly Asp Ile Ile Gly Asp Ile Arg Gln
                325                 330                 335

Ala His Cys Asn Leu Ser Arg Asp Gly Trp Asn Lys Thr Leu Gln Gly
            340                 345                 350

Val Lys Lys Lys Leu Ala Glu His Phe Pro Asn Lys Thr Ile Lys Phe
        355                 360                 365

Ala Pro His Ser Gly Gly Asp Leu Glu Ile Thr Thr His Thr Phe Asn
    370                 375                 380

Cys Arg Gly Glu Phe Phe Tyr Cys Asn Thr Ser Asn Leu Phe Asn Glu
385                 390                 395                 400

Ser Asn Ile Glu Arg Asn Asp Ser Ile Ile Thr Leu Pro Cys Arg Ile
                405                 410                 415

Lys Gln Ile Ile Asn Met Trp Gln Glu Val Gly Arg Ala Ile Tyr Ala
            420                 425                 430

Pro Pro Ile Ala Gly Asn Ile Thr Cys Arg Ser Asn Ile Thr Gly Leu
        435                 440                 445

Leu Leu Thr Arg Asp Gly Gly Ser Asn Asn Gly Val Pro Asn Asp Thr
```

```
                450                 455                 460
Glu Thr Phe Arg Pro Gly Gly Asp Met Arg Asn Asn Trp Arg Ser
465                 470                 475                 480

Glu Leu Tyr Lys Tyr Lys Val Val Glu Val Lys Pro Leu Gly Val Ala
                485                 490                 495

Pro Thr Glu Ala Lys Arg Arg Val Val Glu Arg Glu Lys Arg Ala Val
                500                 505                 510

Gly Ile Gly Ala Val Phe Leu Gly Ile Leu Gly Ala Ala Gly Ser Thr
                515                 520                 525

Met Gly Ala Ala Ser Ile Thr Leu Thr Val Gln Ala Arg Gln Leu Leu
                530                 535                 540

Ser Gly Ile Val Gln Gln Gln Ser Asn Leu Leu Arg Ala Ile Glu Ala
545                 550                 555                 560

Gln Gln His Met Leu Gln Leu Thr Val Trp Gly Ile Lys Gln Leu Gln
                565                 570                 575

Thr Arg Val Leu Ala Ile Glu Arg Tyr Leu Gln Asp Gln Gln Leu Leu
                580                 585                 590

Gly Leu Trp Gly Cys Ser Gly Lys Leu Ile Cys Thr Thr Ala Val Pro
                595                 600                 605

Trp Asn Thr Ser Trp Ser Asn Lys Ser Gln Thr Asp Ile Trp Asp Asn
                610                 615                 620

Met Thr Trp Met Gln Trp Asp Lys Glu Ile Gly Asn Tyr Thr Gly Glu
625                 630                 635                 640

Ile Tyr Arg Leu Leu Glu Glu Ser Gln Asn Gln Glu Lys Asn Glu
                645                 650                 655

Lys Asp Leu Leu Ala Leu Asp Ser Trp Asn Asn Leu Trp Asn Trp Phe
                660                 665                 670

Ser Ile Ser Lys Trp Leu Trp Tyr Ile Lys Ile Phe Ile Met Ile Val
                675                 680                 685

Gly Gly Leu Ile Gly Leu Arg Ile Ile Phe Ala Val Leu Ser Ile Val
                690                 695                 700

Asn Arg Val Arg Gln Gly Tyr
705                 710

<210> SEQ ID NO 13
<211> LENGTH: 30
<212> TYPE: PRT
<213> ORGANISM: Artificial Sequence
<220> FEATURE:
<223> OTHER INFORMATION: T4-fibritin "foldon" trimerization domain

<400> SEQUENCE: 13

Gly Ser Gly Gly Tyr Ile Pro Glu Ala Pro Arg Asp Gly Gln Ala Tyr
1               5                   10                  15

Val Arg Lys Asp Gly Glu Trp Val Leu Leu Ser Thr Phe Leu
                20                  25                  30

<210> SEQ ID NO 14
<211> LENGTH: 32
<212> TYPE: PRT
<213> ORGANISM: Artificial Sequence
<220> FEATURE:
```

```
<223> OTHER INFORMATION: coiled-coil trimerization domain derived
      from GCN4

<400> SEQUENCE: 14

Met Lys Gln Ile Glu Asp Lys Ile Glu Glu Ile Leu Ser Lys Ile Tyr
1               5                   10                  15

His Ile Glu Asn Glu Ile Ala Arg Ile Lys Lys Leu Ile Gly Glu Val
            20                  25                  30
```